(12) United States Patent
Karmali

(10) Patent No.: US 10,378,059 B2
(45) Date of Patent: Aug. 13, 2019

(54) METHODS AND MOLECULAR PHARMACODYNAMIC BIOMARKERS FOR MULTIPLE SIGNALING PATHWAYS IN RESPONSE TO CARBOXYAMIDOTRIAZOLE OROTATE

(71) Applicant: Rashida A Karmali, New York, NY (US)

(72) Inventor: Rashida A Karmali, Brooklyn, NY (US)

(73) Assignee: TACTICAL THERAPEUTICS, INC., New York, NY (US)

( * ) Notice: Subject to any disclaimer, the term of this patent is extended or adjusted under 35 U.S.C. 154(b) by 1056 days.

(21) Appl. No.: 13/957,720

(22) Filed: Aug. 2, 2013

(65) Prior Publication Data
US 2015/0038349 A1    Feb. 5, 2015

(51) Int. Cl.
*G01N 33/50*     (2006.01)
*C12Q 1/6886*    (2018.01)
*G16B 20/00*     (2019.01)

(52) U.S. Cl.
CPC ..... *C12Q 1/6886* (2013.01); *C12Q 2600/106* (2013.01); *C12Q 2600/158* (2013.01); *G16B 20/00* (2019.02)

(58) Field of Classification Search
None
See application file for complete search history.

(56) References Cited

U.S. PATENT DOCUMENTS

| | | | |
|---|---|---|---|
| 8,357,514 B2 | 1/2013 | Arunakumari | |
| 8,409,796 B2 | 4/2013 | Cullen | |
| 8,450,057 B2 | 5/2013 | Gordon | |
| 2003/0170720 A1* | 9/2003 | Van der Kuyl | C12Q 1/6886 435/7.1 |
| 2008/0139592 A1* | 6/2008 | Karmali | A61K 31/4192 514/274 |
| 2012/0202760 A1* | 8/2012 | Karmali | C07D 249/04 514/34 |

OTHER PUBLICATIONS

Loboda et al. (A gene expression signature of RAS pathway dependence predicts response to P13 and RAS pathway inhibitors and expands the population of RAS pathway activated tumors, BMC Medical Genomics, Jun. 30, 2010, 3:26, pp. 2-11).*
Loboda A et al. (Biomarker Discovery: Identification of a Growth Factor Gene Signature. Clin Pharmacol Ther. 2009, 86: pp. 92-96).*
U. Guhnthert et al. (Book: Attempts to Understand Metastasis Formation II), Springer, 1996, 11 pages.*
Roderick et al. ("Ca2+ signaling checkpoints in cancer: remodeling Ca2+ for cancer cell proliferation and survival," Nature Reviews Cancer, 2008, 8, pp. 361-375 (Year: 2008).*
NCI drug dictionary.*
Young K et al, Exp Cell Res 314:2750-2761 (2008).
Witt O et al, Cancer Letter 277: 8-21(20080.
Wang et al Mol Cancer Ther 12: 925-936(2013).
Tan J et al, Mol Cancer Ther 12:853-864(2013).
Stambolic V et al, Mol Cell 8:317-325 (2001).
Smith A et al Clin Cancer Res 18: 4514-4512(2012).
Nusse R Cell Res 15; 28-32 (2005).
Mignen O et al J Cell Sc 118:5615-5623(2005).
Loboda A et al Clin Pharm & Ther 86: 92-96(2009).
Loboda A et al BMC Medical Genomics 3:1-11 (2010).
Liu C et al Proc Natl Adcad Sc 93:11831-36(1996).
Lawson EL et al PLOS ONE 7: 1-14 (2012).
Kohn EC et al Cancer Res 52: 3208-3212 (1992).
Kohn EC et al Proc natl Adac Sc 92: 1307-1311(1995).
Hupe DJ et al JBiol Chem 266:10136-42(1991).
Gou HF et al PLOS ONE 8: 1-6 (20130.
Ge S et al Clin Cancer Res 6: 1248-1254(2000).
Garon EB et al Mol Cencer Ther 12: 890-900(2013).
Enfissi E et at Cell Calcium 36: 450-467(2004)I.
Felder CF et al J Pharm Exp Ther 257: 967-971(1990).
De Robertis A et al, Mol Cancer Ther 12:1180-1189(2013).
Collin I et al, Cancer Signal Trans Ther 1: 3-23(2006).
Song S et al, PLOS 7: 1-11(2012.
Janku F et al, J Clin Onc 30: 777-782(2012).
Fiorio et al Mol Canc Res 6i 535-545(2008).
Alesandro et al J. Cell. Physiol 215:111 (2008).

* cited by examiner

*Primary Examiner* — Jason M Sims
(74) *Attorney, Agent, or Firm* — Rashida A. Karmali, Esq.

(57) ABSTRACT

This invention provides methods, pharmacodynamics biomarker signatures for multiple signaling pathways in a cell sample such as anagen hair, in response to carboxyamidotriazole orotate (CTO) from a subject. CTO has demonstrated response in several cancers having different genomic mutations in clinical studies. This invention provides a diagnostic and prognostic assay for monitoring response to CTO ranging from −100 fold to +25 fold differential expression in several transcriptional signatures associated with tumor inhibition including EGFR, MEK, HDAC, RAS, GFS, WNT, HSP90 or non-voltage dependent calcium signaling, while inducing tumor suppressors signatures such as P53 or EGR1 in the anagen hair assay.

28 Claims, 8 Drawing Sheets

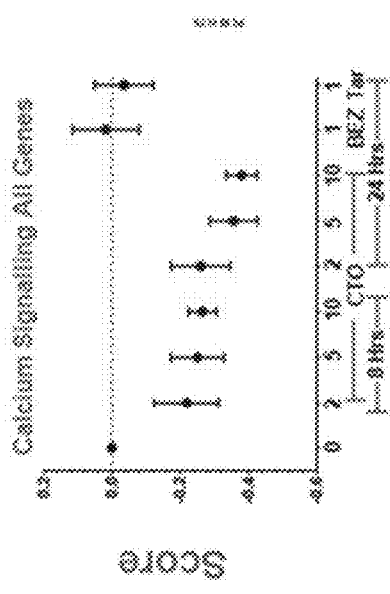
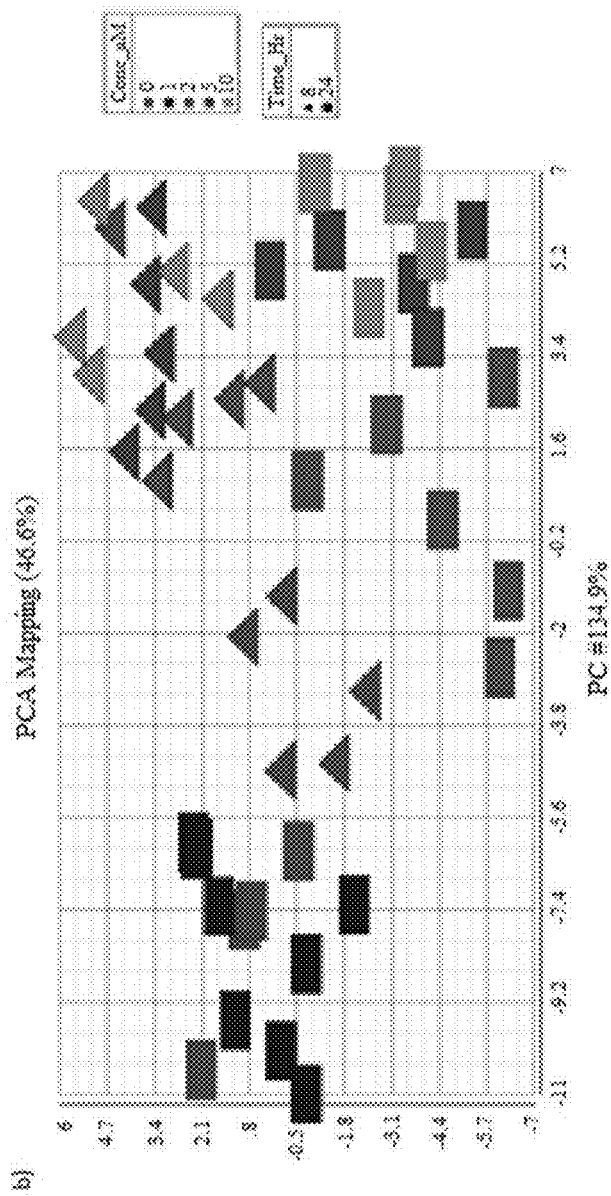
FIG. 7

METHODS AND MOLECULAR PHARMACODYNAMIC BIOMARKERS FOR MULTIPLE SIGNALING PATHWAYS IN RESPONSE TO CARBOXYAMIDOTRIAZOLE OROTATE

FIELD OF INVENTION

This invention is related to evaluation of molecular pharmacodynamics markers in response to carboxyamidotriazole orotate (CTO) in ex vivo human anagen hairs obtained from healthy subjects or patients with different diseases. CTO is an orally active agent with antineoplastic activity, that inhibits non-voltage operated Ca2+ channels, blocking both Ca2+ influx into cells and Ca2+ release from intracellular stores and resulting in the disruption of calcium-mediated signal transduction and inhibition of vascular endothelial growth factor (VEGF) signaling, multiple tyrosine kinase signaling, including AKT, MEK-ERK, or Bcr-Abl. More particularly, the present invention relates to the evaluation of molecular pharmacodynamics biomarkers of overall signaling output by transcriptomic assessment of response to CTO given to patients or when added to ex vivo cultured human anagen hairs in vitro.

1. BACKGROUND TO THE INVENTION

The development of new cancer drugs is now based on the identification of genes that are responsible for driving malignancy and the elucidation of the signal transduction pathways that they hijack. Tremendous advances have been made in the area of small molecule kinase inhibitors to develop targeted therapies designed to interfere with critical molecules and signaling pathways driving tumor growth, for example, Imatinib® (BCR-ABL), Gefitnib® (EGFR), Erlotinib®, (EGFR) and many other agents under preclinical and clinical development. It is important to focus on the pharmacokinetic and metabolic properties as well as on target potency and molecular selectivity to optimize the effects of targeted therapies. Collin, I and Workman, Cancer Signal Transduction Therapy, 1: 3-23 (2006). In the clinical development of the kinase inhibitors, it is important to develop robust and informative biomarkers and develop assays for predicting molecular dependence and hence for identifying patients who will benefit from personalized medicine from a particular agent, and the problem of drug resistance developing.

Another challenge facing the development of molecular therapeutics is the likely need to inhibit several oncogenic targets in order to overcome cancers that are driven by several abnormalities, as well as to prevent or neutralize the development of drug resistance. In some cases resistance to a drug may be linked to increased production of molecules (e.g., cytokines, calcium channel signaling, or molecular signaling) in the tumor micro-environment that interferes with the sensitivity and efficacy of the drugs. Therefore, even the most rationally conceived drug molecule may fail because of mutational changes downstream from its intended target or metabolic features of tumors that never allow the drug to reach its target or that trigger feedback mechanism against the drug molecule.

There are several methods currently in use to overcome drug resistance. One is use of cocktails of highly targeted agents that are designed according to the molecular make-up of the specific cancer. Another approach is to use multi-targeted kinase inhibitors (for example Sorafenib®). A further strategy is to use an inhibitor of several kinases that control many oncogenic players and pathways in malignancy, for example inhibitors of histone deacetylases (HDAC) and the HSP90 molecular chaperone. Garon E. B, et al, Mol Cancer Ther., 12: 890-900 (2013); and Witt O at al, Cancer Letters 277: 8-21 (2009).

Screening and structure-based design of targeted drugs against oncogenic markers driving specific cancers are now delivering targeted drugs for preclinical and clinical studies at a rapid rate. However, there is need to study signaling pathways in normal cells to better understand the factors that cause important tumor suppressor proteins to fail as gatekeepers of normal cellular function. There is need to better understand how these tumor suppressor proteins may be modulated to prevent loss of their normal signaling in response to stress signals.

More particularly, it is important to develop drugs that can aid normal cells to integrate multiple signaling pathways or enhance their role as gate keepers to control growth and proliferation. For example, the P53 transcription factor is a major tumor suppressor protein that serves as a gatekeeper of cellular fate in multicellular organisms. P53 is activated in response to a variety of stress signals and initiates cell cycle arrest, senescence or apoptosis via pathways involving transactivation of P53 target genes. Stambolic V et al., Mol Cell: 317-325 (2001). This universal protection of genetic integrity is however impaired in many human cancers. The new paradigm is to develop agents that target the precise molecular signaling that maintains normal cell cycle, growth and proliferation.

Thus, the rational selection and development of combination treatments is extremely challenging and there is need to develop combinations of targeted drugs and or chemotherapeutic agents based on knowledge of the molecular abnormalities in particular cancers, together with the understanding of the feedback loops that apply upon blockade of a given pathway, as well as enhancing the tumor suppressor signaling pathways of p53 transcription factor and PTEN in normal and cancer cells.

Carboxyamidotriazole orotate (CTO), an orotate salt of carboxyamidotriazole (CAI) is an inhibitor of receptor-operated calcium channel-mediated calcium influx, and is shown to have anti-proliferative and anti-invasive functions in several human cancer cell lines, including human glioblastoma cells. Ge S et al. Clin Cancer Res 6: 1248-1254 (2000). By interrupting calcium mobilization as a second messenger, CAI can inhibit calcium-sensitive signal transduction pathways, including the release of arachidonic acid and its metabolites; nitric oxide release: the generation of inositol phosphates; and tyrosine phosphorylation Kohn E C et al., Cancer Res 52:3208-3212 (1992); Kohn E C et al., Proc Natl Acad Sci 92: 1307-1311 (1995); Felder C F et al. J Pharmacol Exp Therap 257: 967-971 (1990); Hupe D J et al., J Biol Chem 266: 10136-10142 (1991); Mignen O et al., J Cell Sc 118: 5615-5623 (2005); and Enfissi E et al., Cell Calcium 36: 459-467 (2004). CAI inhibits phosphorylation of cellular proteins STATS and CrkL, and induces apoptosis in imatinib mesylate-resistant chronic myeloid leukemia cells by down-regulating BCR-ABL (Alessandro et al, PLOS 7: 1-13 (2012).

In clinical studies (NCT01107522) CTO given alone was safe and tolerable without determining maximum tolerated dose, in cancer patients with different tumor types and having different genomic mutations, and CTO treatment resulted in cancers responding and demonstrating stable disease or partial response showing tumor shrinkage. Thus enormous efforts are directed to the development of molecular pharmacodynamics biomarkers of signaling outputs of CTO to design combinatorial regimens against molecular targets in different types of cancers. Current methods for assessing pathway activation in tumors involve the measurement of the drug targets, known oncogenes or known tumor suppressors. However, one pathway can be activated at multiple points so it is not feasible to assess pathway activation by evaluating just known cancer associated genes.

It is therefore important to develop the complete molecular signatures of CTO in view of its effect on signaling of multiple kinases, tyrosine kinases and calcium signal transduction pathways. The invention is related to evaluation of the response of molecular pharmacodynamics markers in response to CTO treatment in human cell or tissue samples such as anagen hairs obtained from healthy subjects or from patients, either in vivo or in vitro.

In the in vivo model, anagen hairs are obtained before dosing the patient with CTO, and at different time points after the daily dosing of a therapeutic amount of CTO is given. The patient's clinical status and blood levels of CAI are monitored during this period.

In the in vitro model the anagen hairs are obtained from an untreated subject and the hairs are treated in ex vivo cultures with different doses of CTO which represent the range of doses required for therapeutic efficacy.

In both models, RNA is extracted from the bulbs at the end of anagen hairs, cDNA is then prepared from the RNA and global transcriptional or gene expression levels are determined by microarray analysis or by quantitative PCR (qPCR). Bioinformatic analysis is then conducted to identify CTO induced gene expression changes in anagen hairs. Such a protocol can also be applied to issues other than anagen hair obtained from healthy subjects or patients.

Accordingly, the present invention describes in greater detail, uses of the plucked hair biomarker assay to study effects of CTO on mRNA and protein expression levels in vitro. Plucked scalp hair is an ideal surrogate for measuring direct response to treatment with CTO. Highly vascularized, hair follicle can respond within hours of exposure. Given this vascularization, their epithelial nature and rapid rate of proliferation, the cells in the hair bulb at the base of the plucked hair and the outer root sheath are highly relevant surrogate marker tissue for solid tumors. Highly vascularized, the hair follicle can respond to drug treatment within hours of exposure. Bioinformatic analysis was conducted to identify drug-induced changes in hairs.

3. SUMMARY OF THE INVENTION

The present invention relates to the evaluation of molecular pharmacodynamic biomarkers of multiple signaling pathways in response to CTO given in vivo or in vitro, in ex vivo cultured human anagen hairs. Using a commercially available plucked hair molecular platform assay (Epistem Ltd. Manchester, UK) direct response to treatment with different doses of CTO equivalent to levels of carboxyamidotriazole (CAI) that are therapeutically achieved in patients, was evaluated to test targeting intracellular signaling pathways in oncology and other therapeutic areas.

Accordingly, the present invention used plucked scalp hair from subjects, extracted the RNA from the bulbs at the end of the anagen hairs, prepared the cDNA from the RNA, determined the gene expression levels by microarray analysis or quantitative PCR (qPCR) and conducted bioinformatics analysis to identify drug induced gene expression changes for CTO and other drugs, for example, Tarceva® (EGFR inhibitor) or BEZ235 (a PI3K inhibitor).

The invention relates to development of molecular pharmacodynamics biomarkers of signaling output by transcriptomic assessment of response to CTO in ex vivo cultured human anagen hairs from human subjects with or without cancer or other diseases. The molecular pharmacodynamics biomarkers of CTO expose include RAS, GFS (PI3K, PI3/MTOR), MEK, HDAC, NOTCH, WNT-β catenin, HSP90, EGFR, P53, CAIIPA, CAI ex vivo Calcium Signaling Non-voltage dependent, Calcium signaling all genes, Calcium signaling ex vivo, Canonical Calcium Signaling, Canonical Calcium ex vivo, Calcium all genes non-voltage dependent, EGR1, PTEN, TGFβ, CEACAMI, or Dystonin.

In a further aspect the invention provided a method of inhibiting RAS pathway signatures in response to treatment with CTO.

In a further aspect the invention provided a method of inhibiting GFS pathway signatures in response to treatment with CTO.

In a further aspect the invention provided a method of inhibiting MEK pathway signatures in response to treatment with CTO.

In a further aspect the invention provided a method of inhibiting HDAC pathway signatures in response to treatment with CTO.

In a further aspect the invention provided a method of inhibiting NOTCH pathway signatures in response to treatment with CTO.

In a further aspect the invention provided a method of inhibiting WNT-β catenin pathway signatures in response to treatment with CTO.

In a further aspect the invention provided a method of inhibiting HSP900 signatures in response to treatment with CTO.

In a further aspect the invention provided a method of inhibiting EGFR pathway signatures in response to treatment with CTO.

In a further aspect the invention provided a method of inducing P53 pathway signatures in response to treatment with CTO.

In a further aspect the invention provided a method of inhibiting genes associated with non-voltage dependent calcium signaling in response to treatment with CTO. Specifically, the invention provides Signature Scores for the CAI Ingenuity Pathway Analysis, the CAI ex vivo pathway, the calcium signaling pathway and the canonical calcium signaling pathways as pharmacodynamics markers of response to CTO.

In a further aspect the invention provided a method of up regulating EGR1 pathway signatures in response to treatment with CTO.

In a further aspect the invention provided a method of up regulating PTEN pathway signatures in response to treatment with CTO.

In a further aspect the invention provided a method of inducing TGF-β pathway signatures in response to treatment with CTO.

In a further aspect the invention provided a method of down regulating CEACAM1 pathway in response to treatment with CTO.

In a further aspect the invention provided a method of down regulating dystonin pathway in response to treatment with CTO.

The invention also relates to pharmaceutical compositions including CTO and another agent combined to improve sensitivity and efficacy and reduce toxicity while regulating one or more gene signatures including EGFR, MEK, VEGF, HDAC, HSP90, ERK, BCR-ABL, p53, ERG1, CEACAM1, dystonin or genes associates with non-voltage dependent calcium signaling, by monitoring the molecular pharmacodynamics biomarkers of signaling output in response to CTO in ex vivo cultured anagen hairs from a treated mammal.

In an even further aspect the invention provides a method of treating or preventing a condition in a mammal in which the regulation of one or more gene signatures including EGFR, MEK, VEGF, HDAC, HSP90, ERK, BCR-ABL, p53, ERG1, CEACAM1, dystonin, or genes associates with non-voltage dependent calcium signaling, prevents, inhibits or ameliorates a pathology or a symptomology of the condition, the method including administration of a therapeutically effective amount of CTO as monotherapy or as combinatorial therapy, and monitoring the molecular pharmacodynamics biomarkers of signaling output in response to CTO in ex vivo cultured anagen hairs from a treated mammal.

In another aspect the present invention provides a method of preventing or treating a proliferative condition in a subject, the method including administration of a therapeutically effective amount of CTO alone or in combination with another agent, and monitoring the molecular pharmacodynamics biomarkers of signaling output in response to CTO in ex vivo cultured anagen hairs from a treated mammal. Gene expression patterns can be established in other tissues as well to distinguish between tissues in different disease states or to predict prognosis of a disease such as cancer in response to one or more therapies. Another paradigm is to develop a platform of pharmacodynamics markers to design specific and customized formulation base on the gene expression pattern.

The invention provides a paradigm for rational selection and development of combination treatments based on knowledge of the molecular abnormalities in particular diseases or cancer, together with the understanding that CTO may be combined with other targeted agents that are constructed to the molecular makeup of the disease or cancer, together with the understanding that of the feedback loops that apply upon blockade of a given pathway blocked by the targeted drug and how these feedback loops may be prevented, to maintain sustained inhibition of the molecular targets that drive the disease as well as in some instances to induce suppressor genes to optimize the treatment outcome.

The invention provides a shift in the method of developing combinatorial drug regimens inhibiting several oncogenic targets with CTO in order to overcome cancers that are driven by several abnormalities, as well as to prevent or neutralize the development of drug resistance by monitoring the pharmacodynamics biomarkers of signaling output in response to CTO and carefully picked combination drugs, by transcriptomic assessment in ex vivo cultured anagen hairs. The current poly-pharmacology approach using several targeted drugs cocktails has not been successful and has posed new problems due to cumulative toxicities of the drugs in the cocktail.

An important embodiment of the invention is the development of the panel of 15-20 gene mRNA expression signatures from hair samples and deploy this on the cDNA samples generated from patients by Affymetrix array data to identify genes differentially expressed in scalp hair samples from untreated and treated patients.

These and other features of the present teachings are set forth herein.

4. BRIEF DESCRIPTION OF FIGURES

FIG. 1a illustrates the different stages of the plucked hair biomarker platform (Epistem. Ltd. Manchester, UK), including: anagen hair collection from the scalp; ex vivo culture of the hairs for 8 and 24 hrs to different doses of CTO and to reference dose of BEZ235 (PI3K inhibitor) and Tarceva® (EGFR inhibitor) for 24 hrs only; RNA isolation and quality control; Epistem GentRx cDNA amplification; selection of cDNAs passing all quality controls for 5HNVs; sample labeling and microarray hybridization; and bioinformatic analysis using reference databases.

FIG. 1b describes ANOVA analysis of results of transcription response for all contrasts in response to different doses of CTO at 8 hr and 24 hr and for 1 dose of BEZ235 (PI3K inhibitor) and Tarceva® (EGFR inhibitor) for 24 hr only.

FIG. 2a illustrates the results of different doses of CTO on multivariate signatures at 8 hr and 24 hr periods for 11 different signatures starting with the strongest to lowest inhibition—with EGFRi, MEKi, HSP90i, non-voltage dependent CAI related calcium signaling, HDACi, GF and RAS, WNT/β-catenin was inhibitory at 24 hr and no activity was noted for PI3Ki, PI3K/mTOR, NOTCH/GSI. Importantly, P53 was induced and P53 stabilization was noted especially at 24 hr.

FIG. 2b lists 13 different signatures studied.

Figure 5:
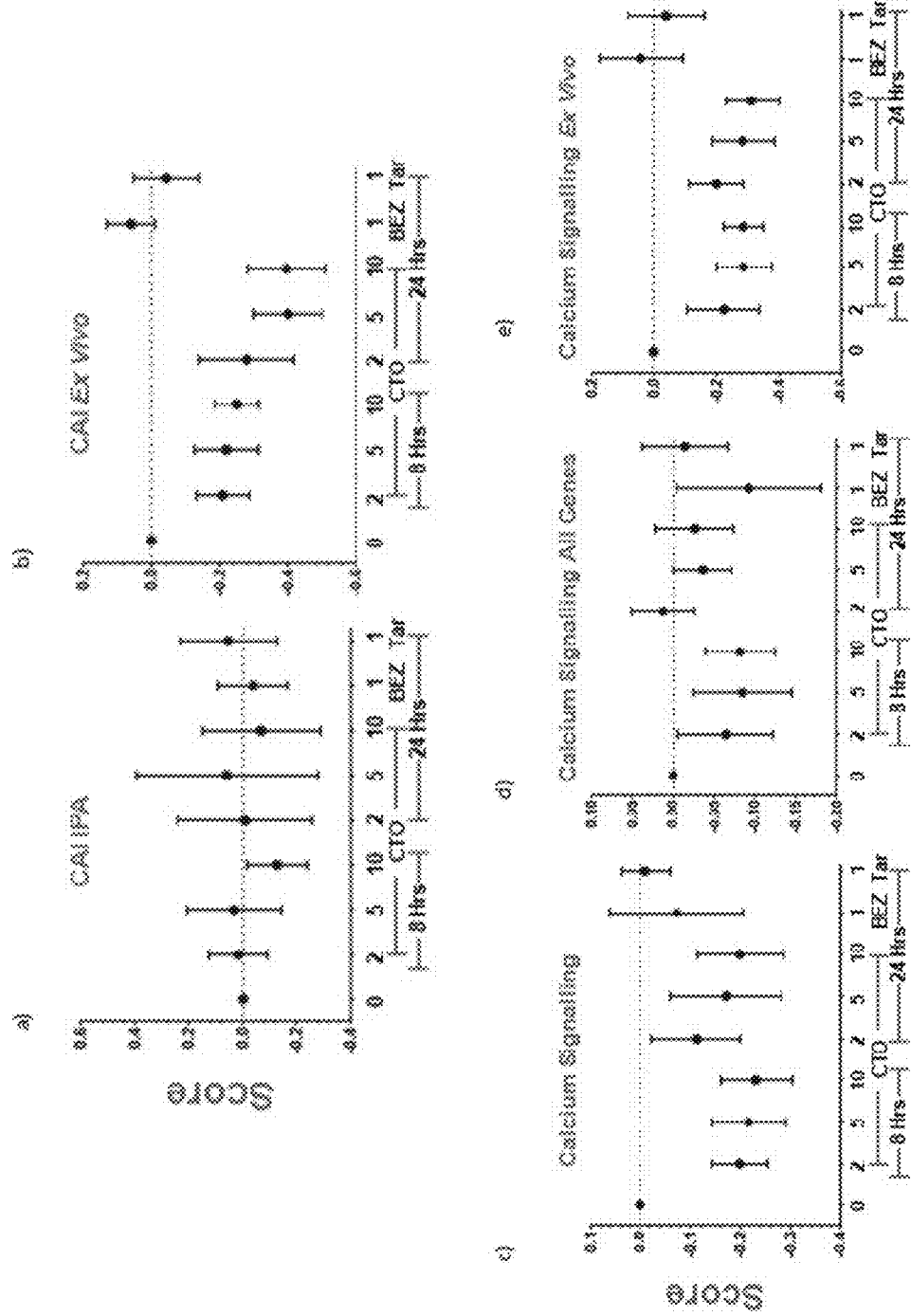

FIG. 5a illustrates the Signature Score for the CAI IPA pathway in response to different doses of CTO at 8 hr and 24 hr compared with BEZ235 and Tarceva® for 24 hr. Using the Ingenuity Pathways Analysis (IPA) (Ingenuity Systems, Redwood City, Calif.) for genes influenced by CAI, some suppression of CAI signature in response to CTO treatment was observed, except at 10 μM. When the 29 genes were filtered from IPA for FDA<0.05 and 1.5 FC in CTO data set, to select informative genes and determine the direction of change, a 14 gene set resulted.

FIG. 5b illustrates the Signature Score for the CAI Ex vivo pathway in response to different doses of CTO at 8 hr and 24 hr compared with BEZ235 and Tarceva® for 24 hr. With the tissue specific direction of change information a strong dose dependent suppression of the IPA CAI list was observed.

FIG. 5c illustrates the Signature Score for the Calcium signaling pathway in response to different doses of CTO at 8 hr and 24 hr compared with BEZ235 and Tarceva® for 24 hr. Non-voltage dependent calcium signaling genes were identified from datasets in literature to inform on regulation.

FIG. 5d illustrates the Signature Score for the Calcium signaling for all gene pathways in response to different doses of CTO at 8 hr and 24 hr compared with BEZ235 and Tarceva® for 24 hr. The estimated regulation direction for all genes was identified.

FIG. 5e illustrates the Signature Score for the Calcium Signaling pathway in response to different doses of CTO at 8 hr and 24 hr compared with BEZ235 and Tarceva® for 24 hr. ANOVA was used to filter informative genes (FDR<0.05 and 1.5 FC).

Strong suppression of non-voltage dependent calcium genes was noted across CTO treatment in both literature determined regulation and ANOVA determined set.

Figure 6:
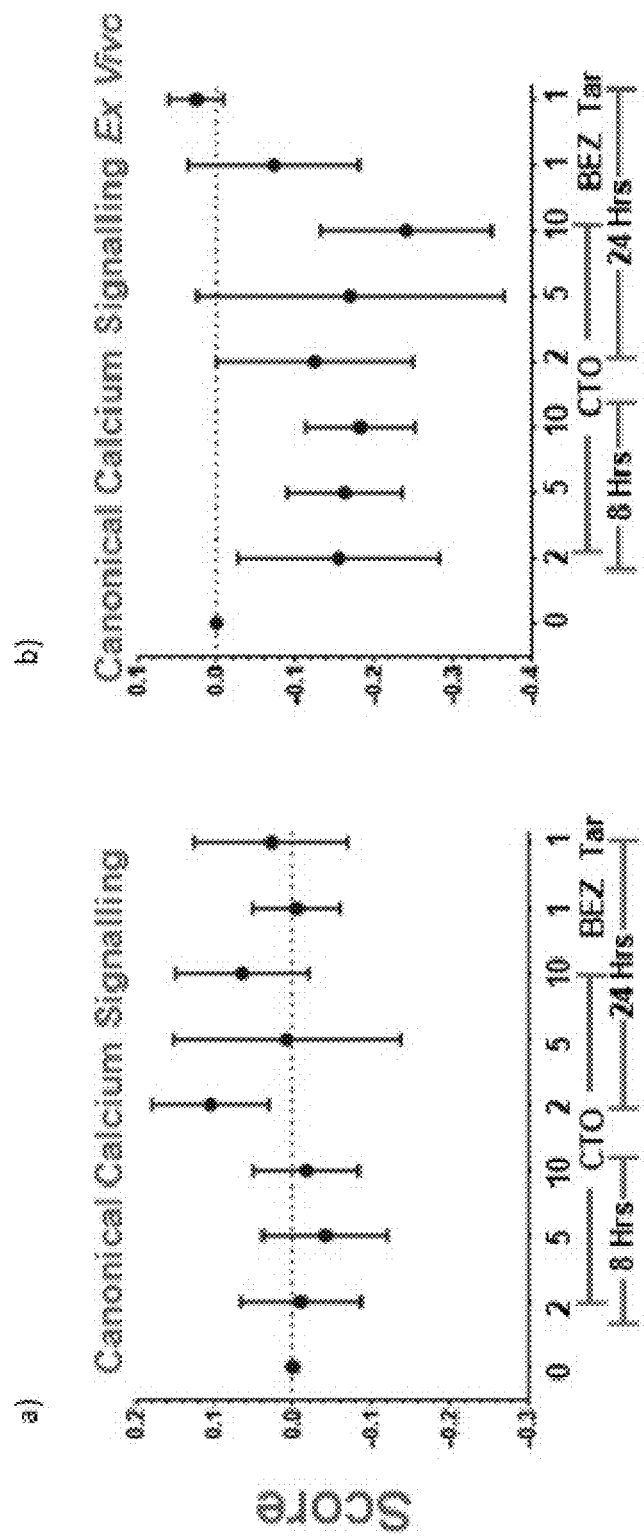

FIG. 6a illustrates the Signature Score for the Canonical Calcium signaling using the KEGG Calcium Signaling and IPA to predict regulation of calcium signaling in response to different doses of CTO at 8 hr and 24 hr compared with BEZ235 and Tarceva® for 24 hr.

FIG. 6b illustrates the Signature Score for the Canonical Calcium signaling ex vivo using the KEGG Calcium Signaling and IPA to predict regulation of in response to different doses of CTO at 8 hr and 24 hr compared with BEZ235 and Tarceva® for 24 hr. Suppression noted for 6/78 canonical pathway genes only.

FIG. 7a illustrates the Signature Score for all Signaling genes after merging of the ANOVA filtered gene sets for both the CAI signature (FIG. 5b) and the non-voltage dependent (NVD) gene sets (FIG. 5c).

FIG. 7b illustrates results in a panel of 31 CAI/Calcium related genes capable of separating the different CTO doses, both by signature view and by PCA.

Figure 8:
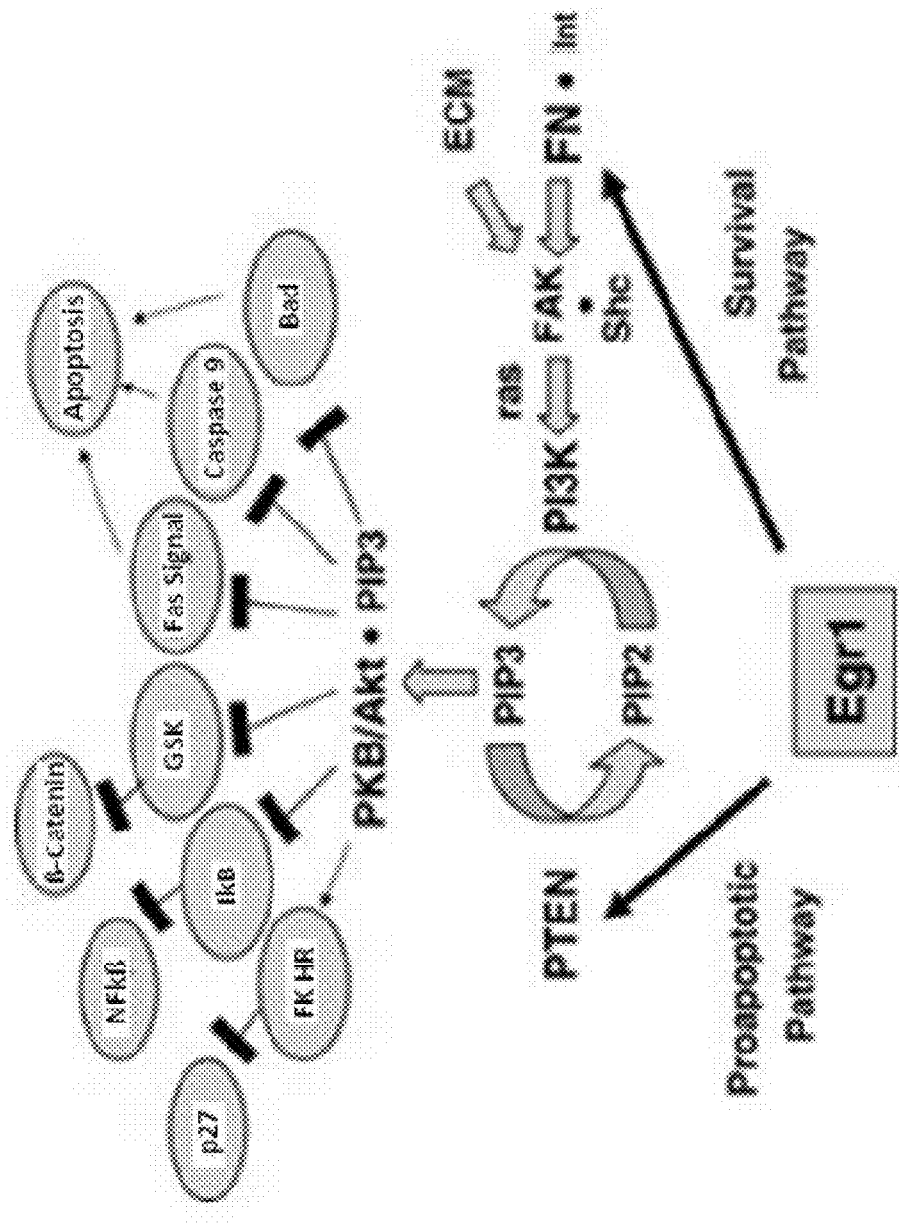

FIG. 8 illustrates the EGR1 Signaling Pathway.

5. DETAILED DESCRIPTION OF THE INVENTION

This invention is related to carboxyamidotriazole orotate (CTO), an orally active agent with antineoplastic activity, that inhibits non-voltage operated Ca2+ channels, blocking both Ca2+ influx into cells and Ca2+ release from intracellular stores and resulting in the disruption of calcium-mediated signal transduction and inhibition of vascular endothelial growth factor (VEGF) signaling, multiple tyrosine kinase signaling, including AKT, MEK-ERK, or BCR-ABL. More particularly, the present invention relates to the evaluation of molecular pharmacodynamics biomarkers of signaling output by transcriptomic assessment of response to CTO in vivo and in vitro cultures in ex vivo cultured human anagen hairs. Anagen hairs are obtained at different time points from subjects given varying doses of CTO treatment. This is the approach used in clinical trials of CTO in patients. Alternately, anagen hairs are obtained from untreated subjects and the hairs are treated with varying doses of CTO in vitro—this approach is not subject to physiological conditions of absorption and delivery and was chosen.

The understanding of cancer biology and the human genome has led to the development of new classes of targeted therapies designed to interfere with critical molecules and signaling pathways driving tumor growth and hold promise to improve outcomes. This is particularly important for oncology therapy due to the large number of approved therapies, low response rates and resistance to many current treatments, and clinical importance of optimal and tailored therapy. To improve on the limitations of cytotoxic chemotherapeutic agents, current approaches to drug design in oncology are aimed at modulating specific cell signaling pathways important for tumor growth and survival. In cancer cells, these pathways become deregulated resulting in aberrant signaling, inhibition of apoptosis, increased metastasis and increased cell proliferation.

Though normal cells integrate multiple signaling pathways for controlled growth and proliferation, tumors seem to be heavily reliant on activation of one or two oncogene pathways. Unfortunately the focus on developing new anticancer therapies is not on inducing the multiple signaling pathways that keep controlled growth or proliferation in normal cells under control. Instead, the components of the aberrant signaling pathways represent attractive selective targets for new anticancer therapies. It seems logical that patients with tumors that are driven by specific oncogenic pathways will respond to therapeutics targeting those pathways. However, one pathway can be activated at multiple points and it is not always feasible to assess pathway activation by evaluating known cancer associated genes. For example, signaling through the phosphatidylinositol 3-kinase (PI3K) pathway is activated by multiple growth factors through receptor tyrosine kinases and has effects on multiple processes, including cell growth and survival, metastatic potential, and drug resistance through gene amplification and/or by pass or new mutations. Many pharmaceutical companies are developing specific inhibitors of one or more signaling pathways and proposing combinations of several specific inhibitors to inhibit multiple oncogene pathways. However, a major limitation to the overall benefit from targeted therapy is the development of drug resistance. Resistance can occur because of mutations that render the drug target insensitive to the inhibitor or when cancer cells change their dependency on the pathway that is targeted. In the first example, resistance can be overcome by developing new drugs that effectively inhibit resistance-associated mutants, as in the example of dasatinib and nilotinib which are effective on BCR-ABL mutants that confer resistance to imatinib. A second approach is to target multiple signaling pathways simultaneously, and thus prevent the cancer from changing its dependency to another significant pathway, for example combining inhibitors of mitogen-activated protein (MAP)-extracellular signal regulated kinase (ERK) kinase with inhibitors of PI3 kinase. The third approach is to enhance efficacy of the targeted therapy to simultaneously target downstream proteins that protect tumor cells from apoptosis.

However, a new approach to develop molecules, each of which could modulate multiple oncogenic pathways would be a better approach to prevent both drug resistance and serious toxicities. This would be a much harder approach to design the molecule, but this approach of developing a molecule capable of modeling multiple oncogenic pathways is deemed inefficient and unacceptable strategy. Yet, probably the best way to inhibit several oncogenic targets in order to overcome cancers that are driven by several molecular abnormalities, as well as to prevent drug resistance and toxicity is to develop molecules that modulate multiple oncogenic pathways and/or induce known tumor suppressors.

By using a molecule that modulates the expression of multiple genes, and by integrating the expression data from these multiple genes, a quantitative assessment of the gene expression signatures may be possible. These gene expression signatures for pathway activation and/or inactivation may be used as i) pharmacodynamics biomarkers to monitor the drug induced pathway inhibition in tumors or surrogate markers such as anagen hair, ii) as prediction biomarkers to identify tumors with high level of a particular pathway; and early efficacy biomarkers to get an early readout of efficacy or prevention.

Carboxyamidotriazole orotate (CTO), an orotate salt of carboxyamidotriazole (CAI) is an inhibitor of receptor-operated calcium channel-mediated calcium influx, and is shown to have anti-proliferative and anti-invasive functions in several human cancer cell lines, including human glioblastoma cells (Fiorio Pla et al, 2008; Ge et al, 2000). By interrupting calcium mobilization as a second messenger, CAI can inhibit calcium-sensitive signal transduction pathways, including the release of arachidonic acid and its metabolites; nitric oxide release; the generation of inositol phosphates; and tyrosine phosphorylation (Ge et al, 2000; Kohn et al, 1992). CAI inhibits phosphorylation of cellular proteins STATS and CrkL, and induces apoptosis in imatinib mesylate-resistant chronic myeloid leukemia cells by down-regulating bcr-abl (Alessandro et al, 2008).

Thus enormous efforts are directed to the development of molecular pharmacodynamics biomarkers of signaling outputs of CTO to design combinatorial regimens against molecular targets in different types of cancers. Current methods for assessing pathway activation in tumors involve the measurement of the drug targets, known oncogenes or known tumor suppressors. However, one pathway can be activated at multiple points so it is not feasible to assess pathway activation by evaluating just known cancer associated genes. The plucked hair biomarker assay is used to study effects of CTO on mRNA and protein expression levels in vitro. Plucked scalp hair is an ideal surrogate for measuring direct response to treatment with CTO. Highly vascularized, hair follicle can respond within hours of exposure. Given this vascularization, their epithelial nature and rapid rate of proliferation, the cells in the hair bulb at the base of the plucked hair and the outer root sheath are highly relevant surrogate marker tissue for solid tumors. Bioinformatic analysis is conducted to identify drug-induced changes in hairs.

The invention relates to development of molecular pharmacodynamics biomarkers of signaling output by transcriptomic assessment of response to CTO in ex vivo cultured human anagen hairs from human subjects with or without cancer or other diseases.

This invention provides methods, pharmacodynamics biomarker signatures for multiple signaling pathways in a cell sample such as anagen hair, in response to carboxyamidotriazole orotate (CTO) from a subject. CTO has demonstrated response in several cancers having different genomic mutations in clinical studies. This invention provides a diagnostic and prognostic assay for monitoring response to CTO ranging from −100 fold to +25 fold differential expression in several transcriptional signatures associated with tumor inhibition including EGFR, MEK, HDAC, RAS, GFS, WNT, HSP90 or non-voltage dependent calcium signaling, while inducing tumor suppressors signatures such as P53 or EGR1 in the anagen hair assay.

A method for quantifying the response to carboxyamidotriazole orotate (CTO) on pharmacodynamics biomarkers of multiple signature pathways, said method comprising:
 a) Obtaining a cell sample obtained from a subject and exposing the cell sample to varying doses of CTO alone, to CTO in combination with another agent or to other agents for different time periods;
 b) Isolating the mRNA from the treated cell sample and preparing representative cDNA there from and measuring the transcriptional alteration in expression in the cell sample resulting from CTO exposure;
 c) Calculating a signature score for each of the pharmacodynamics biomarkers of multiple signature pathways and quantitating the response to the varying doses of CTO exposure, selecting a list of overlapping genes over expressing at two time periods as listed in Table 1; and
 d) Identifying each of the pharmacodynamics biomarkers of multiple signature pathways by at least 3 or more genes in a compiled list and confirming each of the pharmacodynamics biomarkers of multiple signature pathways using reference datasets.

RAS, Growth Factor, PI3 K Signatures

RAS gene products are involved in kinase signaling pathways that control the transcription of genes, which then regulate cell growth and differentiation. The conversion of RAS from a proto-oncogene usually occurs through a point mutation in the gene, and the altered function can affect the cell in different ways because RAS is involved in many signaling pathways that control cell division and cell death. Mutant ras has been identified in cancers of many origins, including pancreas, colon, lung, thyroid, bladder ovarian, breast, skin, liver kidney and some leukemias. Song, S et al., PLOS ONE 7: 1-11 (2012).

GFS is responsive to phosphatidylinositol 3-kinase (PI3K) pathway perturbation and related to phosphatase and tensin homolog (PTEN) degradation. Loboda A et al. Clin Pharm & Therap 1: 92-96 (2009).

Mutations in the 100α subunit of PI3K, called PI3KCA are often responsible for activation of PI3K/AKT and have been reported in several human cancers. Janku F et al., J Clin Oncol 30:777-782 (2012).

EGFR Pathway Signatures:

In a further aspect the invention provided a method of inhibiting EGFR pathway signatures in response to treatment with CTO. Drugs targeting the EGF receptor (EGFR)-antibodies binding the extracellular domain and small-molecule tyrosine kinase inhibitors have expanded treatment options for several solid tumors. The EFGR gene is frequently up regulated in carcinomas of the breast, kidney, ovary, cervix, and in squamous cell carcinomas. The up regulation is typically due to gene amplification or overexpression. EGFR up regulation in gliomas is most often associated with the rearrangement of the EGFR gene resulting in alterations of its transcript so that such gliomas express both wild type endogenous EGFR as well as episomal mutant form. The EGFR gene is amplified in >50% of glioblastomas.

The EGFR-targeted monoclonal antibodies Cetuximab® and Panitumumab® have been extensively studied in metastatic colorectal cancers. However, the clinical efficacy of EGFR-targeted antibodies is limited by the development of acquired secondary resistance which typically occurs within 3 to 12 months of starting therapy. Multiple mechanisms of secondary resistance to anti-EGFR antibodies have been reported such as expression of EGFR ligands, HER2 amplification, and deregulation of the EGFR recycling process. KRAS mutations arise and are responsible for acquired resistance in half the patients who initially respond to cetuximab or panitumumab. Wang J et al., Mol Cancer Ther 12: 925-936 (2013)

During the past several years four EGFR inhibitors have been approved including cetuximab, panitumumab, gefitnib and erlotinib (Tarceva) and have become standard of care for use in cancer patients. However, the activity reported in unselected patients has been quite limited and typically develop resistance. The extent of intrinsic and acquired resistance to EGFR inhibitors thus leaves ample room for further anticancer drug development. Gou H-F et al., PLOS ONE 8: 1-6 (2013)

MEK Pathway Signatures:

In a further aspect the invention provided a method of inhibiting MEK pathway signatures in response to treatment with CTO. The MAPK pathway is commonly activated in human cancers and then activates RAF-MEK-ERK kinase cascade which leads to activation downstream of substrates involved in cell proliferation, survival, transformation, translational control and cytoskeletal rearrangements. Tan N et al., Mol Cancer Ther 12: 853-864 (2013). Small molecule inhibitors targeted this pathway, such as allosteric inhibitors of MEK exhibit anticancer efficacy in vitro and in vivo.

HDAC Pathway Signatures:

In a further aspect the invention provided a method of inhibiting HDAC pathway signatures in response to treatment with CTO. Histone acetylation is a reversible modification, with deacetylation being catalyzed by histone deacetylases (HDACs). HDACs are represented by 18 genes in humans and are divided into four distinct classes. Several classes of HDAC inhibitors are being evaluated in clinical investigations and indicate that certain HDAC family members are aberrantly expressed in several tumors. Unselective HDAC inhibitors show promising results in leukemias and solid tumors, for example Vorinostat® approved for cutaneous T cell Lymphoma. Witt O et al. Cancer Letter 277: 8-21 (2008). However, some pan-HDAC inhibitors may cause numerous side effects thus requiring selective targeting of HDACs with oncogenic function in cancer cells.

WNT Pathway Signatures:

In a further aspect the invention provided a method of inhibiting WNT pathway signatures in response to treatment with CTO. The WNT family of signaling molecules regulates numerous processes in animal development, and WNT malfunction is implicated in various forms of disease including cancer and degenerative diseases. The canonical WNT signaling pathway is regulated at many levels and there is increasing evidence from other systems for crosstalk between WNT signaling and other pathways important in tumorigenesis, converging on B-catenin. B-catenin is a multifunctional protein with distinct molecular roles in cell adhesion at the plasma membrane and in transcription within the nucleus. An increasing number of studies suggest that elevated WNT signaling in glioblastoma (GBM) is initiated by several alternative mechanisms that are involved in different steps of the disease. De Robertis A et al., Mol Cancer Ther 12: 1180-1189 (2013); and Nusse R, Cell Res 15: 28-32 (2005). Therefore, inhibition of WNT signaling may represent a therapeutically relevant approach for GBM treatment.

HSP91 Pathway Signatures:

In a further aspect the invention provided a method of inhibiting HSP90 pathway signatures in response to treatment with CTO. Heat shock protens serve as molecular chaperones required for stability, post translation modification, and function of multiple client proteins. Expression of HSP is increased at times of physiologic stress, and these effects are believed to support cell survival. HSP90 is over expressed in many tumor types indicating that it may play a role in the survival of cancer cells and thus making it an attractive target for an anticancer agent. Increased HSP90 has been linked to worse prognosis in patients with non-small cell lung cancer. Garon E B et al., Mol Cancer Ther 12: 890-900 (2013). NSCLC arises as a result of several driver mutations, for example EGF receptor mutations are seen in about 10% of NSCLC. HSPs play an important role in neurodegenerative disorders such as Parkinson's disease, Alzheimer's disease or Huntington disease and therefore down regulation of HSP90 has potential beneficial effects in cancer and degenerative diseases.

Non-voltage Dependent Calcium Signaling:

In a further aspect the invention provided a method of inhibiting genes associated with non-voltage dependent calcium signaling in response to treatment with CTO. Kohn E C et al., Cancer Res 52:3208-3212 (1992); Kohn E C et al., Proc Natl Acad Sci 92: 1307-1311 (1995) Felder C F et al., J Phasrmacol Exp Therap 257: 967-971 (1990 Hupe D J et al., J Biol Chem 266: 10136-10142 (1991); Mignen O et al., J Cell Sc 118: 5615-5623 (2005); and Enfissi E et al., Cell Calcium 36: 459-467 (2004. Calcium signaling non-voltage dependent genes were identified and strong suppression was noted across CTO treatment.

Canonical calcium signaling was analyzed using the KEGG Calcium Signaling Pathway and IPA to predict regulation of canonical calcium signaling. No significant suppression of pathway was noted. Using ANOVA to filter for informative genes (FDR<0.05 & 1.5) it was noted that suppression of canonical calcium genes occurred across CTO treatment, however this only represented 7/68 canonical pathway genes.

TGF-β Pathway Signatures:

In a further aspect the invention provided a method of inhibiting genes associated with TGF-β signaling in response to treatment with CTO. TGF-β is part of a large family of structurally related cytokines that include bone morphogenic proteins, growth and differentiation factors, activins and inhibins. Nearly every cell type has the ability to secrete TGF-β as well as the ability to respond to TGF-β via the presence of TGF-β receptors on the cell surface. Therefore, gain or loss of function of the TGF-β pathway and its components are to lead to a variety of diseases including cancer. In epithelial cells TGF-β functions as a tumor suppressor, where it inhibits proliferation, induces apoptosis and mediates differentiation. Conversely, in other contexts, TGF-β promotes tumor progression through increasing tumor cell invasion and metastasis. Smith A L et al., Clin Cancer Res 18: 4514-4512 (2012).

CEACAM1 Pathway Signatures:

In a further aspect the invention provided a method of down regulating CEACAM1 pathway in response to treatment with CTO. CEACAM1 is a member of the carcinoembryionic antigen (CEA) gene family of Ig-like cell-cell adhesion molecules. CEACAM1 is down regulated in epithelial cancers, for example prostate, bladder and colon. Lawson E L et al., PLOS ONE 7: 1-14 (2012).

Dystonin/Bpag1 Protein Signatures:

In a further aspect the invention provided a method of down regulating dystonin pathway in response to treatment with CTO. Dystonin/Bpag1 proteins are cytoskeletal linkers whose loss of function in mice results in a hereditary sensory neuropathy with a progressive loss of limb coordination. Young K et al., Exp Cell Res 314:2750-2761 (2008).

P53 Pathway Signatures:

In a further aspect the invention provided a method of inducing P53 pathway signatures in response to treatment with CTO. Normal cells integrate multiple signaling pathways to control growth and proliferation. For example, the p53 transcription factor is a major tumor suppressor protein that serves as a gatekeeper of cellular fate in multicellular organisms. P53 is activated in response to a variety of stress signals and initiates cell cycle arrest, senescence or apoptosis via pathways involving transactivation of p53 target genes. Stambolic V et al., Molecular Cell 8:317-325 (2001). This universal protection of genetic integrity is however impaired in many human cancers.

In a further aspect the invention provided a method of up regulating P53 pathway signatures in response to treatment with CTO. Mutations of PTEN are frequently found in a variety of cancers including brain, breast, endometrial, prostate and kidney tumors. PTEN is a tumor suppressor and is a negative regulator of PI3K/PKB/AKT-dependent cellular survival.

EGR1 Pathway Signatures:

In a further aspect the invention provided a method of up regulating EGR1 pathway signatures in response to treatment with CTO. The early growth response 1 (EGR1) gene product is a transcription factor with roles in differentiation and growth. The transcription factor EGR1 is a direct regulator of multiple tumor suppressor including TGFβ1, PTEN, and fibronectin. Baron V et al., Cancer gene Therapy 13: 115-124 (2006). In certain human tumor cells and tissues EGR1 exhibits prominent tumor suppressor function and many human tumor cell lines express little or no EGR1 in contrast to their normal counterparts. EGR1 is decreased to undetectable in non small cell lung cancers, breast tumors and human gliomas. Reexpression of ERG 1 in human tumor cell lines inhibits transformation. The mechanism of suppression involves the direct induction of TGF-β1 leading to increased fibronectin, and plasminogen activator inhibitor. Liu, C et al Proc Natl Acad Sci 93: 11831-11836 (1996).

EGR1 is implicated in the regulation of P53 in melanoma cells leading to apoptosis and the proapoptotic suppressor gene PTEN is also directly regulated by EGR1.

The invention also relates to pharmaceutical compositions including CTO and another agent combined to improve sensitivity and efficacy and reduce toxicity while regulating one or more gene signatures including EGFR, MEK, VEGF, HDAC, HSP90, ERK, BCR-ABL, p53, ERG1, CEACAM1, dystonin, or genes associates with non-voltage dependent calcium signaling, by monitoring the molecular pharmacodynamic biomarkers of signaling output in response to CTO in ex vivo cultured anangen hairs from a treated mammal.

In an even further aspect the invention provides a method of treating or preventing a condition in a mammal in which the regulation of one or more gene signatures including EGFR, MEK, VEGF, HDAC, HSP90, ERK, BCR-ABL, p53, ERG1, CEACAM1, dystonin, or genes associates with non-voltage dependent calcium signaling, prevents, inhibits or ameliorates a pathology or a symptomology of the condition, the method including administration of a therapeutically effective amount of CTO as monotherapy or as combinatorial therapy, and monitoring the molecular pharmacodynamics biomarkers of signaling output in response to CTO in ex vivo cultured anangen hairs from a treated mammal.

In another aspect the present invention provides a method of preventing or treating a proliferative condition in a subject, the method including administration of a therapeutically effective amount of CTO alone or in combination with another agent, and monitoring the molecular pharmacodynamics biomarkers of signaling output in response to CTO in ex vivo cultured anagen hairs from a treated mammal. Gene expression patterns can be established in other tissues as well to distinguish between tissues in different disease states or to predict prognosis of a disease such as cancer in response to one or more therapies. Another paradigm is to develop a platform of pharmacodynamics markers to design specific and customized formulation base on the gene expression pattern.

The invention provides a paradigm for rational selection and development of combination treatments based on knowledge of the molecular abnormalities in particular diseases or cancer, together with the understanding that CTO may be combined with other targeted agents that are constructed to the molecular makeup of the disease or cancer, together with the understanding that of the feedback loops that apply upon blockade of a given pathway blocked by the targeted drug and how these feedback loops may be prevented, to maintain sustained inhibition of the molecular targets that drive the disease as well as in some instances to induce suppressor genes to optimize the treatment outcome.

The invention provides a shift in the method of developing combinatorial drug regimens inhibiting several oncogenic targets with CTO in order to overcome cancers that are driven by several abnormalities, as well as to prevent or neutralize the development of drug resistance by monitoring the pharmacodynamics biomarkers of signaling output in response to CTO and carefully picked combination drugs, by transcriptomic assessment in ex vivo cultured anagen hairs. The current poly-pharmacology approach using several targeted drugs cocktails has not been successful and has posed new problems due to cumulative toxicities of the drugs in the cocktail. The invention provides a rescue solution for targeted and non-targeted drug combinations that fail due to drug resistance mechanisms by combining them with CTO from the start or even after drug resistance is noted, to maintain sincitivity and effectiveness.

An important embodiment of the invention is the development of the panel of up to 15-20 gene mRNA expression signatures from hair samples and deploy this on the cDNA samples generated from patients by Affymetrix array data to identify genes differentially expressed in scalp hair samples from untreated and treated patients.

It is an objective of the present invention to evaluate molecular pharmacodynamic markers in response to carboxyamidotriazole orotate (CTO) in ex vivo human anagen hairs obtained from subjects. CTO is an orally active agent with antineoplastic activity, that inhibits non-voltage operated Ca2+ channels, blocking both Ca2+ influx into cells and Ca2+ release from intracellular stores and resulting in the disruption of calcium-mediated signal transduction and inhibition of vascular endothelial growth factor (VEGF) signaling, multiple tyrosine kinase signaling, including AKT, MEK-ERK, or BCR-ABL. More particularly, the present invention relates to the evaluation of molecular pharmacodynamics biomarkers of signaling output by transcriptomic assessment of response to CTO in ex vivo cultured human anagen hairs.

6. EXAMPLES

Example 1

Figure 1:
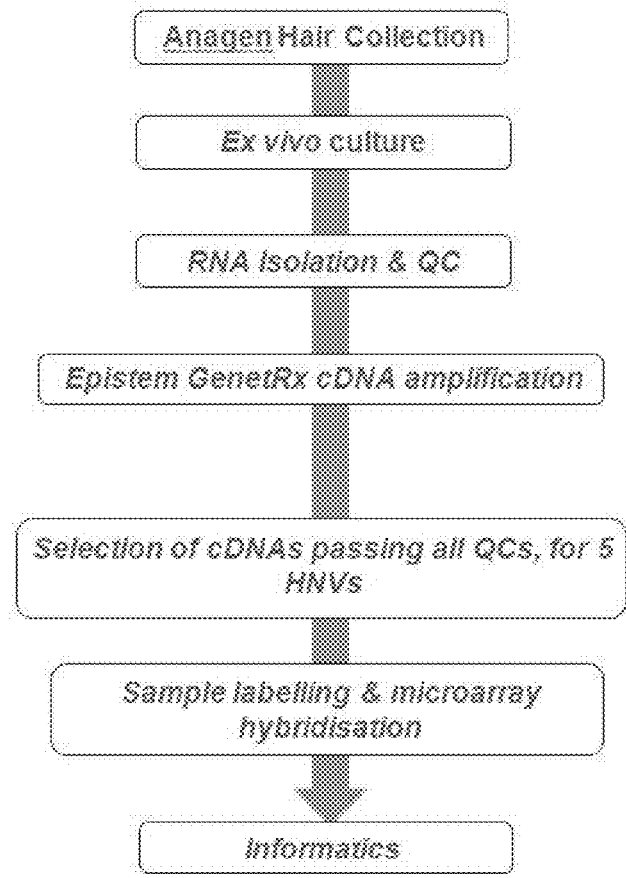

The plucked hair biomarker platform developed by Epistem Ltd (Manchester, United Kingdom) was used to assess transcriptomic response to CTO in ex vivo cultured human anagen hairs. FIG. 1a describes the overall process steps.

Plucked scalp hair is an ideal surrogate for measuring direct response to CTO treatment. It is a non-invasive and can also be used using samples from patients who have been treated with CTO, in which case the hairs do not need to be treated ex vivo. Hairs growing on the scalp in growth stage (anagen) and which have highly vascularized follicles are suitable.

Donor hairs were plucked from 5 male donor volunteers, immediately transferred to maintenance medium cultures and exposed to varying doses of CTO equivalent to 2 M, 5 µM, and 10 µM carboxyamidotriazole (CAI). The cultures were either maintained for 8 hrs or 24 hrs. Controls were used, for example, Tarceva®. (EGFR inhibitor) at 1 µM and BEZ235 (PI3K inhibitor) at 1 µM for 24 hrs only. Once in culture hairs were collected at the specified periods for mRNA isolation or protein analysis to ensure quality control. Small amounts of RNA (about up to 500 ng) are extracted from the bulbs at the end of the anagen hairs. Representative cDNA was prepared from the RNA and gene expression levels determined by microarray analysis. Biotin labeling, fragmentation and hybridization to 048 Affymetrix U133 plus 2.0 array was done. Bioinformatic analysis was done to identify CTO induced gene expression changes. The whole procedure is given in FIG. 1.

Results obtained show strong transcriptional response for all contrasts. High level of differential expression of transcripts was observed. Tarceva® showed less differential probes than CTO or BEZ235 at this threshold. For CTO differential probes increased in a dose related manner. CTO showed the greatest effect transcriptionally in anagen hair at all doses compared with BEZ235 or Tarceva®). Results are presented in detail in FIG. 1b. Biologically relevant alteration of the hair bulb transcriptome ranging from −100 fold to +25 fold differential expression was observed at clinically relevant levels of CTO.

Example 2

The signature scores were assessed as described in detail by Loboda A., et al (Clinical Pharmacology & Therapeutics 86:92-96 (2009) for identification of growth factor gene signatures, and by Loboda A et al, BMC Medical Genomics 3: 1-11 (2010) for identification of signatures of RAS pathway and PI3K. These references are incorporated herein. They describe the Ingenuity Pathway Analysis (Ingenuity Systems, Redwood City, Calif.); http://www.ingenuity.com software tool to identify signaling pathways that are statistically enriched among growth factor signature genes. The RAS pathway was analyzed using publicly available and literature datasets, e.g., https:/array.nci.nih.gov/carray/project/woost-00041.

The results obtained for probes observed at the two time periods were: 1440 at 8 hours and 2961 at 24 hrs. A high degree overlap was observed between the 2 lists (39%, $p<0.0001$). The net result was 558 probes (442 unique annotated genes, ranging −75 to +33 fold at high dose CTO/24 hr. Significant results of Signature Scores are presented graphically. The Probe List is presented in Table 1.

TABLE 1

| Probeset ID | Entrez Gene | Gene Symbol | Gene Title |
|---|---|---|---|
| 222450_at | 56937 | PMEPA1 | prostate transmembrane protein, androgen induced 1 |
| 233565_s_at | 100528031 /// 27111 | FKBP1A-SDCBP2 /// SDCBP2 | FKBP1A-SDCBP2 readthrough (non-protein coding) /// syndecan binding protein (syntenin) |
| 242832_at | 5187 | PER1 | period homolog 1 (*Drosophila*) |
| 240463_at | — | — | — |
| 213039_at | 23370 | ARHGEF18 | Rho/Rac guanine nucleotide exchange factor (GEF) 18 |
| 235072_s_at | 63971 | KIF13A | kinesin family member 13A |
| 208926_at | 4758 | NEU1 | sialidase 1 (lysosomal sialidase) |
| 237444_at | — | — | — |
| 239451_at | — | — | — |
| 222288_at | — | — | — |
| 227579_at | 2241 | FER | fer (fps/fes related) tyrosine kinase |
| 212717_at | 9842 | PLEKHM1 | pleckstrin homology domain containing, family M (with RUN domain) member 1 |
| 226853_at | 55589 | BMP2K | BMP2 inducible kinase |
| 214112_s_at | 541578 /// 91966 | CXorf40A /// CXorf40B | chromosome X open reading frame 40A /// chromosome X open reading frame 40B |
| 209012_at | 7204 | TRIO | triple functional domain (PTPRF interacting) |
| 219476_at | 79098 | C1orf116 | chromosome 1 open reading frame 116 |
| 238086_at | 100129617 | LOC100129617 | uncharacterized LOC100129617 |
| 230721_at | 730094 | C16orf52 | chromosome 16 open reading frame 52 |
| 1566079_at | 647190 | RPS16P5 | ribosomal protein S16 pseudogene 5 |
| 223839_s_at | 6319 | SCD | stearoyl-CoA desaturase (delta-9-desaturase) |
| 225671_at | 124976 | SPNS2 | spinster homolog 2 (*Drosophila*) |

TABLE 1-continued

| Probeset ID | Entrez Gene | Gene Symbol | Gene Title |
| --- | --- | --- | --- |
| 212961_x_at | 541578 | CXorf40B | chromosome X open reading frame 40B |
| 223659_at | 84000 | TMPRSS13 | transmembrane protease, serine 13 |
| 229909_at | 283358 | B4GALNT3 | beta-1,4-N-acetyl-galactosaminyl transferase 3 |
| 223467_at | 51655 | RASD1 | RAS, dexamethasone-induced 1 |
| 235146_at | 57458 | TMCC3 | transmembrane and coiled-coil domain family 3 |
| 235548_at | 164284 | APCDD1L | adenomatosis polyposis coli down-regulated 1-like |
| 206816_s_at | 26206 | SPAG8 | sperm associated antigen 8 |
| 242323_at | 81579 | PLA2G12A | phospholipase A2, group XIIA |
| 224579_at | 81539 | SLC38A1 | solute carrier family 38, member 1 |
| 213315_x_at | 91966 | CXorf40A | chromosome X open reading frame 40A |
| 227314_at | 3673 | ITGA2 | integrin, alpha 2 (CD49B, alpha 2 subunit of VLA-2 receptor) |
| 227093_at | 57602 | USP36 | Ubiquitin specific peptidase 36 |
| 200760_s_at | 10550 | ARL6IP5 | ADP-ribosylation-like factor 6 interacting protein 5 |
| 201790_s_at | 1717 | DHCR7 | 7-dehydrocholesterol reductase |
| 1554980_a_at | 467 | ATF3 | activating transcription factor 3 |
| 242255_at | 22884 | WDR37 | WD repeat domain 37 |
| 219267_at | 51228 | GLTP | glycolipid transfer protein |
| 1555786_s_at | 645687 | LINC00520 | long intergenic non-protein coding RNA 520 |
| 229734_at | 283174 | LOC283174 | uncharacterized LOC283174 |
| 242856_at | — | — | — |
| 201037_at | 5214 | PFKP | phosphofructokinase, platelet |
| 1562970_at | — | — | — |
| 201465_s_at | 3725 | JUN | jun proto-oncogene |
| 202067_s_at | 3949 | LDLR | low density lipoprotein receptor |
| 223679_at | 1499 | CTNNB1 | catenin (cadherin-associated protein), beta 1, 88 kDa |
| 201235_s_at | 7832 | BTG2 | BTG family, member 2 |
| 225662_at | 51776 | ZAK | sterile alpha motif and leucine zipper containing kinase AZK |
| 204401_at | 3783 | KCNN4 | potassium intermediate/small conductance calcium-activated channel, subfamily N, member |
| 222906_at | 28982 | FLVCR1 | feline leukemia virus subgroup C cellular receptor 1 |
| 238613_at | 51776 | ZAK | sterile alpha motif and leucine zipper containing kinase AZK |
| 206414_s_at | 8853 | ASAP2 | ArfGAP with SH3 domain, ankyrin repeat and PH domain 2 |
| 210794_s_at | 55384 | MEG3 | maternally expressed 3 (non-protein coding) |
| 226621_at | 9180 | OSMR | oncostatin M receptor |
| 230682_x_at | 8714 | ABCC3 | ATP-binding cassette, sub-family C (CFTR/MRP), member 3 |
| 235668_at | 639 | PRDM1 | PR domain containing 1, with ZNF domain |
| 205483_s_at | 9636 | ISG15 | ISG15 ubiquitin-like modifier |
| 215808_at | 5655 | KLK10 | kallikrein-related peptidase 10 |
| 212281_s_at | 27346 | TMEM97 | transmembrane protein 97 |
| 212282_at | 27346 | TMEM97 | transmembrane protein 97 |
| 226287_at | 91057 | CCDC34 | coiled-coil domain containing 34 |
| 213618_at | 116984 | ARAP2 | ArfGAP with RhoGAP domain, ankyrin repeat and PH domain 2 |
| 231089_at | 100505664 | LOC100505664 | uncharacterized LOC100505664 |
| 227140_at | 3624 | INHBA | inhibin, beta A |
| 231467_at | — | — | — |
| 202967_at | 2941 | GSTA4 | glutathione S-transferase alpha 4 |
| 230323_s_at | 120224 | TMEM45B | transmembrane protein 45B |
| 224471_s_at | 8945 | BTRC | beta-transducin repeat containing E3 ubiquitin protein ligase |

TABLE 1-continued

| Probeset ID | Entrez Gene | Gene Symbol | Gene Title |
|---|---|---|---|
| 202708_s_at | 8349 | HIST2H2BE | histone cluster 2, H2be |
| 242871_at | 54852 | PAQR5 | progestin and adipoQ receptor family member V |
| 205627_at | 978 | CDA | cytidine deaminase |
| 235542_at | 200424 | TET3 | tet methylcytosine dioxygenase 3 |
| 240410_at | — | — | — |
| 236656_s_at | 100288911 | LOC100288911 | uncharacterized LOC100288911 |
| 206164_at | 9635 | CLCA2 | chloride channel accessory 2 |
| 203159_at | 2744 | GLS | glutaminase |
| 224991_at | 80790 | CMIP | c-Maf inducing protein |
| 204258_at | 1105 | CHD1 | chromodomain helicase DNA binding protein 1 |
| 228249_at | 119710 | C11orf74 | chromosome 11 open reading frame 74 |
| 229013_at | 145783 | LOC145783 | uncharacterized LOC145783 |
| 211547_s_at | 5048 | PAFAH1B1 | platelet-activating factor acetylhydrolase 1b, regulatory subunit 1 (45 kDa) |
| 226863_at | 642273 | FAM110C | family with sequence similarity 110, member C |
| 208161_s_at | 8714 | ABCC3 | ATP-binding cassette, sub-family C (CFTR/MRP), member 3 |
| 214805_at | 1973 | EIF4A1 | eukaryotic translation initiation factor 4A1 |
| 229429_x_at | 728855 /// 728875 | LOC728855 /// LOC728875 | uncharacterized LOC728855 /// uncharacterized LOC728875 |
| 202720_at | 26136 | TES | testis derived transcript (3 LIM domains) |
| 224995_at | 56907 | SPIRE1 | spire homolog 1 (*Drosophila*) |
| 214771_x_at | 23164 | MPRIP | myosin phosphatase Rho interacting protein |
| 201939_at | 10769 | PLK2 | polo-like kinase 2 |
| 238587_at | 84959 | UBASH3B | ubiquitin associated and SH3 domain containing B |
| 232113_at | — | — | — |
| 208690_s_at | 9124 | PDLIM1 | PDZ and LIM domain 1 |
| 201464_x_at | 3725 | JUN | jun proto-oncogene |
| 236657_at | 100288911 | LOC100288911 | uncharacterized LOC100288911 |
| 215541_s_at | 1729 | DIAPH1 | diaphanous homolog 1 (*Drosophila*) |
| 238028_at | 647024 | C6orf132 | chromosome 6 open reading frame 132 |
| 226893_at | 27 | ABL2 | v-abl Abelson murine leukemia viral oncogene homolog 2 |
| 237576_x_at | 100506480 | LOC100506480 | uncharacterized LOC100506480 |
| 1552256_a_at | 949 | SCARB1 | scavenger receptor class B, member 1 |
| 215255_at | 22997 | IGSF9B | immunoglobulin superfamily, member 9B |
| 1557258_a_at | 8915 | BCL10 | B-cell CLL/lymphoma 10 |
| 240623_at | — | — | — |
| 228754_at | 6533 | SLC6A6 | solute carrier family 6 (neurotransmitter transporter, taurine), member 6 |
| 217257_at | 6452 | SH3BP2 | SH3-domain binding protein 2 |
| 241036_at | — | — | — |
| 242553_at | 8714 | ABCC3 | ATP-binding cassette, sub-family C (CFTK/MRP), member 3 |
| 239358_at | — | — | — |
| 210868_s_at | 79071 | ELOVL6 | ELOVL fatty acid elongase 6 |
| 200815_s_at | 5048 | PAFAH1B1 | platelet-activating factor acetylhydrolase 1b, regulatory subunit 1 (45 kDa) |
| 208436_s_at | 3665 | IRF7 | interferon regulatory factor 7 |
| 208138_at | 2520 | GAST | gastrin |
| 241780_at | — | — | — |
| 200730_s_at | 7803 | PTP4A1 | protein tyrosine phosphatase type IVA, member 1 |
| 219697_at | 9956 | HS3ST2 | heparan sulfate (glucosamine) 3-O-sulfotransferase 2 |
| 201693_s_at | 1958 | EGR1 | early growth response 1 |
| 218847_at | 10644 | IGF2BP2 | insulin-like growth factor 2 mRNA binding protein 2 |
| 230469_at | 219790 | RTKN2 | rhotekin 2 |

TABLE 1-continued

| Probeset ID | Entrez Gene | Gene Symbol | Gene Title |
| --- | --- | --- | --- |
| 209917_s_at | 11257 | TP53TG1 | TP53 target 1 (non-protein coding) |
| 224329_s_at | 84518 | CNFN | cornifelin |
| 212253_x_at | 100652766 /// 667 | DST /// LOC100652766 | dystonin /// dystonin-like |
| 238058_at | 150381 | LOC150381 | uncharacterized LOC150381 |
| 239334_at | 57488 | ESYT2 | Extended synaptotagmin-like protein 2 |
| 222271_at | — | — | — |
| 216718_at | 388699 | LINC00302 | long intergenic non-protein coding RNA 302 |
| 219076_s_at | 5827 | PXMP2 | peroxisomal membrane protein 2, 22 kDa |
| 204475_at | 4312 | MMP1 | matrix metallopeptidase 1 (interstitial collagenase) |
| 221185_s_at | 84223 | IQCG | IQ motif containing G |
| 203586_s_at | 379 | ARL4D | ADP-ribosylation factor-like 4D |
| 217802_s_at | 64710 | NUCKS1 | nuclear casein kinase and cyclin-dependent kinase substrate 1 |
| 205767_at | 2069 | EREG | epiregulin |
| 228360_at | 130576 | LYPD6B | LY6/PLAUR domain containing 6B |
| 228917_at | — | — | — |
| 228748_at | 966 | CD59 | CD59 molecule, complement regulatory protein |
| 219632_s_at | 23729 /// 7442 | SHPK /// TRPV1 | sedoheptulokinase /// transient receptor potential cation channel, subfamily V, member |
| 238715_at | 646014 | LOC646014 | Uncharacterized LOC646014 |
| 218810_at | 80149 | ZC3H12A | zinc finger CCCH-type containing 12A |
| 225177_at | 80223 | RAB11FIP1 | RAB11 family interacting protein 1 (class I) |
| 224454_at | 55500 | ETNK1 | ethanolamine kinase 1 |
| 209498_at | 634 | CEACAM1 | carcinoembryonic antigen-related cell adhesion molecule 1 (biliary glycoprotein) |
| 1557257_at | 8915 | BCL10 | B-cell CLL/lymphoma 10 |
| 225133_at | 51274 | KLF3 | Kruppel-like factor 3 (basic) |
| 202340_x_at | 3164 | NR4A1 | nuclear receptor subfamily 4, group A, member 1 |
| 1556545_at | — | — | — |
| 212474_at | 23080 | AVL9 | AVL9 homolog (S. cerevisiase) |
| 210241_s_at | 11257 | TP53TG1 | TP53 target 1 (non-protein coding) |
| 243543_at | — | — | — |
| 239132_at | 4842 | NOS1 | nitric oxide synthase 1 (neuronal) |
| 222757_s_at | 51776 | ZAK | sterile alpha motif and leucine zipper containing kinase AZK |
| 201194_at | 6415 | SEPW1 | selenoprotein W, 1 |
| 229874_x_at | 100506687 | LOC100506687 | uncharacterized LOC100506687 |
| 202557_at | 6782 | HSPA13 | heat shock protein 70 kDa family, member 13 |
| 239669_at | — | — | — |
| 231907_at | 27 | ABL2 | v-abl Abelson murine leukemia viral oncogene homolog 2 |
| 229074_at | 30844 | EHD4 | EH-domain containing 4 |
| 205428_s_at | 794 | CALB2 | calbindin 2 |
| 205822_s_at | 3157 | HMGCS1 | 3-hydroxy-3-methylglutaryl-CoA synthase 1 (soluble) |
| 210869_s_at | 4162 | MCAM | melanoma cell adhesion molecule |
| 225665_at | 51776 | ZAK | sterile alpha motif and leucine zipper containing kinase AZK |
| 212781_at | 5930 | RBBP6 | retinoblastoma binding protein 6 |
| 232355_at | 767579 | SNORD114-3 | small nucleolar RNA, C/D box 114-3 |
| 213288_at | 129642 | MBOAT2 | membrane bound O-acyltransferase domain containing 2 |
| 221666_s_at | 29108 | PYCARD | PYD and CARD domain containing |
| 203072_at | 4643 | MYO1E | myosin IE |
| 215465_at | 26154 | ABCA12 | ATP-binding cassette, sub-famiiy A (ABC1), member 12 |

TABLE 1-continued

| Probeset ID | Entrez Gene | Gene Symbol | Gene Title |
|---|---|---|---|
| 224453_s_at | 55500 | ETNK1 | ethanolamine kinase 1 |
| 216935_at | 388699 | LINC00302 | long intergenic non-protein coding RNA 302 |
| 209086_x_at | 4162 | MCAM | melanoma cell adhesion molecule |
| 218833_at | 51776 | ZAK | sterile alpha motif and leucine zipper containing kinase AZK |
| 209377_s_at | 9324 | HMGN3 | high mobility group nucleosomal binding domain 3 |
| 223519_at | 51776 | ZAK | sterile alpha motif and leucine zipper containing kinase AZK |
| 210138_at | 8601 | RGS20 | regulator of G-protein signaling 20 |
| 1558845_at | 100506089 | LOC100506089 | uncharacterized LOC100506089 |
| 201819_at | 949 | SCARB1 | scavenger receptor class B, member 1 |
| 204310_s_at | 4882 | NPR2 | natriuretic peptide receptor B/guanylate cyclase B (atrionatriuretic peptide receptor B |
| 239377_at | 84285 | EIF1AD | eukaryotic translation initiation factor 1A domain containing |
| 224611_s_at | 80331 | DNAJC5 | DnaJ (Hsp40) homolog, subfamily C, member 5 |
| 219155_at | 26207 | PITPNC1 | phosphatidylinositol transfer protein, cytoplasmic 1 |
| 227163_at | 119391 | GSTO2 | glutathione S-transferase omega 2 |
| 209633_at | 5523 | PPP2R3A | protein phosphatase 2, regulatory subunit B'', alpha |
| 219681_s_at | 80223 | RAB11FIP1 | RAB11 family interacting protein 1 (class I) |
| 221860_at | 3191 | HNRNPL | heterogeneous nuclear ribonucleoprotein L |
| 243296_at | 10135 | NAMPT | Nicotinamide phosphoribosyltransferase |
| 237133_at | — | — | — |
| 1556000_s_at | 55727 | BTBD7 | BTB (POZ) domain containing 7 |
| 204681_s_at | 9771 | RAPGEF5 | Rap guanine nucleotide exchange factor (GEF) 5 |
| 215726_s_at | 1528 | CYB5A | cytochrome b5 type A (microsomal) |
| 210886_x_at | 11257 | TP53TG1 | TP53 target 1 (non-protein coding) |
| 226597_at | 92840 | REEP6 | receptor accessory protein 6 |
| 204995_at | 8851 | CDK5R1 | cyclin-dependent kinase 5, regulatory subunit 1 (p35) |
| 236119_s_at | 6706 | SPRR2G | small proline-rich protein 2G |
| 219228_at | 55422 | ZNF331 | zinc finger protein 331 |
| 234971_x_at | 113026 | PLCD3 | phospholipase C, delta 3 |
| 201127_s_at | 47 | ACLY | ATP citrate lyase |
| 226880_at | 64710 | NUCKS1 | Nuclear casein kinase and cyclin-dependent kinase substrate 1 |
| 209383_at | 1649 | DDIT3 | DNA-damage-inducible transcript 3 |
| 204168_at | 4258 | MGST2 | microsomal glutathione S-transferase 2 |
| 239670_at | 65268 | WNK2 | WNK lysine deficient protein kinase 2 |
| 208512_s_at | 4301 | MLLT4 | myeloid/lymphoid or mixed-lineage leukemia (trithorax homolog, Drosophila); translocate |
| 213281_at | 3725 | JUN | Jun proto-oncogene |
| 218310_at | 154881 /// 27342 | KCTD7 /// RABGEF1 | potassium channel tetramerisation domain containing 7 /// RAB guanine nucleotide exchan |
| 205151_s_at | 9865 | TRIL | TLR4 interactor with leucine-rich repeats |
| 218217_at | 59342 | SCPEP1 | serine carboxypeptidase 1 |
| 205055_at | 3682 | ITGAE | integrin, alpha E (antigen CD103, human mucosal lymphocyte antigen 1; alpha polypeptide |

TABLE 1-continued

| Probeset ID | Entrez Gene | Gene Symbol | Gene Title |
| --- | --- | --- | --- |
| 215009_s_at | 100499177 | THAP9-AS1 | THAP9 antisense RNA 1 (non-protein coding) |
| 227484_at | 57522 | SRGAP1 | SLIT-ROBO Rho GTPase activating protein 1 |
| 239769_at | 1009 | CDH11 | Cadherin 11, type 2, OB-cadherin (osteoblast) |
| 230360_at | 342035 | GLDN | gliomedin |
| 227112_at | 23023 | TMCC1 | transmembrane and coiled-coil domain family 1 |
| 201482_at | 5768 | QSOX1 | quiescin Q6 sulfhydryl oxidase 1 |
| 210337_s_at | 47 | ACLY | ATP citrate lyase |
| 203911_at | 5909 | RAP1GAP | RAP1 GTPase activating protein |
| 206683_at | 7718 | ZNF165 | zinc finger protein 165 |
| 202935_s_at | 6662 | SOX9 | SRY (sex determining region Y)-box 9 |
| 218951_s_at | 55344 | PLCXD1 | phosphatidylinositol-specific phospholipase C, X domain containing 1 |
| 233488_at | 84659 | RNASE7 | ribonuclease, RNase A family, 7 |
| 202562_s_at | 11161 | C14orf1 | chromosome 14 open reading frame 1 |
| 208745_at | 10632 | ATP5L | ATP synthase, H+ transporting, mitochondrial Fo complex, subunit G |
| 236078_at | 57707 | KIAA1609 | KIAA1609 |
| 226226_at | 120224 | TMEM45B | transmembrane protein 45B |
| 213854_at | 9145 | SYNGR1 | synaptogyrin 1 |
| 243955_at | — | — | — |
| 222111_at | 54629 | FAM63B | family with sequence similarity 63, member B |
| 1560296_at | — | — | — |
| 240038_at | — | — | — |
| 211372_s_at | 7850 | IL1R2 | interleukin 1 receptor, type II |
| 202672_s_at | 467 | ATF3 | activating transcription factor 3 |
| 218717_s_at | 55214 | LEPREL1 | leprecan-like 1 |
| 228366_at | — | — | — |
| 230516_at | 115416 | MALSU1 | Mitochondrial assembly of ribosomal large subunit 1 |
| 201920_at | 6574 | SLC20A1 | solute carrier family 20 (phosphate transporter), member 1 |
| 209632_at | 5523 | PPP2R3A | protein phosphatase 2, regulatory subunit B", alpha |
| 207367_at | 479 | ATP12A | ATPase, H+/K+ transporting, nongastric, alpha polypeptide |
| 1557256_a_at | — | — | — |
| 200811_at | 1153 | CIRBP | cold inducible RNA binding protein |
| 205201_at | 2737 | GLI3 | GLI family zinc finger 3 |
| 227724_at | 728190 | LOC728190 | uncharacterized LOC728190 |
| 205403_at | 7850 | IL1R2 | interleukin 1 receptor, type II |
| 242827_x_at | — | — | — |
| 228084_at | 81579 | PLA2G12A | phospholipase A2, group XIIA |
| 209365_s_at | 1893 | ECM1 | extracellular matrix protein 1 |
| 243279_at | — | — | — |
| 224946_s_at | 84317 | CCDC115 | coiled-coil domain containing 115 |
| 218708_at | 29107 | NXT1 | NTF2-like export factor 1 |
| 1560531_at | 353132 | LCE1B | late cornified envelope 1B |
| 207761_s_at | 25840 | METTL7A | methyltransferase like 7A |
| 206011_at | 834 | CASP1 | caspase 1, apoptosis-related cysteine peptidase |
| 213703_at | 150759 | LINC00342 | long intergenic non-protein coding RNA 342 |
| 224595_at | 23446 | SLC44A1 | solute carrier family 44, member 1 |
| 224613_s_at | 80331 | DNAJC5 | DnaJ (Hsp40) homolog, subfamily C, member 5 |
| 212504_at | 22982 | DIP2C | DIP2 disco-interacting protein 2 homolog C (Drosophila) |
| 213682_at | 10762 | NUP50 | nucleoporin 50 kDa |
| 205247_at | 4855 | NOTCH4 | notch 4 |
| 228235_at | 84848 | MGC16121 | uncharacterized protein MGC16121 |
| 242873_at | — | — | — |

TABLE 1-continued

| Probeset ID | Entrez Gene | Gene Symbol | Gene Title |
|---|---|---|---|
| 205960_at | 5166 | PDK4 | pyruvate dehydrogenase kinase, isozyme 4 |
| 230494_at | 6574 | SLC20A1 | solute carrier family 20 (phosphate transporter), member 1 |
| 221260_s_at | 81566 | CSRNP2 | cysteine-serine-rich nuclear protein 2 |
| 224480_s_at | 84803 | AGPAT9 | 1-acylglycerol-3-phosphate O-acyltransferase 9 |
| 210180_s_at | 6434 | TRA2B | transformer 2 beta homolog (*Drosophila*) |
| 204621_s_at | 4929 | NR4A2 | nuclear receptor subfamily 4, group A, member 2 |
| 217863_at | 8554 | PIAS1 | protein inhibitor of activated STAT, 1 |
| 236423_at | — | — | |
| 223421_at | 50626 | CYHR1 | cysteine/histidine-rich 1 |
| 220272_at | 54796 | BNC2 | basonuclin 2 |
| 201791_s_at | 1717 | DHCR7 | 7-dehydrocholesterol reductase |
| 215574_at | — | — | |
| 224328_s_at | 84648 | LCE3D | late cornified envelope 3D |
| 211828_s_at | 23043 | TNIK | TRAF2 and NCK interacting kinase |
| 58367_s_at | 79744 | ZNF419 | zinc finger protein 419 |
| 218950_at | 64411 | ARAP3 | ArfGAP with RhoGAP domain, ankyrin repeat and PH domain 3 |
| 1552703_s_at | 114769 /// 834 | CARD16 /// CASP1 | caspase recruitment domain family, member 16 /// caspase 1, apoptosis-related cysteine |
| 219687_at | 55733 | HHAT | hedgehog acyltransferase |
| 232127_at | 1184 | CLCN5 | chloride channel, voltage-sensitive 5 |
| 218377_s_at | 10069 | RWDD2B | RWD domain containing 2B |
| 210335_at | 9182 | RASSF9 | Ras association (RalGDS/AF-6) domain family (N-terminal) member 9 |
| 227927_at | — | — | |
| 227224_at | 55103 | RALGPS2 | Ral GEF with PH domain and SH3 binding motif 2 |
| 224778_s_at | 57551 | TAOK1 | TAO kinase 1 |
| 229566_at | 645638 | LOC645638 | WDNM1-like pseudogene |
| 202734_at | 9322 | TRIP10 | thyroid hormone receptor interactor 10 |
| 201851_at | 6455 | SH3GL1 | SH3-domain GRB2-like 1 |
| 237337_at | — | — | |
| 37152_at | 5467 | PPARD | peroxisome proliferator-activated receptor delta |
| 209687_at | 6387 | CXCL12 | chemokine (C-X-C motif) ligand 12 |
| 203152_at | 64976 | MRPL40 | mitochondrial ribosomal protein L40 |
| 201627_s_at | 3638 | INSIG1 | insulin induced gene 1 |
| 232593_at | 93082 | NEURL3 | neuralized homolog 3 (*Drosophila*) pseudogene |
| 224769_at | 57551 | TAOK1 | TAO kinase 1 |
| 209702_at | 79068 | FTO | fat mass and obesity associated |
| 204546_at | 9764 | KIAA0513 | KIAA0513 |
| 232224_at | 5648 | MASP1 | mannan-binding lectin serine peptidase 1 (C4/C2 activating component of Ra-reactive fac |
| 239930_at | 2590 | GALNT2 | UDP-N-acetyl-alpha-D-galactosamine:polypeptide N-acetylgalactosaminyltransferase 2 (Gal |
| 203178_at | 2628 | GATM | glycine amidinotransferase (L-arginine:glycine amidinotransferase) |
| 235782_at | — | — | |
| 218181_s_at | 9448 | MAP4K4 | mitogen-activated protein kinase kinase kinase kinase 4 |
| 233520_s_at | 202333 | CMYA5 | cardiomyopathy associated 5 |
| 213456_at | 25928 | SOSTDC1 | sclerostin domain containing 1 |
| 219528_s_at | 64919 | BCL11B | B-cell CLL/lymphoma 11B (zinc finger protein) |
| 224945_at | 55727 | BTBD7 | BTB (POZ) domain containing 7 |

TABLE 1-continued

| Probeset ID | Entrez Gene | Gene Symbol | Gene Title |
|---|---|---|---|
| 214866_at | 5329 | PLAUR | plasminogen activator, urokinase receptor |
| 209941_at | 8737 | RIPK1 | receptor (TNFRSF)-interacting serine-threonine kinase 1 |
| 226029_at | 57216 | VANGL2 | vang-like 2 (van gogh, *Drosophila*) |
| 212596_s_at | 10042 | HMGXB4 | HMG box domain containing 4 |
| 229873_at | 283219 | KCTD21 | potassium channel tetramerisation domain containing 21 |
| 226392_at | 5922 | RASA2 | RAS p21 protein activator 2 |
| 226005_at | 7326 | UBE2G1 | ubiquitin-conjugating enzyme E2G 1 |
| 214445_at | 22936 | ELL2 | elongation factor, RNA polymerase II, 2 |
| 227680_at | 284695 | ZNF326 | zinc finger protein 326 |
| 227786_at | 90390 | MED30 | mediator complex subunit 30 |
| 222067_x_at | 3017 | HIST1H2BD | histone cluster 1, H2bd |
| 1569106_s_at | 55209 | SETD5 | SET domain containing 5 |
| 231785_at | 4909 | NTF4 | neurotrophin 4 |
| 223937_at | 27086 | FOXP1 | forkhead box P1 |
| 1558685_a_at | 158960 | LOC158960 | uncharacterized protein BC009467 |
| 211965_at | 677 | ZFP36L1 | zinc finger protein 36, C3H type-like 1 |
| 39549_at | 4862 | NPAS2 | neuronal PAS domain protein 2 |
| 203800_s_at | 63931 | MRPS14 | mitochondrial ribosomal protein S14 |
| 1556321_a_at | — | — | — |
| 212321_at | 8879 | SGPL1 | sphingosine-1-phosphate lyase 1 |
| 222154_s_at | 26010 | SPATS2L | spermatogenesis associated, serine-rich 2-like |
| 218774_at | 28960 | DCPS | decapping enzyme, scavenger |
| 212268_at | 1992 | SERPINB1 | serpin peptidase inhibitor, clade B (ovalbumin), member 1 |
| 213134_x_at | 10950 | BTG3 | BTG family, member 3 |
| 230669_at | 5922 | RASA2 | RAS p21 protein activator 2 |
| 1559901_s_at | 388815 | LINC00478 | long intergenic non-protein coding RNA 478 |
| 225298_at | 25953 | PNKD | paroxysmal nonkinesigenic dyskinesia |
| 242558_at | — | — | — |
| 226043_at | 26086 | GPSM1 | G-protein signaling modulator 1 |
| 210236_at | 8500 | PPFIA1 | protein tyrosine phosphatase, receptor type, f polypeptide (PTPRF), interacting protein |
| 214066_x_at | 4882 | NPR2 | natriuretic peptide receptor B/guanylate cyclase B (atrionatriuretic peptide receptor B |
| 240024_at | 23541 | SEC14L2 | SEC14-like 2 (*S. cerevisiae*) |
| 235462_at | 132864 | CPEB2 | Cytoplasmic polyadenylation element binding protein 2 |
| 1554015_a_at | 1106 | CHD2 | chromodomain helicase DNA binding protein 2 |
| 235347_at | 84859 | LRCH3 | leucine-rich repeats and calponin homology (CH) domain containing 3 |
| 230847_at | 56897 | WRNIP1 | Werner helicase interacting protein 1 |
| 201427_s_at | 6414 | SEPP1 | selenoprotein P, plasma, 1 |
| 1557905_s_at | 960 | CD44 | CD44 molecule (Indian blood group) |
| 219084_at | 64324 | NSD1 | nuclear receptor binding SET domain protein 1 |
| 206176_at | 654 | BMP6 | bone morphogenetic protein 6 |
| 219826_at | 79744 | ZNF419 | zinc finger protein 419 |
| 212356_at | 23351 | KHNYN | KH and NYN domain containing |
| 218909_at | 26750 | RPS6KC1 | ribosomal protein S6 kinase, 52 kDa, polypeptide 1 |
| 230555_s_at | 90390 | MED30 | Mediator complex subunit 30 |
| 212687_at | 3987 | LIMS1 | LIM and senescent cell antigen-like domains 1 |
| 203098_at | 9425 | CDYL | chromodomain protein, Y-like |

TABLE 1-continued

| Probeset ID | Entrez Gene | Gene Symbol | Gene Title |
|---|---|---|---|
| 229054_at | 677 | ZFP36L1 | zinc finger protein 36, C3H type-like 1 |
| 236039_at | 284348 | LYPD5 | LY6/PLAUR domain containing 5 |
| 209661_at | 3801 | KIFC3 | kinesin family member C3 |
| 209560_s_at | 8788 | DLK1 | delta-like 1 homolog (*Drosophila*) |
| 225812_at | 619208 | C6orf225 | chromosome 6 open reading frame 225 |
| 227829_at | 120071 | GYLTL1B | glycosyltransferase-like 1B |
| 238623_at | — | — | — |
| 229415_at | 54205 | CYCS | cytochrome c, somatic |
| 209222_s_at | 9885 | OSBPL2 | oxysterol binding protein-like 2 |
| 1555809_at | 83716 | CRISPLD2 | cysteine-rich secretory protein LCCL domain containing 2 |
| 204567_s_at | 9619 | ABCG1 | ATP-binding cassette, sub-family G (WHITE), member 1 |
| 232277_at | 64078 | SLC28A3 | solute carrier family 28 (sodium-coupled nucleoside transporter), member 3 |
| 237197_at | — | — | — |
| 225209_s_at | 118424 | UBE2J2 | ubiquitin-conjugating enzyme E2, J2 |
| 231916_at | 4842 | NOS1 | nitric oxide synthase 1 (neuronal) |
| 212279_at | 27346 | TMEM97 | transmembrane protein 97 |
| 204862_s_at | 4832 | NME3 | NME/NM23 nucleoside diphosphate kinase 3 |
| 230483_at | — | — | — |
| 212856_at | 23151 | GRAMD4 | GRAM domain containing 4 |
| 224650_at | 114569 | MAL2 | mal, T-cell differentiation protein 2 (gene/pseudogene) |
| 202963_at | 5993 | RFX5 | regulatory factor X, 5 (influences HLA class II expression) |
| 225320_at | 90550 | MCU | mitochondrial calcium uniporter |
| 236274_at | 8662 | EIF3B | eukaryotic translation initiation factor 3, subunit B |
| 209780_at | 57157 | PHTF2 | putative homeodomain transcription factor 2 |
| 218823_s_at | 54793 | KCTD9 | potassium channel tetramerisation domain containing 9 |
| 227787_s_at | 90390 | MED30 | mediator complex subunit 30 |
| 230296_at | 730094 | C16orf52 | chromosome 16 open reading frame 52 |
| 222892_s_at | 55287 | TMEM40 | transmembrane protein 40 |
| 210610_at | 634 | CEACAM1 | carcinoembryonic antigen-related cell adhesion molecule 1 (biliary glycoprotein) |
| 230031_at | 3309 | HSPA5 | heat shock 70 kDa protein 5 (glucose-regulated protein, 78 kDa) |
| 238477_at | 10749 | KIF1C | kinesin family member 1C |
| 209409_at | 2887 | GRB10 | growth factor receptor-bound protein 10 |
| 217995_at | 58472 | SQRDL | sulfide quinone reductase-like (yeast) |
| 226873_at | 54629 | FAM63B | family with sequence similarity 63, member B |
| 1553722_s_at | 220441 | RNF152 | ring finger protein 152 |
| 204710_s_at | 26100 | WIPI2 | WD repeat domain, phosphoinositide interacting 2 |
| 212653_s_at | 23301 | EHBP1 | EH domain binding protein 1 |
| 203979_at | 1593 | CYP27A1 | cytochrome P450, family 27, subfamily A, polypeptide 1 |
| 244350_at | 4651 | MYO10 | myosin X |
| 223233_s_at | 57530 | CGN | cingulin |
| 1555967_at | — | — | — |
| 214355_x_at | 100128553 /// 100142659 /// 340307 /// 441294 /// 643854 | CTAGE15P /// CTAGE4 /// CTAGE6P /// CTAGE8 /// CTAGE9 | CTAGE family, member 15, pseudogene /// CTAGE family, member 4 /// CTAGE family, member |
| 214469_at | 3012 /// 8335 | HIST1H2AB /// HIST1H2AE | histone cluster 1, H2ab /// histone cluster 1, H2ae |

TABLE 1-continued

| Probeset ID | Entrez Gene | Gene Symbol | Gene Title |
|---|---|---|---|
| 212472_at | 9645 | MICAL2 | microtubule associated monoxygenase, calponin and LIM domain containing 2 |
| 228115_at | 64762 | FAM59A | family with sequence similarity 59, member A |
| 228964_at | 639 | PRDM1 | PR domain containing 1, with ZNF domain |
| 230027_s_at | 84545 | MRPL43 | mitochondrial ribosomal protein L43 |
| 207318_s_at | 8621 | CDK13 | cyclin-dependent kinase 13 |
| 221689_s_at | 51227 | PIGP | phosphatidylinositol glycan anchor biosynthesis, class P |
| 219270_at | 79094 | CHAC1 | ChaC, cation transport regulator homolog 1 (*E. coli*) |
| 225299_at | 4645 | MYO5B | myosin VB |
| 239770_at | 83850 | ESYT3 | extended synaptotagmin-like protein 3 |
| 226399_at | 79982 | DNAJB14 | DnaJ (Hsp40) homolog, subfamily B, member 14 |
| 226656_at | 10491 | CRTAP | cartilage associated protein |
| 228852_at | 2029 | ENSA | endosulfine alpha |
| 206239_s_at | 6690 | SPINK1 | serine peptidase inhibitor, Kazal type 1 |
| 210993_s_at | 4086 | SMAD1 | SMAD family member 1 |
| 238462_at | 84959 | UBASH3B | ubiquitin associated and SH3 domain containing B |
| 211962_s_at | 677 | ZFP36L1 | zinc finger protein 36, C3H type-like 1 |
| 224666_at | 197370 | NSMCE1 | non-SMC element 1 homoiog (*S. cerevisiae*) |
| 239028_at | 130574 | LYPD6 | LY6/PLAUR domain containing 6 |
| 213577_at | 6713 | SQLE | squalene epoxidase |
| 202011_at | 7082 | TJP1 | tight junction protein 1 (zona occludens 1) |
| 212254_s_at | 100652766 /// 667 | DST /// LOC100652766 | dystonin /// dystonin-like |
| 221701_s_at | 64220 | STRA6 | stimulated by retinoic acid gene 6 homolog (mouse) |
| 239576_at | 57509 | MTUS1 | microtubule associated tumor suppressor 1 |
| 234418_x_at | 960 | CD44 | CD44 molecule (Indian blood group) |
| 227985_at | 100506098 | LOC100506098 | uncharacterized LOC100506098 |
| 213462_at | 4862 | NPAS2 | neuronal PAS domain protein 2 |
| 224975_at | 4774 | NFIA | nuclear factor I/A |
| 225990_at | 91653 | BOC | Boc homolog (mouse) |
| 240616_at | — | — | — |
| 219911_s_at | 28231 | SLCO4A1 | solute carrier organic anion transporter family, member 4A1 |
| 224970_at | 4774 | NFIA | nuclear factor I/A |
| 214623_at | 26226 | FBXW4P1 | F-box and WD repeat domain containing 4 pseudogene 1 |
| 239478_x_at | 55668 | C14orf118 | chromosome 14 open reading frame 118 |
| 226909_at | 85460 | ZNF518B | zinc finger protein 518B |
| 208670_s_at | 23741 | EID1 | EP300 interacting inhibitor of differentiation 1 |
| 206192_at | 1041 | CDSN | corneodesmosin |
| 222173_s_at | 55357 | TBC1D2 | TBC1 domain family, member 2 |
| 228450_at | 144100 | PLEKHA7 | pleckstrin homology domain containing, family A member 7 |
| 1558097_at | 253143 | PRR14L | proline rich 14-like |
| 219373_at | 54344 | DPM3 | dolichyl-phosphate mannosyltransferase polypeptide 3 |
| 230388_s_at | 644246 | KANSL1-AS1 | KANSL1 antisense RNA 1 (non-protein coding) |
| 207098_s_at | 55669 | MFN1 | mitofusin 1 |
| 223484_at | 84419 | C15orf48 | chromosome 15 open reading frame 48 |
| 244804_at | 8878 | SQSTM1 | sequestosome 1 |
| 229679_at | 400073 | C12orf76 | chromosome 12 open reading frame 76 |
| 225826_at | 326625 | MMAB | methylmalonic aciduria (cobalamin deficiency) cbIB type |

TABLE 1-continued

| Probeset ID | Entrez Gene | Gene Symbol | Gene Title |
|---|---|---|---|
| 213352_at | 23023 | TMCC1 | transmembrane and coiled-coil domain family 1 |
| 211883_x_at | 634 | CEACAM1 | carcinoembryonic antigen-related cell adhesion molecule 1 (biliary glycoprotein) |
| 210387_at | 8339 /// 8343 /// 8344 /// 8346 /// 8347 | HIST1H2BC /// HIST1H2BE /// HIST1H2BF /// HIST1H2BG /// HIST1H2BI | histone cluster 1, H2bc /// histone cluster 1, H2be /// histone cluster 1, H2bf /// his |
| 210916_s_at | 960 | CD44 | CD44 molecule (Indian blood group) |
| 221432_s_at | 81894 | SLC25A28 | solute carrier family 25 (mitochondrial iron transporter), member 28 |
| 218487_at | 210 | ALAD | aminolevulinate dehydratase |
| 223264_at | 59274 | MESDC1 | mesoderm development candidate 1 |
| 206356_s_at | 2774 | GNAL | guanine nucleotide binding protein (G protein), alpha activating activity polypeptide, |
| 218097_s_at | 79004 | CUEDC2 | CUE domain containing 2 |
| 228001_at | 757 | TMEM50B | transmembrane protein 50B |
| 212441_at | 9778 | KIAA0232 | KIAA0232 |
| 201854_s_at | 23300 | ATMIN | ATM interactor |
| 121_at | 7849 | PAX8 | paired box 8 |
| 222143_s_at | 64419 | MTMR14 | myotubularin related protein 14 |
| 1558002_at | 11171 | STRAP | Serine/threonine kinase receptor associated protein |
| 226040_at | — | — | — |
| 226141_at | 91050 | CCDC149 | coiled-coil domain containing 149 |
| 1556567_at | 4676 | NAP1L4 | nucleosome assembly protein 1-like 4 |
| 226263_at | 154007 | SNRNP48 | small nuclear ribonucleoprotein 48 kDa (U11/U12) |
| 212074_at | 23353 | SUN1 | Sad1 and UNC84 domain containing 1 |
| 227387_at | 54780 | NSMCE4A | Non-SMC element 4 homolog A (S. cerevisiae) |
| 232795_at | — | — | — |
| 203936_s_at | 4318 | MMP9 | matrix metallopeptidase 9 (gelatinase B, 92 kDa gelatinase, 92 kDa type IV collagenase) |
| 225033_at | 6482 | ST3GAL1 | ST3 beta-galactoside alpha-2,3-sialyltransferase 1 |
| 209109_s_at | 7105 | TSPAN6 | tetraspanin 6 |
| 213351_s_at | 23023 | TMCC1 | transmembrane and coiled-coil domain family 1 |
| 203047_at | 6793 | STK10 | serine/threonine kinase 10 |
| 220721_at | 80110 | ZNF614 | zinc finger protein 614 |
| 1556127_at | 23181 | DIP2A | DIP2 disco-interacting protein 2 homolog A (Drosophila) |
| 215016_x_at | 100652766 /// 667 | DST /// LOC100652766 | dystonin /// dystonin-like |
| 206576_s_at | 634 | CEACAM1 | carcinoembryonic antigen-related cell adhesion molecule 1 (biliary glycoprotein) |
| 240674_at | 3720 | JARID2 | jumonji, AT rich interactive domain 2 |
| 225646_at | 1075 | CTSC | cathepsin C |
| 1554010_at | 3340 | NDST1 | N-deacetylase/N-sulfotransferase (heparan glucosaminyl) 1 |
| 204100_at | 7067 | THRA | thyroid hormone receptor, alpha |
| 221840_at | 5791 | PTPRE | protein tyrosine phosphatase, receptor type, E |
| 209078_s_at | 25828 | TXN2 | thioredoxin 2 |
| 218530_at | 29109 | FHOD1 | formin homology 2 domain containing 1 |
| 235434_at | — | — | — |
| 230063_at | 9422 | ZNF264 | zinc finger protein 264 |
| 40420_at | 6793 | STK10 | serine/threonine kinase 10 |
| 221027_s_at | 81579 | PLA2G12A | phospholipase A2, group XIIA |
| 244202_at | — | — | — |
| 212108_at | 23197 | FAF2 | Fas associated factor family member 2 |

TABLE 1-continued

| Probeset ID | Entrez Gene | Gene Symbol | Gene Title |
|---|---|---|---|
| 204294_at | 275 | AMT | aminomethyltransferase |
| 225503_at | 207063 | DHRSX | dehydrogenase/reductase (SDR family) X-linked |
| 212810_s_at | 6509 | SLC1A4 | solute carrier family 1 (glutamate/neutral amino acid transporter), member 4 |
| 214814_at | 91746 | YTHDC1 | YTH domain containing 1 |
| 228468_at | 84930 | MASTL | microtubule associated serine/threonine kinase-like |
| 209108_at | 7105 | TSPAN6 | tetraspanin 6 |
| 220444_at | 79230 | ZNF557 | zinc finger protein 557 |
| 206172_at | 3598 | IL13RA2 | interleukin 13 receptor, alpha 2 |
| 225002_s_at | 25870 | SUMF2 | sulfatase modifying factor 2 |
| 212205_at | 94239 | H2AFV | H2A histone family, member V |
| 228851_s_at | 2029 | ENSA | endosulfine alpha |
| 209048_s_at | 23613 | ZMYND8 | zinc finger, MYND-type containing 8 |
| 211846_s_at | 5818 | PVRL1 | poliovirus receptor-related 1 (herpesvirus entry mediator C) |
| 238909_at | 6281 | S100A10 | S100 calcium binding protein A10 |
| 205503_at | 5784 | PTPN14 | protein tyrosine phosphatase, non-receptor type 14 |
| 243829_at | 673 | BRAF | v-raf murine sarcoma viral oncogene homolog B1 |
| 244379_at | — | — | — |
| 223251_s_at | 55608 | ANKRD10 | ankyrin repeat domain 10 |
| 202633_at | 11073 | TOPBP1 | topoisomerase (DNA) II binding protein 1 |
| 214502_at | 8970 | HIST1H2BJ | histone cluster 1, H2bj |
| 221773_at | 2004 | ELK3 | ELK3, ETS-domain protein (SRF accessory protein 2) |
| 41858_at | 27315 | PGAP2 | post-GPI attachment to proteins 2 |
| 212850_s_at | 4038 | LRP4 | low density lipoprotein receptor-related protein 4 |
| 223408_s_at | — | — | — |
| 214472_at | 3013 /// 8350 /// 8351 /// 8352 /// 8353 /// 8354 /// 8355 /// 8356 /// 8357 /// 8358 / | HIST1H2AD /// HIST1H3A /// HIST1H3B /// HIST1H3C /// HIST1H3D /// HIST1H3E /// HIST1H3F /// HIST1H3G /// HIST1H3H /// HIST1H3I /// HIST1H3J | histone cluster 1, H2ad /// histone cluster 1, H3a /// histone cluster 1, H3b /// histo |
| 225647_s_at | 1075 | CTSC | cathepsin C |
| 1559977_a_at | 284723 | SLC25A34 | solute carrier family 25, member 34 |
| 211347_at | 8555 | CDC14B | CDC14 cell division cycle 14 homolog B (S. cerevisiae) |
| 1558208_at | — | — | — |
| 227570_at | 144110 | TMEM86A | transmembrane protein 86A |
| 227492_at | 100506658 /// 647859 | LOC647859 /// OCLN | occludin pseudogene /// occludin |
| 1558778_s_at | 57496 | MKL2 | MKL/myocardin-like 2 |
| 31637_s_at | 7067 /// 9572 | NR1D1 /// THRA | nuclear receptor subfamily 1, group D, member 1 /// thyroid hormone receptor, alpha |
| 229190_at | 100507376 | LOC100507376 | uncharacterized LOC100507376 |
| 236188_s_at | 4676 | NAP1L4 | Nucleosome assembly protein 1-like 4 |
| 212503_s_at | 22982 | DIP2C | DIP2 disco-interacting protein 2 homolog C (Drosophila) |
| 204760_s_at | 7067 /// 9572 | NR1D1 /// THRA | nuclear receptor subfamily 1, group D, member 1 /// thyroid hormone receptor, alpha |
| 212099_at | 388 | RHOB | ras homolog family member B |
| 214873_at | 91355 | LRP5L | low density lipoprotein receptor-related protein 5-like |
| 228181_at | 7779 | SLC30A1 | solute carrier family 30 (zinc transporter), member 1 |
| 212763_at | 23271 | CAMSAP2 | calmodulin regulated spectrin-associated protein family, member 2 |

TABLE 1-continued

| Probeset ID | Entrez Gene | Gene Symbol | Gene Title |
|---|---|---|---|
| 226285_at | 4076 | CAPRIN1 | cell cycle associated protein 1 |
| 213567_at | 3840 | KPNA4 | karyopherin alpha 4 (importin alpha 3) |
| 203927_at | 4794 | NFKBIE | nuclear factor of kappa light polypeptide gene enhancer in B-cells inhibitor, epsilon |
| 208523_x_at | 8339 /// 8343 /// 8344 /// 8346 /// 8347 | HIST1H2BC /// HIST1H2BE /// HIST1H2BF /// HIST1H2BG /// HIST1H2BI | histone cluster 1, H2bc /// histone cluster 1, H2be /// histone cluster 1, H2bf /// his |
| 219389_at | 55061 | SUSD4 | sushi domain containing 4 |
| 202329_at | 1445 | CSK | c-src tyrosine kinase |
| 238523_at | 79786 | KLHL36 | kelch-like 36 (*Drosophila*) |
| 1565016_at | 3276 | PRMT1 | protein arginine methyltransferase 1 |
| 226409_at | 128637 | TBC1D20 | TBC1 domain family, member 20 |
| 229926_at | 100500850 | MIR3682 | microRNA 3682 |
| 208527_x_at | 8339 /// 8343 /// 8344 /// 8346 /// 8347 | HIST1H2BC /// HIST1H2BE /// HIST1H2BF /// HIST1H2BG /// HIST1H2BI | histone cluster 1, H2bc /// histone cluster 1, H2be /// histone cluster 1, H2bf /// his |
| 223598_at | 5887 | RAD23B | RAD23 homolog B (*S. cerevisiae*) |
| 243797_at | 9262 | STK17B | serine/threonine kinase 17b |
| 203317_at | 23550 | PSD4 | pleckstrin and Sec7 domain containing 4 |
| 230965_at | 9099 | USP2 | ubiquitin specific peptidase 2 |
| 208490_x_at | 8339 /// 8343 /// 8344 /// 8346 /// 8347 | HIST1H2BC /// HIST1H2BE /// HIST1H2BF /// HIST1H2BG /// HIST1H2BI | histone cluster 1, H2bc /// histone cluster 1, H2be /// histone cluster 1, H2bf /// his |
| 235514_at | 151516 | ASPRV1 | aspartic peptidase, retroviral-like 1 |
| 209098_s_at | 182 | JAG1 | jagged 1 |
| 1554229_at | 153222 | CREBRF | CREB3 regulatory factor |
| 209398_at | 3006 | HIST1H1C | histone cluster 1, H1c |
| 202629_at | 10513 | APPBP2 | amyloid beta precursor protein (cytoplasmic tail) binding protein 2 |
| 203428_s_at | 25842 | ASF1A | ASF1 anti-silencing function 1 homolog A (*S. cerevisiae*) |
| 238005_s_at | 25942 | SIN3A | SIN3 transcription regulator homolog A (yeast) |
| 214455_at | 8339 /// 8343 /// 8344 /// 8346 /// 8347 | HIST1H2BC /// HIST1H2BE /// HIST1H2BF /// HIST1H2BG /// HIST1H2BI | histone cluster 1, H2bc /// histone cluster 1, H2be /// histone cluster 1, H2bf /// his |
| 214073_at | 2017 | CTTN | cortactin |
| 203140_at | 604 | BCL6 | B-cell CLL/lymphoma 6 |
| 232150_at | — | — | — |
| 208546_x_at | 8345 | HIST1H2BH | histone cluster 1, H2bh |
| 243446_at | 84962 | AJUBA | ajuba LIM protein |
| 236207_at | 6744 | SSFA2 | sperm specific antigen 2 |
| 212016_s_at | 5725 | PTBP1 | polypyrimidine tract binding protein 1 |
| 232311_at | 567 | B2M | Beta-2-microglobulin |
| 219711_at | 54807 | ZNF586 | zinc finger protein 586 |
| 208579_x_at | 54145 /// 85236 | H2BFS /// HIST1H2BK | H2B histone family, member S (pseudogene) /// histone cluster 1, H2bk |
| 239493_at | 6129 | RPL7 | ribosomal protein L7 |
| 214074_s_at | 2017 | CTTN | cortactin |
| 228091_at | 55014 | STX17 | syntaxin 17 |
| 234331_s_at | 151354 | FAM84A | family with sequence similarity 84, member A |
| 212372_at | 4628 | MYH10 | myosin, heavy chain 10, non-muscle |

Using the probe list in Table 1, a multivariate analysis of different signatures was conducted using available references to build the following signatures, to analyze the results at different doses of CTO (equivalent to 2 μM, 5 μM, and 10 μM CAI) at 8 hrs and 24 hrs: –RAS signature; Growth factor signature; PI3K/mTOR inhibition; PI3K inhibition; MEK inhibition; HSP90 inhibition; HDAC inhibition: EGFR inhibition; P53 Stabilization; WNT/β-Catenin inhibition; Calcium Signaling; CAI inhibition; canonical calcium inhibition; and Non-voltage signaling.

Figure 2:
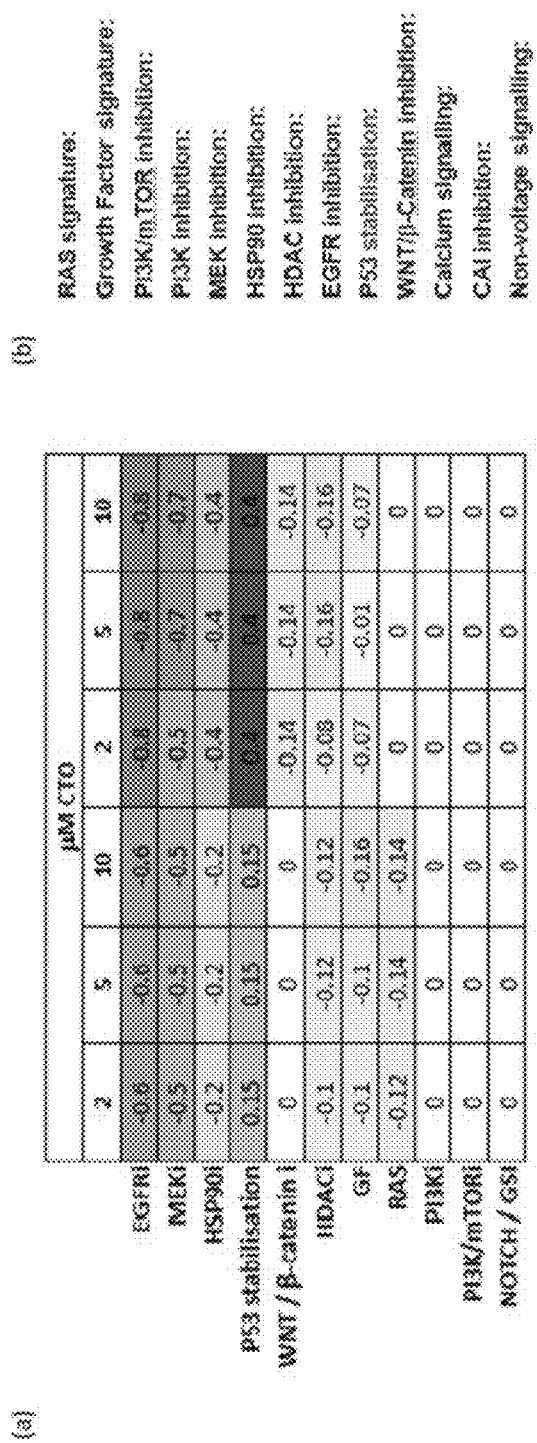

Results obtained for the above analyses are summarized in FIG. 2b in detail. EGFR, MEK and HDAC pathways were strongly suppressed in response to CTO.

In contrast, the pathway associated with P53 was stabilized in response to CTO.

In addition, genes associated with non-voltage dependent calcium signaling, were strongly suppressed. These results are discussed in detail below.

Example 3

Figure 3:
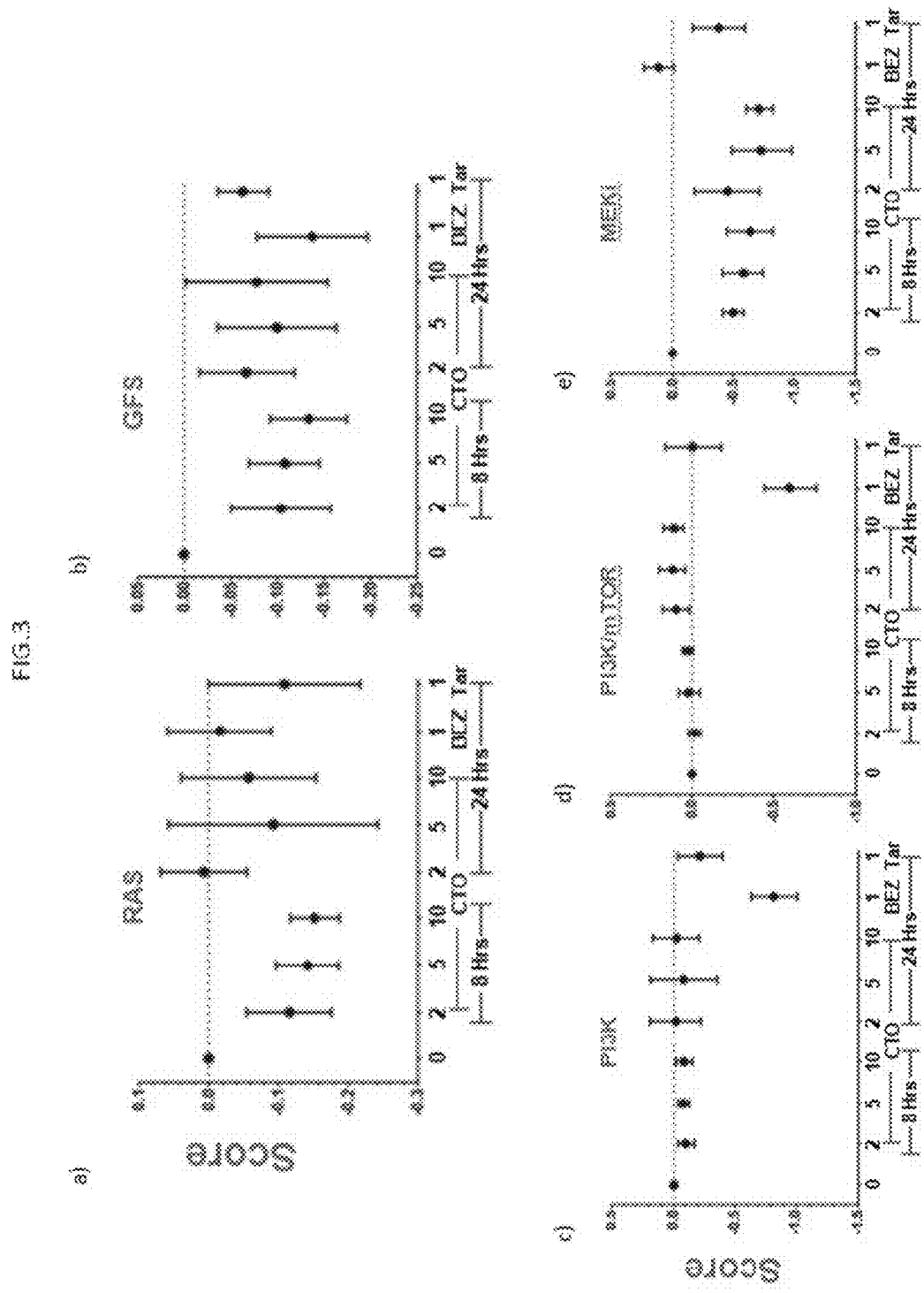
FIG. 3a illustrates the Signature Score for the RAS pathway in response to different doses of CTO at 8 hr and 24 hr compared with BEZ235 and Tarceva® for 24 hr.
FIG. 3b illustrates the Signature Score for the Growth Factor Signature (GFS) pathway in response to different doses of CTO at 8 hr and 24 hr compared with BEZ235 and Tarceva® for 24 hr.
FIG. 3c illustrates the Signature Score for the PI3K pathway in response to different doses of CTO at 8 hr and 24 hr compared with BEZ235 and Tarceva® for 24 hr.
FIG. 3d illustrates the Signature Score for the PI3K/mTOR pathway in response to different doses of CTO at 8 hr and 24 hr compared with BEZ235 and Tarceva® for 24 hr.
FIG. 3e illustrates the Signature Score for the MEK pathway in response to different doses of CTO at 8 hr and 24 hr compared with BEZ235 and Tarceva® for 24 hr.

FIG. 3a describes results of multivariate signatures for RAS and Growth Factor Signatures. Briefly, modest down regulation in RAS and Growth Factor signatures (GFS) were observed, the inhibition being most obvious at 8 hrs. Table 2 gives List of RAS and GFS signatures.

NOTCH pathway in response to different doses of CTO at 8 hr and 24 hr is compared with BEZ235 and Tarceva® for 24 hr.

Figure 4:
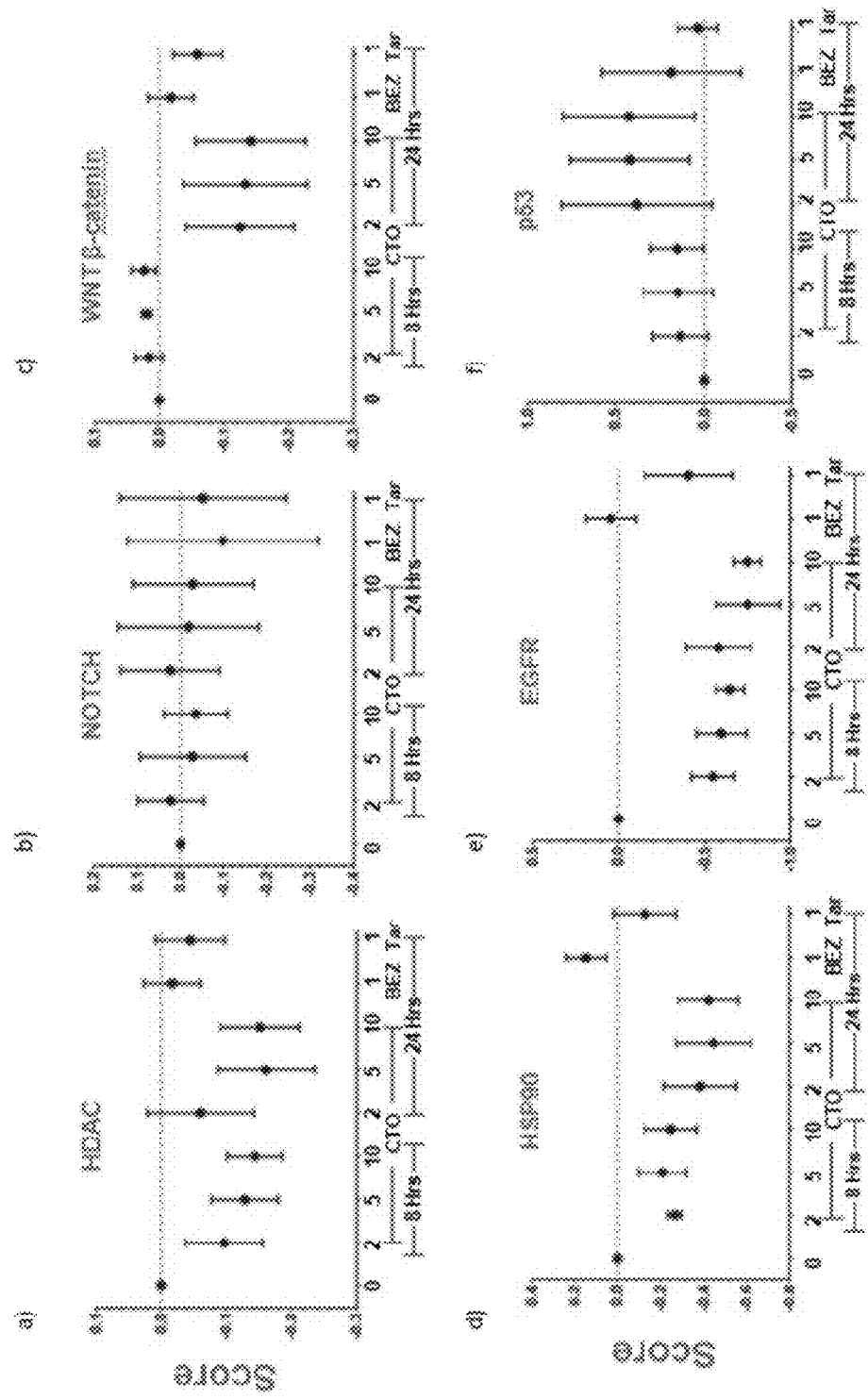
FIG. 4a illustrates the Signature Score for the HDAC pathway in response to different doses of CTO at 8 hr and 24 hr compared with BEZ235 and Tarceva® for 24 hr.
FIG. 4b illustrates the Signature Score for the NOTCH pathway in response to different doses of CTO at 8 hr and 24 hr compared with BEZ235 and Tarceva® for 24 hr.
FIG. 4c illustrates the Signature Score for the WNT β-catenin pathway in response to different doses of CTO at 8 hr and 24 hr compared with BEZ235 and Tarceva®, for 24 hr.
FIG. 4d illustrates the Signature Score for the HSP90 pathway in response to different doses of CTO at 8 hr and 24 hr compared with BEZ235 and Tarceva® for 24 hr.
FIG. 4e illustrates the Signature Score for the EGFR pathway in response to different doses of CTO at 8 hr and 24 hr compared with BEZ235 and Tarceva® for 24 hr.
FIG. 4f illustrates the Signature Score for the P53 pathway in response to different doses of CTO at 8 hr and 24 hr compared with BEZ235 and Tarceva® for 24 hr.

FIG. 4c describes results showing WNT β-catenin signature shows modes suppression in 24 hrs exposure to CTO. The Signature Score for the WNT β-catenin pathway in response to different doses of CTO at 8 hr and 24 hr is compared with BEZ235 and Tarceva® for 24 hr.

FIG. 4d describes strong suppression of HSP90 signature with CTO treatment which is dose dependent. The Signature Score for the HSP90 pathway in response to different doses of CTO at 8 hr and 24 hr is compared with BEZ235 and Tarceva® for 24 hr.

FIG. 4e describes very strong suppression of EGFR signature with CTO treatment and importantly this is stronger than that in Tarceva® at all doses of CTO and time points. The Signature Score for the EGFR pathway in response to different doses of CTO at 8 hr and 24 hr is compared with BEZ235 and Tarceva® for 24 hr FIG. 4f describes induction of P53 signature with CTO treatment at all doses which is higher at the 24 hr time point. The Signature Score for the P53 pathway in response to different doses of CTO at 8 hr and 24 hr is compared with BEZ235 and Tarceva® for 24 hr.

TABLE 2

| GFS And RAS: Symbol | | | | | | |
|---|---|---|---|---|---|---|
| ABCC5 | CYHR1 | HIST3H2A | POU2F3 | CORO1C | IFRD1 | PFKP |
| ATP6V1B1 | DEPTOR | HOXB13 | RAMP1 | DLEU2 | IMPAD1 | PNPT1 |
| ATXN3 | DNAL4 | ING4 | SEMA3G | DPH3 | KLK6 | PSMC4 |
| BCAS1 | EIF4A2 | OVGP1 | SEPP1 | EIF5 | KPNA4 | RPS6KA3 |
| BCL2L11 | EPHX2 | PCMTD1 | SIDT2 | ENO2 | LRP8 | S100A2 |
| CALCOCO1 | ERBB3 | PCMTD2 | AREG | HN1 | MALL | SERPINB5 |
| CAPN13 | HIST1H2AC | PDIA4 | BTG3 | HSP90AA1 | MTHFD1L | SERPINB8 |
| CRBN | HIST1H2BD | PLEKHG4 | CEBPG | HSPA4L | PADI1 | SLC7A1 |
| | | | | | | SRXN1 |
| | | | | | | TIPIN |

FIG. 3c describes results on PI3K in response to CTO. Strong suppression of PI3K signature was observed with control BEZ235 treatment but not with CTO.

FIG. 3d describes results on PI3K/mTOR signature. Strong suppression of PI3K/mTOR signature was observed with control BEZ235 treatment but not with CTO.

FIG. 3e describes strong inhibition of MEKi signature in all CTO treatments at 8 hrs and 24 hrs.

Example 4

FIG. 4a gives results showing weak suppression of HDAC signature in response to CTO treatment. The Signature Score for the HDAC pathway in response to different doses of CTO at 8 hr and 24 hr is compared with BEZ235 and Tarceva® for 24 hr.

FIG. 4b describes no suppression of Notch signature in response to CTO treatment. The Signature Score for the Example 5

FIG. 5a illustrates the Signature Score for the CAI IPA pathway in response to different doses of CTO at 8 hr and 24 hr compared with BEZ235 and Tarceva® for 24 hr. Using the Ingenuity Pathways Analysis (IPA) (Ingenuity Systems, Redwood City, Calif.) for genes influenced by CAI, some suppression of CAI signature in response to CTO treatment was observed, except at 10 μM. When the 29 genes were filtered from IPA for FDA<0.05 and 1.5 FC in CTO data set, to select informative genes and determine the direction of change, a 14 gene set resulted.

TABLE 3

| lists the CAI IPA: Symbol | | | | | | | | | |
|---|---|---|---|---|---|---|---|---|---|
| MMP2 | ESR1 | FOS | PCLG2 | MAPK6 | MAP15 | AKT1 | MOS3 | HSP90B1 |
| JUN | CCND1 | PPAR1 | MAPK1 | MAPK7 | CASP3 | AKT2 | HSP90AA1 | Hsp84-2 |
| CEBPA | MAPK3 | PCLG1 | MAPK4 | MAPK12 | HSPA8 | AKT3 | HSP90AB1 | Hsp84-3 |
| | | | | | | | | BAG3 |

FIG. 5b illustrates the Signature Score for the CAI Ex vivo pathway in response to different doses of CTO at 8 hr and 24 hr compared with BEZ235 and Tarceva® for 24 hr. With the tissue specific direction of change information a strong dose dependent suppression of the IPA CAI list was observed. Table 4 lists the 14 gene set.

TABLE 4

| \ | \ | \ | Symbol: | \ | \ | \ |
|---|---|---|---|---|---|---|
| AKT2 | CASP3 | FOS | HSP90AB1 | JUN | CEBPA | MAPK3 |
| BAG3 | CCND1 | HSP90AA1 | HSP90B1 | AKT1 | MAPK1 | MAPK7 |

FIG. 5c illustrates the Signature Score for the Calcium signaling pathway in response to different doses of CTO at 8 hr and 24 hr compared with BEZ235 and Tarceva® for 24 hr. Non-voltage dependent calcium signaling genes were identified from datasets in literature to inform on regulation. The list is presented in Table 5.

TABLE 5

| \ | \ | \ | Symbol: | \ | \ |
|---|---|---|---|---|---|
| ARG2 | CCNA1 | CCND2 | CCNE2 | TNF | CA9 |
| BDNF | CCNA2 | CCNE1 | CTF1 | BRAF | CALR |

FIG. 5d illustrates the Signature Score for the Calcium signaling for all gene pathway in response to different doses of CTO at 8 hr and 24 hr compared with BEZ235 and Tarceva® for 24 hr. The estimated regulation direction for all genes was identified. The list is provided in Table 6.

TABLE 6

| \ | \ | \ | \ | \ | Symbol: | \ | \ | \ | \ | \ |
|---|---|---|---|---|---|---|---|---|---|---|
| ARG2 | CCND2 | TNF | PPP3R1 | CALM3 | CAMK2A | CAMK4 | ORAI3 | TRPC3 | TRPC7 |
| BDNF | CCNE1 | PPP3CA | PPP3R2 | CAMK1 | CAMK2B | NOS2 | STIM1 | TRPC4 | BRAF |
| CCNA1 | CCNE2 | PPP3CB | CALM1 | CAMK1D | CAMK2D | ORAI1 | STIM2 | TRPC5 | CA9 |
| CCNA2 | CTF1 | PPP3CC | CALM2 | CAMK1G | CAMK2G | ORAI2 | TRPC1 | TRPC6 | CALR |

FIG. 5e illustrates the Signature Score for the Calcium Signaling pathway in response to different doses of CTO at 8 hr and 24 hr compared with BEZ235 and Tarceva® for 24 hr. ANOVA was used to filter informative genes (FDR<0.05 and 1.5 FC).

Strong suppression of non-voltage dependent calcium genes was noted across CTO treatment in both literature determined regulation and ANOVA determined set. Table 7.

TABLE 7

| \ | \ | \ | Symbol: | \ | \ | \ | \ |
|---|---|---|---|---|---|---|---|
| BDNF | CCNE1 | PPP3CC | ORAI3 | TNF | CAMK1 | ORAI1 | BRAF |
| CCNA1 | PPP3CB | CAMK2D | CCND2 | CALM3 | CAMK2G | STIM2 | CALR |

FIG. 6a illustrates the Signature Score for the Canonical Calcium signaling using the KEGG Calcium Signaling and IPA to predict regulation of calcium signaling in response to different doses of CTO at 8 hr and 24 hr compared with BEZ235 and Tarceva® for 24 hr. Table 8.

TABLE 8

| \ | \ | Symbol | \ |
|---|---|---|---|
| PPP3CA | CACNA2D4 | CHRNB3 | HDAC10 |
| PPP3CB | CACNB1 | CHRNB4 | HDAC11 |
| PPP3CC | CACNB2 | CHRND | HDAC2 |
| PPP3R1 | CACNB3 | CHRNE | HDAC3 |
| PPP3R2 | CACNB4 | CHRNG | HDAC4 |
| ATP2C1 | CACNG1 | GRIA1 | HDAC5 |
| CACNA1A | CHRFAM7A | GRIA2 | HDAC6 |
| CACNA1B | CHRNA1 | GRIA3 | HDAC7 |
| CACNA1C | CHRNA10 | GRIA4 | HDAC8 |

TABLE 8-continued

| \ | \ | Symbol | \ |
|---|---|---|---|
| CACNA1D | CHRNA2 | GRIK1 | HDAC9 |
| CACNA1F | CHRNA3 | GRIN1 | HTR3A |
| CACNA1G | CHRNA4 | GRIN2A | RYR1 |
| CACNA1H | CHRNA5 | GRIN2B | SLC8A1 |
| CACNA1I | CHRNA6 | GRIN2C | TNNC1 |
| CACNA1S | CHRNA7 | GRIN2D | \ |
| CACNA2D1 | CHRNA9 | GRIN3A | \ |
| CACNA2D2 | CHRNB1 | GRIN3B | \ |
| CACNA2D3 | CHRNB2 | HDAC1 | \ |

FIG. 6b illustrates the Signature Score for the Canonical Calcium signaling ex vivo using the KEGG Calcium Signaling and IPA to predict regulation of in response to different doses of CTO at 8 hr and 24 hr compared with BEZ235 and Tarceva® for 24 hr. Suppression noted for 6/78 canonical pathway genes only. Table 9

TABLE 9

| Gene Symbol: | | | | | | |
|---|---|---|---|---|---|---|
| HDAC3 | HDAC4 | PPP3CC | GRIA3 | CACNB3 | HDAC8 | PPP3CC |
| HDAC4 | PPP3CB | ATP2C1 | GRIA3 | GRIA3 | PPP3CC | PPP3CC |

Example 7

FIG. 7a illustrates the Signature Score for all Signaling genes after merging of the ANOVA filtered gene sets for both the CAI signature (FIG. 5b) and the non-voltage dependent (NVD) gene sets (FIG. 5c).

FIG. 7b illustrates results in a panel of 31 CAI/Calcium related genes capable of separating the different CTO doses, both by signature view and by PCA. Table 10 provides the list of 31 genes.

TABLE 10

| Gene Symbol | Source |
|---|---|
| AKT1 | CAI |
| AKT2 | CAI |
| BAG3 | CAI |
| CASP3 | CAI |
| CCND1 | CAI |
| CEBPA | CAI |
| FOS | CAI |
| HSP90AA1 | CAI |
| HSP90AB1 | CAI |
| HSP90B1 | CAI |
| JUN | CAI |
| MAPK1 | CAI |
| MAPK3 | CAI |
| MAPK7 | CAI |
| BDNF | Non-voltage |
| BRAF | Non-voltage |
| CALM3 | Non-voltage |
| CALR | Non-voltage |
| CAMK1 | Non-voltage |
| CAMK2D | Non-voltage |
| CAMK2G | Non-voltage |
| CCNA1 | Non-voltage |
| CCND2 | Non-voltage |
| CCNE1 | Non-voltage |
| ORAI1 | Non-voltage |
| ORAI3 | Non-voltage |
| PPP3CB | Non-voltage |
| PPP3CC | Non-voltage |
| STIM2 | Non-voltage |
| TNF | Non-voltage |
| ATP2C1 | KEGG |
| CACNB3 | KEGG |
| GRIA3 | KEGG |
| HDAC3 | KEGG |
| HDAC4 | KEGG |

Results of bioinformatic analysis of data obtained in response to varying doses of CTO at 8 hr and 24 hrs indicate that the early growth response 1 gene product (EGR1) was up regulated 6 fold by CTO treatment. In contrast EGR1 was suppressed by BEZ235 and Tarceva®. The up regulation of EGR1 generally regulates multiple tumor suppressor pathways inducing apoptotic downstream events. Liu, C et al Proc Natl Acad Sci 93: 11831-11836 (1996).

FIG. 8 illustrates the EGR1 Signaling Pathway

Example 8

The carcinoembryonic antigen-related cell adhesion molecule (CEACAM1) (also known as CD66a) was down regulated in response to both CTO and Tarceva® treatment. Dystonin was down regulated by 60 fold in response to CTO treatment.

TGF-β signaling was inhibited in response to treatment with CTO.

The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Those skilled in the art will recognize, or be able to ascertain using no more than routine experimentation, any equivalents to the specific embodiments of the invention described herein. Such equivalents are intended to be encompassed by the claims.

What is claimed is:

1. A method for quantifying the response to carboxyamidotriazole orotate (CTO) on more than one signature pathway wherein said signature pathways are RAS, GFS, MEKi, HDAC, NOTCH, WNTβ-catenin, HSP90, EGFR, p53, EGR1, CEACAMI, TGFβ or Dystonin and on pharmacodynamic biomarkers for each of said signature pathways, said method comprising:
   a) obtaining a cell sample obtained from a subject and treating cultures of the cell sample with varying doses of CTO alone, and maintaining the cultures for different time periods;
   b) isolating the mRNA from the treated cultures of the cell sample obtained in step a), and preparing representative cDNA therefrom, and measuring the transcriptional alteration in expression in the treated cultures of the cell sample;
   c) calculating a signature score for each of the pharmacodynamics biomarkers of each of said signature pathways using the Ingenuity Pathway Analysis (IPA) System and quantitating the response to the varying doses of CTO, and selecting a list of overlapping genes expressing after 8 hours and 24 hours of exposure to CTO based on the calculated signature scores, from the list consisting of:

| Probeset ID | Entrez Gene | Gene Symbol |
|---|---|---|
| 222450_at | 56937 | PMEPA1 |
| 233565_s_at | 100528031///27111 | FKBP1A-SDCBP2///SDCBP2 |
| 242832_at | 5187 | PER1 |
| 240463_at | — | — |
| 213039_at | 23370 | ARHGEF18 |
| 235072_s_at | 63971 | KIF13A |
| 208926_at | 4758 | NEU1 |
| 237444_at | — | — |
| 239451_at | — | — |
| 222288_at | — | — |
| 227579_at | 2241 | FER |
| 212717_at | 9842 | PLEKHM1 |
| 226853_at | 55589 | BMP2K |

| Probe | Gene ID | Symbol |
|---|---|---|
| 214112_s_at | 541578///91966 | CXorf40A///CXorf40B |
| 209012_at | 7204 | TRIO |
| 219476_at | 79098 | C1orf116 |
| 238086_at | 100129617 | LOC100129617 |
| 230721_at | 730094 | C16orf52 |
| 1566079_at | 647190 | RPS16P5 |
| 223839_s_at | 6319 | SCD |
| 225671_at | 124976 | SPNS2 |
| 212961_x_at | 541578 | CXorf40B |
| 223659_at | 84000 | TMPRSS13 |
| 229909_at | 283358 | B4GALNT3 |
| 223467_at | 51655 | RASD1 |
| 235146_at | 57458 | TMCC3 |
| 235548_at | 164284 | APCDD1L |
| 206816_s_at | 26206 | SPAG8 |
| 242323_at | 81579 | PLA2G12A |
| 224579_at | 81539 | SLC38A1 |
| 213315_x_at | 91966 | CXorf40A |
| 227314_at | 3673 | ITGA2 |
| 227093_at | 57602 | USP36 |
| 200760_s_at | 10550 | ARL6IP5 |
| 201790_s_at | 1717 | DHCR7 |
| 1554980_a_at | 467 | ATF3 |
| 242255_at | 22884 | WDR37 |
| 219267_at | 51228 | GLTP |
| 1555786_s_at | 645687 | LINC00520 |
| 229734_at | 283174 | LOC283174 |
| 242856_at | — | — |
| 201037_at | 5214 | PFKP |
| 1562970_at | — | — |
| 201465_s_at | 3725 | JUN |
| 202067_s_at | 3949 | LDLR |
| 223679_at | 1499 | CTNNB1 |
| 201235_s_at | 7832 | BTG2 |
| 225662_at | 51776 | ZAK |
| 204401_at | 3783 | KCNN4 |
| 222906_at | 28982 | FLVCR1 |
| 238613_at | 51776 | ZAK |
| 206414_s_at | 8853 | ASAP2 |
| 210794_s_at | 55384 | MEG3 |
| 226621_at | 9180 | OSMR |
| 230682_x_at | 8714 | ABCC3 |
| 235668_at | 639 | PRDM1 |
| 205483_s_at | 9636 | ISG15 |
| 215808_at | 5655 | KLK10 |
| 212281_at | 27346 | TMEM97 |
| 212282_at | 27346 | TMEM97 |
| 226287_at | 91057 | CCDC34 |
| 213618_at | 116984 | ARAP2 |
| 231089_at | 100505664 | LOC100505664 |
| 227140_at | 3624 | INHBA |
| 231467_at | — | — |
| 202967_at | 2941 | GSTA4 |
| 230323_at | 120224 | TMEM45B |
| 224471_s_at | 8945 | BTRC |
| 202708_s_at | 8349 | HIST2H2BE |
| 242871_at | 54852 | PAQR5 |
| 205627_at | 978 | CDA |
| 235542_at | 200424 | TET3 |
| 240410_at | — | — |
| 236656_s_at | 100288911 | LOC100288911 |
| 206164_at | 9635 | CLCA2 |
| 203159_at | 2744 | GLS |
| 224991_at | 80790 | CMIP |
| 204258_at | 1105 | CHD1 |
| 228249_at | 119710 | C11orf74 |
| 229013_at | 145783 | LOC145783 |
| 211547_s_at | 5048 | PAFAH1B1 |
| 226863_at | 642273 | FAM110C |
| 208161_s_at | 8714 | ABCC3 |
| 214805_at | 1973 | EIF4A1 |
| 229429_x_at | 728855///728875 | LOC728855///LOC728875 |
| 202720_at | 26136 | TES |
| 224995_at | 56907 | SPIRE1 |
| 214771_x_at | 23164 | MPRIP |
| 201939_at | 10769 | PLK2 |
| 238587_at | 84959 | UBASH3B |
| 232113_at | — | — |
| 208690_s_at | 9124 | PDLIM1 |
| 201464_x_at | 3725 | JUN |
| 236657_at | 100288911 | LOC100288911 |
| 215541_s_at | 1729 | DIAPH1 |
| 238028_at | 647024 | C6orf132 |
| 226893_at | 27 | ABL2 |
| 237576_x_at | 100506480 | LOC100506480 |
| 1552256_a_at | 949 | SCARB1 |
| 215255_at | 22997 | IGSF9B |
| 1557258_a_at | 8915 | BCL10 |
| 240623_at | — | — |
| 228754_at | 6533 | SLC6A6 |
| 217257_at | 6452 | SH3BP2 |
| 241036_at | — | — |
| 242553_at | 8714 | ABCC3 |
| 239358_at | — | — |
| 210868_s_at | 79071 | ELOVL6 |
| 200815_s_at | 5048 | PAFAH1B1 |
| 208436_s_at | 3665 | IRF7 |
| 208138_at | 2520 | GAST |
| 241780_at | — | — |
| 200730_s_at | 7803 | PTP4A1 |
| 219697_at | 9956 | HS3ST2 |
| 201693_s_at | 1958 | EGR1 |
| 218847_at | 10644 | IGF2BP2 |
| 230469_at | 219790 | RTKN2 |
| 209917_s_at | 11257 | TP53TG1 |
| 224329_s_at | 84518 | CNFN |
| 212253_x_at | 100652766///667 | DST///LOC100652766 |
| 238058_at | 150381 | LOC150381 |
| 239334_at | 57488 | ESYT2 |
| 222271_at | — | — |
| 216718_at | 388699 | LINC00302 |
| 219076_s_at | 5827 | PXMP2 |
| 204475_at | 4312 | MMP1 |
| 221185_s_at | 84223 | IQCG |
| 203586_at | 379 | ARL4D |
| 217802_s_at | 64710 | NUCKS1 |
| 205767_at | 2069 | EREG |
| 228360_at | 130576 | LYPD6B |
| 228917_at | — | — |
| 228748_at | 966 | CD59 |
| 219632_s_at | 23729///7442 | SHPK///TRPV1 |
| 238715_at | 646014 | LOC646014 |
| 218810_at | 80149 | ZC3H12A |
| 225177_at | 80223 | RAB11FIP1 |
| 224454_at | 55500 | ETNK1 |
| 209498_at | 634 | CEACAM1 |
| 1557257_at | 8915 | BCL10 |
| 225133_at | 51274 | KLF3 |
| 202340_x_at | 3164 | NR4A1 |
| 1556545_at | — | — |
| 212474_at | 23080 | AVL9 |
| 210241_s_at | 11257 | TP53TG1 |
| 243543_at | — | — |
| 239132_at | 4842 | NOS1 |
| 222757_s_at | 51776 | ZAK |
| 201194_at | 6415 | SEPW1 |
| 229874_x_at | 100506687 | LOC100506687 |
| 202557_at | 6782 | HSPA13 |
| 239669_at | — | — |
| 231907_at | 27 | ABL2 |
| 229074_at | 30844 | EHD4 |
| 205428_s_at | 794 | CALB2 |
| 205822_s_at | 3157 | HMGCS1 |
| 210869_s_at | 4162 | MCAM |
| 225665_at | 51776 | ZAK |
| 212781_at | 5930 | RBBP6 |
| 232355_at | 767579 | SNORD114-3 |
| 213288_at | 129642 | MBOAT2 |
| 221666_s_at | 29108 | PYCARD |
| 203072_at | 4643 | MYO1E |
| 215465_at | 26154 | ABCA12 |
| 224453_s_at | 55500 | ETNK1 |
| 216935_at | 388699 | LINC00302 |
| 209086_x_at | 4162 | MCAM |
| 218833_at | 51776 | ZAK |

| | | |
|---|---|---|
| 209377_s_at | 9324 | HMGN3 |
| 223519_at | 51776 | ZAK |
| 210138_at | 8601 | RGS20 |
| 1558845_at | 100506089 | LOC100506089 |
| 201819_at | 949 | SCARB1 |
| 204310_s_at | 4882 | NPR2 |
| 239377_at | 84285 | EIF1AD |
| 224611_s_at | 80331 | DNAJC5 |
| 219155_at | 26207 | PITPNC1 |
| 227163_at | 119391 | GSTO2 |
| 209633_at | 5523 | PPP2R3A |
| 219681_s_at | 80223 | RAB11FIP1 |
| 221860_at | 3191 | HNRNPL |
| 243296_at | 10135 | NAMPT |
| 237133_at | — | — |
| 1556000_s_at | 55727 | BTBD7 |
| 204681_at | 9771 | RAPGEF5 |
| 215726_at | 1528 | CYB5A |
| 210886_x_at | 11257 | TP53TG1 |
| 226597_at | 92840 | REEP6 |
| 204995_at | 8851 | CDK5R1 |
| 236119_s_at | 6706 | SPRR2G |
| 219228_at | 55422 | ZNF331 |
| 234971_x_at | 113026 | PLCD3 |
| 201127_s_at | 47 | ACLY |
| 226880_at | 64710 | NUCKS1 |
| 209383_at | 1649 | DDIT3 |
| 204168_at | 4258 | MGST2 |
| 239670_at | 65268 | WNK2 |
| 208512_s_at | 4301 | MLLT4 |
| 213281_at | 3725 | JUN |
| 218310_at | 154881///27342 | KCTD7///RABGEF1 |
| 205151_s_at | 9865 | TRIL |
| 218217_at | 59342 | SCPEP1 |
| 205055_at | 3682 | ITGAE |
| 215009_s_at | 100499177 | THAP9-AS1 |
| 227484_at | 57522 | SRGAP1 |
| 239769_at | 1009 | CDH11 |
| 230360_at | 342035 | GLDN |
| 227112_at | 23023 | TMCC1 |
| 201482_at | 5768 | QSOX1 |
| 210337_s_at | 47 | ACLY |
| 203911_at | 5909 | RAP1GAP |
| 206683_at | 7718 | ZNF165 |
| 202935_s_at | 6662 | SOX9 |
| 218951_s_at | 55344 | PLCXD1 |
| 233488_at | 84659 | RNASE7 |
| 202562_s_at | 11161 | C14orf1 |
| 208745_at | 10632 | ATP5L |
| 236078_at | 57707 | KIAA1609 |
| 226226_at | 120224 | TMEM45B |
| 213854_at | 9145 | SYNGR1 |
| 243955_at | — | — |
| 222111_at | 54629 | FAM63B |
| 1560296_at | — | — |
| 240038_at | — | — |
| 211372_s_at | 7850 | IL1R2 |
| 202672_s_at | 467 | ATF3 |
| 218717_s_at | 55214 | LEPREL1 |
| 228366_at | — | — |
| 230516_at | 115416 | MALSU1 |
| 201920_at | 6574 | SLC20A1 |
| 209632_at | 5523 | PPP2R3A |
| 207367_at | 479 | ATP12A |
| 1557256_a_at | — | — |
| 200811_at | 1153 | CIRBP |
| 205201_at | 2737 | GLI3 |
| 227724_at | 728190 | LOC728190 |
| 205403_at | 7850 | IL1R2 |
| 242827_x_at | — | — |
| 228084_at | 81579 | PLA2G12A |
| 209365_s_at | 1893 | ECM1 |
| 243279_at | — | — |
| 224946_s_at | 84317 | CCDC115 |
| 218708_at | 29107 | NXT1 |
| 1560531_at | 353132 | LCE1B |
| 207761_s_at | 25840 | METTL7A |
| 206011_at | 834 | CASP1 |
| 213703_at | 150759 | LINC00342 |
| 224595_at | 23446 | SLC44A1 |
| 224613_s_at | 80331 | DNAJC5 |
| 212504_at | 22982 | DIP2C |
| 213682_at | 10762 | NUP50 |
| 205247_at | 4855 | NOTCH4 |
| 228235_at | 84848 | MGC16121 |
| 242873_at | — | — |
| 205960_at | 5166 | PDK4 |
| 230494_at | 6574 | SLC20A1 |
| 221260_s_at | 81566 | CSRNP2 |
| 224480_s_at | 84803 | AGPAT9 |
| 210180_s_at | 6434 | TRA2B |
| 204621_s_at | 4929 | NR4A2 |
| 217863_at | 8554 | PIAS1 |
| 236423_at | — | — |
| 223421_at | 50626 | CYHR1 |
| 220272_at | 54796 | BNC2 |
| 201791_s_at | 1717 | DHCR7 |
| 215574_at | — | — |
| 224328_s_at | 84648 | LCE3D |
| 211828_s_at | 23043 | TNIK |
| 58367_s_at | 79744 | ZNF419 |
| 218950_at | 64411 | ARAP3 |
| 1552703_s_at | 114769///834 | CARD16///CASP1 |
| 219687_at | 55733 | HHAT |
| 232127_at | 1184 | CLCN5 |
| 218377_s_at | 10069 | RWDD2B |
| 210335_at | 9182 | RASSF9 |
| 227927_at | — | — |
| 227224_at | 55103 | RALGPS2 |
| 224778_s_at | 57551 | TAOK1 |
| 229566_at | 645638 | LOC645638 |
| 202734_at | 9322 | TRIP10 |
| 201851_at | 6455 | SH3GL1 |
| 237337_at | — | — |
| 37152_at | 5467 | PPARD |
| 209687_at | 6387 | CXCL12 |
| 203152_at | 64976 | MRPL40 |
| 201627_s_at | 3638 | INSIG1 |
| 232593_at | 93082 | NEURL3 |
| 224769_at | 57551 | TAOK1 |
| 209702_at | 79068 | FTO |
| 204546_at | 9764 | KIAA0513 |
| 232224_at | 5648 | MASP1 |
| 239930_at | 2590 | GALNT2 |
| 203178_at | 2628 | GATM |
| 235782_at | — | — |
| 218181_s_at | 9448 | MAP4K4 |
| 233520_s_at | 202333 | CMYA5 |
| 213456_at | 25928 | SOSTDC1 |
| 219528_s_at | 64919 | BCL11B |
| 224945_at | 55727 | BTBD7 |
| 214866_at | 5329 | PLAUR |
| 209941_at | 8737 | RIPK1 |
| 226029_at | 57216 | VANGL2 |
| 212596_s_at | 10042 | HMGXB4 |
| 229873_at | 283219 | KCTD21 |
| 226392_at | 5922 | RASA2 |
| 226005_at | 7326 | UBE2G1 |
| 214445_at | 22936 | ELL2 |
| 227680_at | 284695 | ZNF326 |
| 227786_at | 90390 | MED30 |
| 222067_x_at | 3017 | HIST1H2BD |
| 1569106_s_at | 55209 | SETD5 |
| 231785_at | 4909 | NTF4 |
| 223937_at | 27086 | FOXP1 |
| 1558685_a_at | 158960 | LOC158960 |
| 211965_at | 677 | ZFP36L1 |
| 39549_at | 4862 | NPAS2 |
| 203800_s_at | 63931 | MRPS14 |
| 1556321_a_at | — | — |
| 212321_at | 8879 | SGPL1 |
| 222154_s_at | 26010 | SPATS2L |
| 218774_at | 28960 | DCPS |
| 212268_at | 1992 | SERPINB1 |
| 213134_x_at | 10950 | BTG3 |
| 230669_at | 5922 | RASA2 |
| 1559901_s_at | 388815 | LINC00478 |
| 225298_at | 25953 | PNKD |

| | | |
|---|---|---|
| 242558_at | — | — |
| 226043_at | 26086 | GPSM1 |
| 210236_at | 8500 | PPFIA1 |
| 214066_x_at | 4882 | NPR2 |
| 240024_at | 23541 | SEC14L2 |
| 235462_at | 132864 | CPEB2 |
| 1554015_a_at | 1106 | CHD2 |
| 235347_at | 84859 | LRCH3 |
| 230847_at | 56897 | WRNIP1 |
| 201427_s_at | 6414 | SEPP1 |
| 1557905_s_at | 960 | CD44 |
| 219084_at | 64324 | NSD1 |
| 206176_at | 654 | BMP6 |
| 219826_at | 79744 | ZNF419 |
| 212356_at | 23351 | KHNYN |
| 218909_at | 26750 | RPS6KC1 |
| 230555_s_at | 90390 | MED30 |
| 212687_at | 3987 | LIMS1 |
| 203098_at | 9425 | CDYL |
| 229054_at | 677 | ZFP36L1 |
| 236039_at | 284348 | LYPD5 |
| 209661_at | 3801 | KIFC3 |
| 209560_s_at | 8788 | DLK1 |
| 225812_at | 619208 | C6orf225 |
| 227829_at | 120071 | GYLTL1B |
| 238623_at | — | — |
| 229415_at | 54205 | CYCS |
| 209222_s_at | 9885 | OSBPL2 |
| 1555809_at | 83716 | CRISPLD2 |
| 204567_at | 9619 | ABCG1 |
| 232277_at | 64078 | SLC28A3 |
| 237197_at | — | — |
| 225209_s_at | 118424 | UBE2J2 |
| 231916_at | 4842 | NOS1 |
| 212279_at | 27346 | TMEM97 |
| 204862_s_at | 4832 | NME3 |
| 230483_at | — | — |
| 212856_at | 23151 | GRAMD4 |
| 224650_at | 114569 | MAL2 |
| 202963_at | 5993 | RFX5 |
| 225320_at | 90550 | MCU |
| 236274_at | 8662 | EIF3B |
| 209780_at | 57157 | PHTF2 |
| 218823_s_at | 54793 | KCTD9 |
| 227787_s_at | 90390 | MED30 |
| 230296_at | 730094 | C16orf52 |
| 222892_s_at | 55287 | TMEM40 |
| 210610_at | 634 | CEACAM1 |
| 230031_at | 3309 | HSPA5 |
| 238477_at | 10749 | KIF1C |
| 209409_at | 2887 | GRB10 |
| 217995_at | 58472 | SQRDL |
| 226873_at | 54629 | FAM63B |
| 1553722_s_at | 220441 | RNF152 |
| 204710_at | 26100 | WIPI2 |
| 212653_s_at | 23301 | EHBP1 |
| 203979_at | 1593 | CYP27A1 |
| 244350_at | 4651 | MYO10 |
| 223233_s_at | 57530 | CGN |
| 1555967_at | — | — |
| 214355_x_at | 100128553///100142659///340307///441294///643854 | CTAGE15P///CTAGE4///CTAGE6P///CTAGE8///CTAGE9 |
| 214469_at | 3012///8335 | HIST1H2AB///HIST1H2AE |
| 212472_at | 9645 | MICAL2 |
| 228115_at | 64762 | FAM59A |
| 228964_at | 639 | PRDM1 |
| 230027_s_at | 84545 | MRPL43 |
| 207318_s_at | 8621 | CDK13 |
| 221689_s_at | 51227 | PIGP |
| 219270_at | 79094 | CHAC1 |
| 225299_at | 4645 | MYO5B |
| 239770_at | 83850 | ESYT3 |
| 226399_at | 79982 | DNAJB14 |
| 226656_at | 10491 | CRTAP |
| 228852_at | 2029 | ENSA |
| 206239_s_at | 6690 | SPINK1 |
| 210993_s_at | 4086 | SMAD1 |
| 238462_at | 84959 | UBASH3B |
| 211962_s_at | 677 | ZFP36L1 |
| 224666_at | 197370 | NSMCE1 |
| 239028_at | 130574 | LYPD6 |
| 213577_at | 6713 | SQLE |
| 202011_at | 7082 | TJP1 |
| 212254_s_at | 100652766///667 | DST///LOC100652766 |
| 221701_s_at | 64220 | STRA6 |
| 239576_at | 57509 | MTUS1 |
| 234418_x_at | 960 | CD44 |
| 227985_at | 100506098 | LOC100506098 |
| 213462_at | 4862 | NPAS2 |
| 224975_at | 4774 | NFIA |
| 225990_at | 91653 | BOC |
| 240616_at | — | — |
| 219911_s_at | 28231 | SLCO4A1 |
| 224970_at | 4774 | NFIA |
| 214623_at | 26226 | FBXW4P1 |
| 239478_x_at | 55668 | C14orf118 |
| 226909_at | 85460 | ZNF518B |
| 208670_s_at | 23741 | EID1 |
| 206192_at | 1041 | CDSN |
| 222173_s_at | 55357 | TBC1D2 |
| 228450_at | 144100 | PLEKHA7 |
| 1558097_at | 253143 | PRR14L |
| 219373_at | 54344 | DPM3 |
| 230388_s_at | 644246 | KANSL1-AS1 |
| 207098_s_at | 55669 | MFN1 |
| 223484_at | 84419 | C15orf48 |
| 244804_at | 8878 | SQSTM1 |
| 229679_at | 400073 | C12orf76 |
| 225826_at | 326625 | MMAB |
| 213352_at | 23023 | TMCC1 |
| 211883_x_at | 634 | CEACAM1 |
| 210387_at | 8339///8343///8344///8346///8347 | HIST1H2BC///HIST1H2BE///HIST1H2BF///HIST1H2BG///HIST1H2BI |
| 210916_s_at | 960 | CD44 |
| 221432_s_at | 81894 | SLC25A28 |
| 218487_at | 210 | ALAD |
| 223264_at | 59274 | MESDC1 |
| 206356_s_at | 2774 | GNAL |
| 218097_s_at | 79004 | CUEDC2 |
| 228001_at | 757 | TMEM50B |
| 212441_at | 9778 | KIAA0232 |
| 201854_s_at | 23300 | ATMIN |
| 121_at | 7849 | PAX8 |
| 222143_s_at | 64419 | MTMR14 |
| 1558002_at | 11171 | STRAP |
| 226040_at | — | — |
| 226141_at | 91050 | CCDC149 |
| 1556567_at | 4676 | NAP1L4 |
| 226263_at | 154007 | SNRNP48 |
| 212074_at | 23353 | SUN1 |
| 227387_at | 54780 | NSMCE4A |
| 232795_at | — | — |
| 203936_s_at | 4318 | MMP9 |
| 225033_at | 6482 | ST3GAL1 |
| 209509_s_at | 7105 | TSPAN6 |
| 213351_s_at | 23023 | TMCC1 |
| 203047_at | 6793 | STK10 |
| 220721_at | 80110 | ZNF614 |
| 1556127_at | 23181 | DIP2A |
| 215016_x_at | 100652766///667 | DST///LOC100652766 |
| 206576_s_at | 634 | CEACAM1 |
| 240674_at | 3720 | JARID2 |
| 225646_at | 1075 | CTSC |
| 1554010_at | 3340 | NDST1 |
| 204100_at | 7067 | THRA |
| 221840_at | 5791 | PTPRE |
| 209078_s_at | 25828 | TXN2 |
| 218530_at | 29109 | FHOD1 |
| 235434_at | — | — |
| 230063_at | 9422 | ZNF264 |

| Probeset ID | Gene ID | Gene Symbol |
|---|---|---|
| 40420_at | 6793 | STK10 |
| 221027_s_at | 81579 | PLA2G12A |
| 244202_at | — | — |
| 212108_at | 23197 | FAF2 |
| 204294_at | 275 | AMT |
| 225503_at | 207063 | DHRSX |
| 212810_s_at | 6509 | SLC1A4 |
| 214814_at | 91746 | YTHDC1 |
| 228468_at | 84930 | MASTL |
| 209108_at | 7105 | TSPAN6 |
| 220444_at | 79230 | ZNF557 |
| 206172_at | 3598 | IL13RA2 |
| 225002_s_at | 25870 | SUMF2 |
| 212205_at | 94239 | H2AFV |
| 228851_s_at | 2029 | ENSA |
| 209048_s_at | 23613 | ZMYND8 |
| 211846_s_at | 5818 | PVRL1 |
| 238909_at | 6281 | S100A10 |
| 205503_at | 5784 | PTPN14 |
| 243829_at | 673 | BRAF |
| 244379_at | — | — |
| 223251_s_at | 55608 | ANKRD10 |
| 202633_at | 11073 | TOPBP1 |
| 214502_at | 8970 | HIST1H2BJ |
| 221773_at | 2004 | ELK3 |
| 41858_at | 27315 | PGAP2 |
| 212850_s_at | 4038 | LRP4 |
| 223408_s_at | — | — |
| 214472_at | 3013///8350///8351///8352///8353///8354///8355///8356///8357///8358/ | HIST1H2AD///HIST1H3A///HIST1H3B///HIST1H3C///HIST1H3D///HIST1H3E///HIST1H3F///HIST1H3G///HIST1H3H///HIST1H3I///HIST1H3J |
| 225647_s_at | 1075 | CTSC |
| 1559977_a_at | 284723 | SLC25A34 |
| 211347_at | 8555 | CDC14B |
| 1558208_at | — | — |
| 227570_at | 144110 | TMEM86A |
| 227492_at | 100506658///647859 | LOC647859///OCLN |
| 1558778_s_at | 57496 | MKL2 |
| 31637_s_at | 7067///9572 | NR1D1///THRA |
| 229190_at | 100507376 | LOC100507376 |
| 236188_s_at | 4676 | NAP1L4 |
| 212503_s_at | 22982 | DIP2C |
| 204760_s_at | 7067///9572 | NR1D1///THRA |
| 212099_at | 388 | RHOB |
| 214873_at | 91355 | LRP5L |
| 228181_at | 7779 | SLC30A1 |
| 212763_at | 23271 | CAMSAP2 |
| 226285_at | 4076 | CAPRIN1 |
| 213567_at | 3840 | KPNA4 |
| 203927_at | 4794 | NFKBIE |
| 208523_x_at | 8339///8343///8344///8346///8347 | HIST1H2BC///HIST1H2BE///HIST1H2BF///HIST1H2BG///HIST1H2BI |
| 219389_at | 55061 | SUSD4 |
| 202329_at | 1445 | CSK |
| 238523_at | 79786 | KLHL36 |
| 1565016_at | 3276 | PRMT1 |
| 226409_at | 128637 | TBC1D20 |
| 229926_at | 100500850 | MIR3682 |
| 208527_x_at | 8339///8343///8344///8346///8347 | HIST1H2BC///HIST1H2BE///HIST1H2BF///HIST1H2BG///HIST1H2BI |
| 223598_at | 5887 | RAD23B |
| 243797_at | 9262 | STK17B |
| 203317_at | 23550 | PSD4 |
| 230965_at | 9099 | USP2 |
| 208490_x_at | 8339///8343///8344///8346///8347 | HIST1H2BC///HIST1H2BE///HIST1H2BF///HIST1H2BG///HIST1H2BI |
| 235514_at | 151516 | ASPRV1 |
| 209098_s_at | 182 | JAG1 |
| 1554229_at | 153222 | CREBRF |
| 209398_at | 3006 | HIST1H1C |
| 202629_at | 10513 | APPBP2 |
| 203428_s_at | 25842 | ASF1A |
| 238005_s_at | 25942 | SIN3A |
| 214455_at | 8339///8343///8344///8346///8347 | HIST1H2BC///HIST1H2BE///HIST1H2BF///HIST1H2BG///HIST1H2BI |
| 214073_at | 2017 | CTTN |
| 203140_at | 604 | BCL6 |
| 232150_at | — | — |
| 208546_x_at | 8345 | HIST1H2BH |
| 243446_at | 84962 | AJUBA |
| 236207_at | 6744 | SSFA2 |
| 212016_s_at | 5725 | PTBP1 |
| 232311_at | 567 | B2M |
| 219711_at | 54807 | ZNF586 |
| 208579_x_at | 54145///85236 | H2BFS///HIST1H2BK |
| 239493_at | 6129 | RPL7 |
| 214074_s_at | 2017 | CTTN |
| 228091_at | 55014 | STX17 |
| 234331_s_at | 151354 | FAM84A |
| 212372_at | 4628 | MYH10 |

| Probeset ID | Gene Title |
|---|---|
| 222450_at | prostate transmembrane protein, androgen induced 1 |
| 233565_s_at | FKBP1A-SDCBP2 readthrough (non-protein coding)///syndecan binding protein (syntenin) |
| 242832_at | period homolog 1 (Drosophila) |
| 240463_at | — |
| 213039_at | Rho/Rac guanine nucleotide exchange factor (GEF) 18 |
| 235072_s_at | kinesin family member 13A |
| 208926_at | sialidase 1 (lysosomal sialidase) |
| 237444_at | — |
| 239451_at | — |
| 222288_at | — |
| 227579_at | fer (fps/fes related) tyrosine kinase |
| 212717_at | pleckstrin homology domain containing, family M (with RUN domain) member 1 |
| 226853_at | BMP2 inducible kinase |
| 214112_s_at | chromosome X open reading frame 40A///chromosome X open reading frame 40B |
| 209012_at | triple functional domain (PTPRF interacting) |
| 219476_at | chromosome 1 open reading frame 116 |
| 238086_at | uncharacterized LOC100129617 |
| 230721_at | chromosome 16 open reading frame 52 |
| 1566079_at | ribosomal protein S16 pseudogene 5 |
| 223839_s_at | stearoyl-CoA desaturase (delta-9-desaturase) |
| 225671_at | spinster homolog 2 (Drosophila) |
| 212961_x_at | chromosome X open reading frame 40B |
| 223659_at | transmembrane protease, serine 13 |
| 229909_at | beta-1,4-N-acetyl-galactosaminyl |

| | |
|---|---|
| 223467_at | transferase 3 RAS, dexamethasone-induced 1 |
| 235146_at | transmembrane and coiled-coil domain family 3 |
| 235548_at | adenomatosis polyposis coli down-regulated 1-like |
| 206816_s_at | sperm associated antigen 8 |
| 242323_at | phospholipase A2, group XIIA |
| 224579_at | solute carrier family 38, member 1 |
| 213315_x_at | chromosome X open reading frame 40A |
| 227314_at | integrin, alpha 2 (CD49B, alpha 2 subunit of VLA-2 receptor) |
| 227093_at | Ubiquitin specific peptidase 36 |
| 200760_s_at | ADP-ribosylation-like factor 6 interacting protein 5 |
| 201790_s_at | 7-dehydrocholesterol reductase |
| 1554980_a_at | activating transcription factor 3 |
| 242255_at | WD repeat domain 37 |
| 219267_at | glycolipid transfer protein |
| 1555786_s_at | long intergenic non-protein coding RNA 520 |
| 229734_at | uncharacterized LOC283174 |
| 242856_at | — |
| 201037_at | phosphofructokinase, platelet |
| 1562970_at | — |
| 201465_s_at | jun proto-oncogene |
| 202067_s_at | low density lipoprotein receptor |
| 223679_at | catenin (cadherin-associated protein), beta 1, 88kDa |
| 201235_s_at | BTG family, member 2 |
| 225662_at | sterile alpha motif and leucine zipper containing kinase AZK |
| 204401_at | potassium intermediate/small conductance calcium-activated channel, subfamily N, member |
| 222906_at | feline leukemia virus subgroup C cellular receptor 1 |
| 238613_at | sterile alpha motif and leucine zipper containing kinase AZK |
| 206414_s_at | ArfGAP with SH3 domain, ankyrin repeat and PH domain 2 |
| 210794_s_at | maternally expressed 3 (non-protein coding) |
| 226621_at | oncostatin M receptor |
| 230682_x_at | ATP-binding cassette, sub-family C (CFTR/MRP), member3 |
| 235668_at | PR domain containing 1, with ZNF domain |
| 205483_s_at | ISG15 ubiquitin-like modifier |
| 215808_at | kallikrein-related peptidase 10 |
| 212281_s_at | transmembrane protein 97 |
| 212282_at | transmembrane protein 97 |
| 226287_at | coiled-coil domain containing 34 |
| 213618_at | ArfGAP with RhoGAP domain, ankyrin repeat and PH domain 2 |
| 231089_at | uncharacterized LOC100505664 |
| 227140_at | inhibin, beta A |
| 231467_at | — |
| 202967_at | glutathione S-transferase alpha 4 |
| 230323_s_at | transmembrane protein 45B |
| 224471_s_at | beta-transducin repeat containing E3 ubiquitin protein ligase |
| 202708_s_at | histone cluster 2, H2be |
| 242871_at | progestin and adipoQ receptor family member V |
| 205627_at | cytidine deaminase |
| 235542_at | tet methylcytosine dioxygenase 3 |
| 240410_at | — |
| 236656_s_at | uncharacterized LOC100288911 |
| 206164_at | chloride channel accessory 2 |
| 203159_at | glutaminase |
| 224991_at | c-Maf inducing protein |
| 204258_at | chromodomain helicase DNA binding protein 1 |
| 228249_at | chromosome 11 open reading frame 74 |
| 229013_at | uncharacterized LOC145783 |
| 211547_s_at | platelet-activating factor acetylhydrolase lb, regulatory subunit 1 (45kDa) |
| 226863_at | family with sequence similarity 110, member C |
| 208161_s_at | ATP-binding cassette, sub-family C (CFTR/MRP), member 3 |
| 214805_at | eukaryotic translation initiation factor 4A1 |
| 229429_x_at | uncharacterized LOC728855/// uncharacterized LOC728875 |
| 202720_at | testis derived transcript (3 LIM domains) |
| 224995_at | spire homolog 1 (Drosophila) |
| 214771_x_at | myosin phosphatase Rho interacting protein |
| 201939_at | polo-like kinase 2 |
| 238587_at | ubiquitin associated and SH3 domain containing B |
| 232113_at | — |
| 208690_s_at | PDZ and LIM domain 1 |
| 201464_x_at | jun proto-oncogene |
| 236657_at | uncharacterized LOC100288911 |
| 215541_s_at | diaphanous homolog 1 (Drosophila) |
| 238028_at | chromosome 6 open reading frame 132 |
| 226893_at | v-abl Abelson murine leukemia viral oncogene homolog 2 |
| 237576_x_at | uncharacterized LOC100506480 |
| 1552256_a_at | scavenger receptor class B, member 1 |
| 215255_at | immunoglobulin superfamily, member 9B |
| 1557258_a_at | B-cell CLL/lymphoma 10 |
| 240623_at | solute carrier family 6 (neurotransmitter transporter, taurine), member 6 |
| 228754_at | |
| 217257_at | SH3-domain binding protein 2 |
| 241036_at | — |
| 242553_at | ATP-binding cassette, sub-family C (CFTR/MRP), member 3 |
| 239358_at | — |
| 210868_s_at | ELOVL fatty acid elongase 6 |
| 200815_s_at | platelet-activating factor acetylhydrolase lb, regulatory subunit 1 (45kDa) |
| 208436_s_at | interferon regulatory factor 7 |
| 208138_at | gastrin |
| 241780_at | — |
| 200730_s_at | protein tyrosine phosphatase type IVA, member 1 |
| 219697_at | heparan sulfate (glucosamine) 3-0-sulfotransferase 2 |
| 201693_s_at | early growth response 1 |
| 218847_at | insulin-like growth factor 2 mRNA binding protein 2 |
| 230469_at | rhotekin 2 |
| 209917_s_at | TP53 target 1 (non-protein coding) |
| 224329_s_at | cornifelin |
| 212253_x_at | dystonin///dystonin-like |
| 238058_at | uncharacterized LOC150381 |
| 239334_at | Extended synaptotagmin-like protein 2 |
| 222271_at | — |
| 216718_at | long intergenic non-protein coding RNA 302 |

| Probe ID | Description |
|---|---|
| 219076_s_at | peroxisomal membrane protein 2, 22kDa |
| 204475_at | matrix metallopeptidase 1 (interstitial collagenase) |
| 221185_s_at | IQ motif containing G |
| 203586_s_at | ADP-ribosylation factor-like 4D |
| 217802_s_at | nuclear casein kinase and cyclin-dependent kinase substrate 1 |
| 205767_at | epiregulin |
| 228360_at | LY6/PLAUR domain containing 6B |
| 228917_at | — |
| 228748_at | CD59 molecule, complement regulatory protein |
| 219632_s_at | sedoheptulokinase///transient receptor potential cation channel, subfamily V, member |
| 238715_at | Uncharacterized LOC646014 |
| 218810_at | zinc finger CCCH-type containing 12A |
| 225177_at | RAB11 family interacting protein 1 (class I) |
| 224454_at | ethanolamine kinase 1 |
| 209498_at | carcinoembryonic antigen-related cell adhesion molecule 1 (biliary glycoprotein) |
| 1557257_at | B-cell CLL/lymphoma 10 |
| 225133_at | Kruppel-like factor 3 (basic) |
| 202340_x_at | nuclear receptor subfamily 4, group A, member 1 |
| 1556545_at | — |
| 212474_at | AVL9 homolog (S. cerevisiae) |
| 210241_s_at | TP53 target 1 (non-protein coding) |
| 243543_at | — |
| 239132_at | nitric oxide synthase 1 (neuronal) |
| 222757_s_at | sterile alpha motif and leucine zipper containing kinase AZK |
| 201194_at | selenoprotein W, 1 |
| 229874_x_at | uncharacterized LOC100506687 |
| 202557_at | heat shock protein 70kDa family, member 13 |
| 239669_at | — |
| 231907_at | v-abl Abelson murine leukemia viral oncogene homolog 2 |
| 229074_at | EH-domain containing 4 |
| 205428_s_at | calbindin 2 |
| 205822_s_at | 3-hydroxy-3-methylglutaryl-CoA synthase 1 (soluble) |
| 210869_s_at | melanoma cell adhesion molecule |
| 225665_at | sterile alpha motif and leucine zipper containing kinase AZK |
| 212781_at | retinoblastoma binding protein 6 |
| 232355_at | small nucleolar RNA, C/D box 114-3 |
| 213288_at | membrane bound 0-acyltransferase domain containing 2 |
| 221666_s_at | PYD and CARD domain containing |
| 203072_at | myosin IE |
| 215465_at | ATP-binding cassette, sub-family A (ABC1), member 12 |
| 224453_s_at | ethanolamine kinase 1 |
| 216935_at | long intergenic non-protein coding RNA 302 |
| 209086_x_at | melanoma cell adhesion molecule |
| 218833_at | sterile alpha motif and leucine zipper containing kinase AZK |
| 209377_s_at | high mobility group nucleosomal binding domain 3 |
| 223519_at | sterile alpha motif and leucine zipper containing kinase AZK |
| 210138_at | regulator of G-protein signaling 20 |
| 1558845_at | uncharacterized LOC100506089 |
| 201819_at | scavenger receptor class B, member 1 |
| 204310_s_at | natriuretic peptide receptor B/guanylate cyclase B (atrionatriuretic peptide receptor B |
| 239377_at | eukaryotic translation initiation factor 1A domain containing |
| 224611_s_at | DnaJ (Hsp40) homolog, subfamily C, member 5 |
| 219155_at | phosphatidylinositol transfer protein, cytoplasmic 1 |
| 227163_at | glutathione S-transferase omega 2 |
| 209633_at | protein phosphatase 2, regulatory subunit B", alpha |
| 219681_s_at | RAB11 family interacting protein 1 (class I) |
| 221860_at | heterogeneous nuclear ribonucleoprotein L |
| 243296_at | Nicotinamide phosphoribosyltransferase |
| 237133_at | — |
| 1556000_s_at | BTB (POZ) domain containing 7 |
| 204681_s_at | Rap guanine nucleotide exchange factor (GEF) 5 |
| 215726_s_at | cytochrome b5 type A (microsomal) |
| 210886_x_at | TP53 target 1 (non-protein coding) |
| 226597_at | receptor accessory protein 6 |
| 204995_at | cyclin-dependent kinase 5, regulatory subunit 1 (p35) |
| 236119_s_at | small proline-rich protein 2G |
| 219228_at | zinc finger protein 331 |
| 234971_x_at | phospholipase C, delta 3 |
| 201127_s_at | ATP citrate lyase |
| 226880_at | Nuclear casein kinase and cyclin-dependent kinase substrate 1 |
| 209383_at | DNA-damage-inducible transcript 3 |
| 204168_at | microsomal glutathione S-transferase 2 |
| 239670_at | WNK lysine deficient protein kinase 2 |
| 208512_s_at | myeloid/lymphoid or mixed-lineage leukemia (trithorax homolog, Drosophila); translocate |
| 213281_at | Jun proto-oncogene |
| 218310_at | potassium channel tetramerisation domain containing 7//I RAB guanine nucleotide exchan |
| 205151_s_at | TLR4 interactor with leucine-rich repeats |
| 218217_at | serine carboxypeptidase 1 |
| 205055_at | integrin, alpha E (antigen CD103, human mucosal lymphocyte antigen 1; alpha polypeptide |
| 215009_s_at | THAP9 antisense RNA 1 (non-protein coding) |
| 227484_at | SLIT-ROBO Rho GTPase activating protein 1 |
| 239769_at | Cadherin 11, type 2, OB-cadherin (osteoblast) |
| 230360_at | gliomedin |
| 227112_at | transmembrane and coiled-coil domain family 1 |
| 201482_at | quiescin 06 sulfhydryl oxidase 1 |
| 210337_s_at | ATP citrate lyase |
| 203911_at | RAP1 GTPase activating protein |
| 206683_at | zinc finger protein 165 |

| | |
|---|---|
| 202935_s_at | SRY (sex determining region Y)-box 9 |
| 218951_s_at | phosphatidylinositol-specific phospholipase C, X domain containing 1 |
| 233488_at | ribonuclease, RNase A family, 7 |
| 202562_s_at | chromosome 14 open reading frame 1 |
| 208745_at | ATP synthase, H+ transporting, mitochondrial Fo complex, subunit G |
| 236078_at | KIAA1609 |
| 226226_at | transmembrane protein 45B |
| 213854_at | synaptogyrin 1 |
| 243955_at | — |
| 222111_at | family with sequence similarity 63, member B |
| 1560296_at | — |
| 240038_at | — |
| 211372_s_at | interleukin 1 receptor, type II |
| 202672_s_at | activating transcription factor 3 |
| 218717_s_at | leprecan-like 1 |
| 228366_at | — |
| 230516_at | Mitochondrial assembly of ribosomal large subunit 1 |
| 201920_at | solute carrier family 20 (phosphate transporter), member 1 |
| 209632_at | protein phosphatase 2, regulatory subunit B″, alpha |
| 207367_at | ATPase, H+/K+ transporting, nongastric, alpha polypeptide |
| 1557256_a_at | — |
| 200811_at | cold inducible RNA binding protein |
| 205201_at | GLI family zinc finger 3 |
| 227724_at | uncharacterized LOC0728190 |
| 205403_at | interleukin 1 receptor, type II |
| 242827_x_at | — |
| 228084_at | phospholipase A2, group XIIA |
| 209365_s_at | extracellular matrix protein 1 |
| 243279_at | — |
| 224946_s_at | coiled-coil domain containing 115 |
| 218708_at | NTF2-like export factor 1 |
| 1560531_at | late cornified envelope 1B |
| 207761_s_at | methyltransferase like 7A |
| 206011_at | caspase 1, apoptosis-related cysteine peptidase |
| 213703_at | long intergenic non-protein coding RNA 342 |
| 224595_at | solute carrier family 44, member 1 |
| 224613_s_at | DnaJ (Hsp40) homolog, subfamily C, member 5 |
| 212504_at | DIP2 disco-interacting protein 2 homolog C (Drosophila) |
| 213682_at | nucleoporin 50kDa |
| 205247_at | notch 4 |
| 228235_at | uncharacterized protein MGC16121 |
| 242873_at | — |
| 205960_at | pyruvate dehydrogenase kinase, isozyme 4 |
| 230494_at | solute carrier family 20 (phosphate transporter), member 1 |
| 221260_s_at | cysteine-serine-rich nuclear protein 2 |
| 224480_s_at | 1-acylglycerol-3-phosphate O-acyltransferase 9 |
| 210180_s_at | transformer 2 beta homolog (Drosophila) |
| 204621_s_at | nuclear receptor subfamily 4, group A, member 2 |
| 217863_at | protein inhibitor of activated STAT, 1 |
| 236423_at | — |
| 223421_at | cysteine/histidine-rich 1 |
| 220272_at | basonuclin 2 |
| 201791_s_at | 7-dehydrocholesterol reductase |
| 215574_at | — |
| 224328_s_at | late cornified envelope 3D |
| 211828_s_at | TRAF2 and NCK interacting kinase |
| 58367_s_at | zinc finger protein 419 |
| 218950_at | ArfGAP with RhoGAP domain, ankyrin repeat and PH domain 3 |
| 1552703_s_at | caspase recruitment domain family, member 16///caspase 1, apoptosis-related cysteine |
| 219687_at | hedgehog acyltransferase |
| 232127_at | chloride channel, voltage-sensitive 5 |
| 218377_s_at | RWD domain containing 2B |
| 210335_at | Ras association (RalGDS/AF-6) domain family (N-terminal) member 9 |
| 227927_at | — |
| 227224_at | Ral GEF with PH domain and SH3 binding motif 2 |
| 224778_s_at | TAO kinase 1 |
| 229566_at | WDNM1-like pseudogene |
| 202734_at | thyroid hormone receptor interactor 10 |
| 201851_at | SH3-domain GRB2-like 1 |
| 237337_at | — |
| 37152_at | peroxisome proliferator-activated receptor delta |
| 209687_at | chemokine (C-X-C motif) ligand 12 |
| 203152_at | mitochondrial ribosomal protein L40 |
| 201627_s_at | insulin induced gene 1 |
| 232593_at | neuralized homolog 3 (Drosophila) pseudogene |
| 224769_at | TAO kinase 1 |
| 209702_at | fat mass and obesity associated |
| 204546_at | KIAA0513 |
| 232224_at | mannan-binding lectin serine peptidase 1 (C4/C2 activating component of Ra-reactive fac |
| 239930_at | UDP-N-acetyl-alpha-D-galactosamine: polypeptide N-acetylgalactosaminyl-transferase 2 (Gal |
| 203178_at | glycine amidinotransferase (L-arginine: glycine amidinotransferase) |
| 235782_at | — |
| 218181_s_at | mitogen-activated protein kinase kinase kinase kinase 4 |
| 233520_s_at | cardiomyopathy associated 5 |
| 213456_at | sclerostin domain containing 1 |
| 219528_s_at | B-cell CLL/lymphoma 11B (zinc finger protein) |
| 224945_at | BTB (POZ) domain containing 7 |
| 214866_at | plasminogen activator, urokinase receptor |
| 209941_at | receptor (TNFRSF)-interacting serine-threonine kinase 1 |
| 226029_at | yang-like 2 (van gogh, Drosophila) |
| 212596_s_at | HMG box domain containing 4 |
| 229873_at | potassium channel tetramerisation domain containing 21 |
| 226392_at | RAS p21 protein activator 2 |
| 226005_at | ubiquitin-conjugating enzyme E2G 1 |
| 214445_at | elongation factor, RNA polymerase II, 2 |
| 227680_at | zinc finger protein 326 |
| 227786_at | mediator complex subunit 30 |
| 222067_x_at | histone cluster 1, H2bd |
| 1569106_s_at | SET domain containing 5 |
| 231785_at | neurotrophin 4 |
| 223937_at | forkhead box P1 |
| 1558685_a_at | uncharacterized protein BC009467 |

| | |
|---|---|
| 211965_at | zinc finger protein 36, C3H type-like 1 |
| 39549_at | neuronal PAS domain protein 2 |
| 203800_s_at | mitochondrial ribosomal protein S14 |
| 1556321_a_at | — |
| 212321_at | sphingosine-1-phosphate lyase 1 |
| 222154_s_at | spermatogenesis associated, serine-rich 2-like |
| 218774_at | decapping enzyme, scavenger |
| 212268_at | serpin peptidase inhibitor, clade B (ovalbumin), member 1 |
| 213134_x_at | BTG family, member 3 |
| 230669_at | RAS p21 protein activator 2 |
| 1559901_s_at | long intergenic non-protein coding RNA 478 |
| 225298_at | paroxysmal nonkinesigenic dyskinesia |
| 242558_at | — |
| 226043_at | G-protein signaling modulator 1 |
| 210236_at | protein tyrosine phosphatase, receptor type, f polypeptide (PTPRF), interacting protein |
| 214066_x_at | natriuretic peptide receptor B/guanylate cyclase B (atrionatriuretic peptide receptor B |
| 240024_at | SEC14-like 2 (S. cerevisiae) |
| 235462_at | Cytoplasmic polyadenylation element binding protein 2 |
| 1554015_a_at | chromodomain helicase DNA binding protein 2 |
| 235347_at | leucine-rich repeats and calponin homology (CH) domain containing 3 |
| 230847_at | Werner helicase interacting protein 1 |
| 201427_s_at | selenoprotein P, plasma, 1 |
| 1557905_s_at | CD44 molecule (Indian blood group) |
| 219084_at | nuclear receptor binding SET domain protein 1 |
| 206176_at | bone morphogenetic protein 6 |
| 219826_at | zinc finger protein 419 |
| 212356_at | KH and NYN domain containing |
| 218909_at | ribosomal protein S6 kinase, 52kDa, polypeptide 1 |
| 230555_s_at | Mediator complex subunit 30 |
| 212687_at | LIM and senescent cell antigen-like domains 1 |
| 203098_at | chromodomain protein, Y-like |
| 229054_at | zinc finger protein 36, C3H type-like 1 |
| 236039_at | LY6/PLAUR domain containing 5 |
| 209661_at | kinesin family member C3 |
| 209560_s_at | delta-like 1 homolog (Drosophila) |
| 225812_at | chromosome 6 open reading frame 225 |
| 227829_at | glycosyltransferase-like 1B |
| 238623_at | — |
| 229415_at | cytochrome c, somatic |
| 209222_s_at | oxysterol binding protein-like 2 |
| 1555809_at | cysteine-rich secretory protein LCCL domain containing 2 |
| 204567_s_at | ATP-binding cassette, sub-family G (WHITE), member 1 |
| 232277_at | solute carrier family 28 (sodium-coupled nucleoside transporter), member 3 |
| 237197_at | — |
| 225209_s_at | ubiquitin-conjugating enzyme E2, J2 |
| 231916_at | nitric oxide synthase 1 (neuronal) |
| 212279_at | transmembrane protein 97 |
| 204862_s_at | NME/NM23 nucleoside diphosphate kinase 3 |
| 230483_at | — |
| 212856_at | GRAM domain containing 4 |
| 224650_at | mal, T-cell differentiation protein 2 (gene/pseudogene) |
| 202963_at | regulatory factor X, 5 (influences HLA class II expression) |
| 225320_at | mitochondrial calcium uniporter |
| 236274_at | eukaryotic translation initiation factor 3, subunit B |
| 209780_at | putative homeodomain transcription factor 2 potassium channel |
| 218823_s_at | tetramerisation domain containing 9 |
| 227787_s_at | mediator complex subunit 30 |
| 230296_at | chromosome 16 open reading frame 52 |
| 222892_s_at | transmembrane protein 40 |
| 210610_at | carcinoembryonic antigen-related cell adhesion molecule1 (biliary glycoprotein) |
| 230031_at | heat shock 70kDa protein 5 (glucose-regulated protein, 78kDa) |
| 238477_at | kinesin family member 1C |
| 209409_at | growth factor receptor-bound protein 10 |
| 217995_at | sulfide quinone reductase-like (yeast) |
| 226873_at | family with sequence similarity 63, member B |
| 1553722_s_at | ring finger protein 152 |
| 204710_s_at | WD repeat domain, phosphoinositide interacting 2 |
| 212653_s_at | EH domain binding protein 1 |
| 203979_at | cytochrome P450, family 27, subfamily A, polypeptide 1 |
| 244350_at | myosin X |
| 223233_s_at | cingulin |
| 1555967_at | — |
| 214355_x_at | CTAGE family, member 15, pseudogene///CTAGE family, member 4///CTAGE family, member |
| 214469_at | histone cluster 1, H2ab/// histone cluster 1, H2ae |
| 212472_at | microtubule associated monooxygenase, calponin and LIM domain containing 2 |
| 228115_at | family with sequence similarity 59, member A |
| 228964_at | PR domain containing 1, with ZNF domain |
| 230027_s_at | mitochondrial ribosomal protein L43 |
| 207318_s_at | cyclin-dependent kinase 13 |
| 221689_s_at | phosphatidylinositol glycan anchor biosynthesis, class P |
| 219270_at | ChaC, cation transport regulator homolog 1 (E. coli) |
| 225299_at | myosin VB |
| 239770_at | extended synaptotagmin-like protein 3 |
| 226399_at | DnaJ (Hsp40) homolog, subfamily B, member 14 |
| 226656_at | cartilage associated protein |
| 228852_at | endosulfine alpha |
| 206239_s_at | serine peptidase inhibitor, Kazal type 1 |
| 210993_s_at | SMAD family member 1 |
| 238462_at | ubiquitin associated and SH3 domain containing B |
| 211962_s_at | zinc finger protein 36, C3H type-like 1 |
| 224666_at | non-SMC element 1 homolog (S. cerevisiae) |

| | |
|---|---|
| 239028_at | LY6/PLAUR domain containing 6 |
| 213577_at | squalene epoxidase |
| 202011_at | tight junction protein 1 (zona occludens 1) |
| 212254_s_at | dystonin///dystonin-like |
| 221701_s_at | stimulated by retinoic acid gene 6 homolog (mouse) |
| 239576_at | microtubule associated tumor suppressor 1 |
| 234418_x_at | CD44 molecule (Indian blood group) |
| 227985_at | uncharacterized LOC100506098 |
| 213462_at | neuronal PAS domain protein 2 |
| 224975_at | nuclear factor I/A |
| 225990_at | Boc homolog (mouse) |
| 240616_at | — |
| 219911_s_at | solute carrier organic anion transporter family, member 4A1 |
| 224970_at | nuclear factor I/A |
| 214623_at | F-box and WD repeat domain containing 4 pseudogene 1 |
| 239478_x_at | chromosome 14 open reading frame 118 |
| 226909_at | zinc finger protein 518B |
| 208670_s_at | EP300 interacting inhibitor of differentiation 1 |
| 206192_at | corneodesmosin |
| 222173_s_at | TBC1 domain family, member 2 |
| 228450_at | pleckstrin homology domain containing, family A member 7 |
| 1558097_at | proline rich 14-like |
| 219373_at | dolichyl-phosphate mannosyltransferase polypeptide 3 |
| 230388_s_at | KANSL1 antisense RNA 1 (non-protein coding) |
| 207098_s_at | mitofusin 1 |
| 223484_at | chromosome 15 open reading frame 48 |
| 244804_at | sequestosome 1 |
| 229679_at | chromosome 12 open reading frame 76 |
| 225826_at | methylmalonic aciduria (cobalamin deficiency) cbIB type |
| 213352_at | transmembrane and coiled-coil domain family 1 |
| 211883_x_at | carcinoembryonic antigen-related cell adhesion molecule 1 (biliary glycoprotein) |
| 210387_at | histone cluster 1, H2bc/// histone cluster 1, H2be/// histone cluster 1, H2bf///his |
| 210916_s_at | CD44 molecule (Indian blood group) |
| 221432_s_at | solute carrier family 25 (mitochondrial iron transporter), member 28 |
| 218487_at | aminolevulinate dehydratase |
| 223264_at | mesoderm development candidate 1 |
| 206356_s_at | guanine nucleotide binding protein (G protein), alpha activating activity polypeptide, |
| 218097_s_at | CUE domain containing 2 |
| 228001_at | transmembrane protein 50B |
| 212441_at | KIAA0232 |
| 201854_s_at | ATM interactor |
| 121_at | paired box 8 |
| 222143_s_at | myotubularin related protein 14 |
| 1558002_at | Serine/threonine kinase receptor associated protein |
| 226040_at | — |
| 226141_at | coiled-coil domain containing 149 |
| 1556567_at | nucleosome assembly protein 1-like 4 |
| 226263_at | small nuclear ribonucleoprotein 48kDa (U11/U12) |
| 212074_at | Sad1 and UNC84 domain containing 1 |
| 227387_at | Non-SMC element 4 homolog A (S. cerevisiae) |
| 232795_at | — |
| 203936_s_at | matrix metallopeptidase 9 (gelatinase B, 92kDa gelatinase, 92kDa type IV collagenase) |
| 225033_at | ST3 beta-galactoside alpha-2,3-sialyltransferase 1 |
| 209109_s_at | tetraspanin 6 |
| 213351_s_at | transmembrane and coiled-coil domain family 1 |
| 203047_at | serine/threonine kinase 10 |
| 220721_at | zinc finger protein 614 |
| 1556127_at | DIP2 disco-interacting protein 2 homolog A (Drosophila) |
| 215016_x_at | dystonin///dystonin-like |
| 206576_s_at | carcinoembryonic antigen-related cell adhesion molecule 1 (biliary glycoprotein) |
| 240674_at | jumonji, AT rich interactive domain 2 |
| 225646_at | cathepsin C |
| 1554010_at | N-deacetylase/N-sulfotransferase (heparan glucosaminyl) 1 |
| 204100_at | thyroid hormone receptor, alpha |
| 221840_at | protein tyrosine phosphatase, receptor type, E |
| 209078_s_at | thioredoxin 2 |
| 218530_at | formin homology 2 domain containing 1 |
| 235434_at | — |
| 230063_at | zinc finger protein 264 |
| 40420_at | serine/threonine kinase 10 |
| 221027_s_at | phospholipase A2, group XIIA |
| 244202_at | — |
| 212108_at | Fas associated factor family member 2 |
| 204294_at | aminomethyltransferase |
| 225503_at | dehydrogenase/reductase (SDR family) X-linked |
| 212810_s_at | solute carrier family 1 (glutamate/neutral amino acid transporter), member 4 |
| 214814_at | YTH domain containing 1 |
| 228468_at | microtubule associated serine/threonine kinase-like |
| 209108_at | tetraspanin 6 |
| 220444_at | zinc finger protein 557 |
| 206172_at | interleukin 13 receptor, alpha 2 |
| 225502_at | sulfatase modifying factor 2 |
| 212205_at | H2A histone family, member V |
| 228851_s_at | endosulfine alpha |
| 209048_s_at | zinc finger, MYND-type containing 8 |
| 211846_s_at | poliovirus receptor-related 1 (herpesvirus entry mediator C) |
| 238909_at | S100 calcium binding protein A10 |
| 205503_at | protein tyrosine phosphatase, non-receptor type 14 |
| 243829_at | v-raf murine sarcoma viral oncogene homolog B1 |
| 244379_at | — |
| 223251_s_at | ankyrin repeat domain 10 |
| 202633_at | topoisomerase (DNA) II binding protein 1 |
| 214502_at | histone cluster 1, H2bj |
| 221773_at | ELK3, ETS-domain protein (SRF accessory protein 2) |
| 41858_at | post-GPI attachment to proteins 2 |
| 212850_s_at | low density lipoprotein receptor-related protein 4 |
| 223408_s_at | — |

-continued

| | |
|---|---|
| 214472_at | histone cluster 1, H2ad///histone cluster 1, H3a///histone cluster 1, H3b///histo |
| 225647_s_at | cathepsin C |
| 1559977_a_at | solute carrier family 25, member 34 |
| 211347_at | CDC14 homolog B (S. cerevisiae) |
| 1558208_at | — |
| 227570_at | transmembrane protein 86A |
| 227492_at | occludin pseudogene///occludin |
| 1558778_s_at | MKL/myocardin-like 2 |
| 31637_s_at | nuclear receptor subfamily 1, group D, member 1///thyroid hormone receptor, alpha |
| 229190_at | uncharacterized LOC100507376 |
| 236188_s_at | Nucleosome assembly protein 1-like 4 |
| 212503_s_at | DIP2 disco-interacting protein 2 homolog C (Drosophila) |
| 204760_s_at | nuclear receptor subfamily 1, group D, member 1///thyroid hormone receptor, alpha |
| 212099_at | ras homolog family member B |
| 214873_at | low density lipoprotein receptor-related protein 5-like |
| 228181_at | solute carrier family 30 (zinc transporter), member 1 |
| 212763_at | calmodulin regulated spectrin-associated protein family, member 2 |
| 226285_at | cell cycle associated protein 1 |
| 213567_at | karyopherin alpha 4 (importin alpha 3) |
| 203927_at | nuclear factor of kappa light polypeptide gene enhancer in B-cells inhibitor, epsilon |
| 208523_x_at | histone cluster 1, H2bc///histone cluster 1, H2be///histone cluster 1, H2bf///his |
| 219389_at | sushi domain containing 4 |
| 202329_at | c-src tyrosine kinase |
| 238523_at | kelch-like 36 (Drosophila) |
| 1565016_at | protein arginine methyltransferase 1 |
| 226409_at | TBC1 domain family, member 20 |
| 229926_at | microRNA 3682 |
| 208527_x_at | histone cluster 1, H2bc///histone cluster 1, H2be///histone cluster 1, H2bf///his |
| 223598_at | RAD23 homolog B (S. cerevisiae) |
| 243797_at | serine/threonine kinase 17b |
| 203317_at | pleckstrin and Sec7 domain containing 4 |
| 230965_at | ubiquitin specific peptidase 2 |
| 208490_x_at | histone cluster 1, H2bc///histone cluster 1, H2be///histone cluster 1, H2bf///his |
| 235514_at | aspartic peptidase, retroviral-like 1 |
| 209098_s_at | jagged 1 |
| 1554229_at | CREB3 regulatory factor |
| 209398_at | histone cluster 1, H1c |
| 202629_at | amyloid beta precursor protein (cytoplasmic tail) binding protein 2 |
| 203428_s_at | ASF1 anti-silencing function 1 homolog A (S. cerevisiae) |
| 238005_s_at | SIN3 transcription regulator homolog A (yeast) |
| 214455_at | histone cluster 1, H2bc///histone cluster 1, H2be///histone cluster 1, H2bf///his |
| 214073_at | cortactin |
| 203140_at | B-cell CLL/lymphoma 6 |
| 232150_at | — |
| 208546_x_at | histone cluster 1, H2bh |
| 243446_at | ajuba LIM protein |
| 236207_at | sperm specific antigen 2 |
| 212016_s_at | polypyrimidine tract binding protein 1 |
| 232311_at | Beta-2-microglobulin |
| 219711_at | zinc finger protein 586 |
| 208579_x_at | H2B histone family, member S (pseudogene)///histone cluster 1, H2bk |
| 239493_at | ribosomal protein L7 |
| 214074_s_at | cortactin |
| 228091_at | syntaxin 17 |
| 234331_s_at | family with sequence similarity 84, member A |
| 212372_at | myosin, heavy chain 10, non-muscle |

Or, from genes for each of the pharmacodynamic biomarkers from the list further consisting of:

| | | | | |
|---|---|---|---|---|
| MMP2 | ESR1 | FOS | PCLG2 | MAPK6 |
| JUN | COND1 | PPAR1 | MAPK1 | MAPK7 |
| CEBPA | MAPK3 | PCLG1 | MAPK4 | MAPK12 |
| AKT2 | CASP3 | FOS | HSP90AB1 | JUN |
| BAG3 | CCND1 | HASP90AA1 | HSP90B1 | AKT1 |
| ARG2 | CCNA1 | CCND2 | CCNE2 | TNF |
| BDNF | CCNA2 | CCNE1 | CTF1 | BRAF |
| ARG2 | CCND2 | TNF | PPP3R1 | CALM3 |
| BDNF | CCNE1 | PPP3CA | PPP3R2 | CAMK1 |
| CCNA1 | CCNE2 | PPP3CB | CALM1 | CAMK1D |
| CCNA2 | CTF1 | PPP3CC | CALM2 | CAMK1G |
| BDNF | CCNE1 | PPP3CC | ORAI3 | TNF |
| CCNA1 | PPP3CB | CAMK2D | CCND2 | CALM3 |
| PPP3CA | CACNA2D4 | CHRNB3 | HDAC10 | |
| PPP3CB | CACNB1 | CHRNB4 | HDAC11 | |
| PPP3CC | CACNB2 | CHRND | HDAC2 | |
| PPP3R1 | CACNB3 | CHRNE | HDAC3 | |
| PPP3R2 | CACNB4 | CHRNG | HDAC4 | |
| ATP2C1 | CACNG1 | GRIA1 | HDAC5 | |
| CACNA1A | CHRFAM7A | GRIA2 | HDAC6 | |
| CACNA1B | CHRNA1 | GRIA3 | HDAC7 | |
| CACNA1C | CHRNA10 | GRIA4 | HDAC8 | |
| CACNA1D | CHRNA2 | GRIK1 | HDAC9 | |
| CACNA1F | CHRNA3 | GRIN1 | HTR3A | |
| CACNA1H | CHRNA5 | GRIN2B | SLC8A1 | |
| CACNA2I | CHRNA6 | GRIN2C | TNNC1 | |
| CACNA1G | CHRNA4 | GRIN2A | RYR1 | |
| CACNA1S | CHRNA7 | GRIN2D | | |
| CACNA2D1 | CHRNA9 | GRIN3A | | |
| CACNA2D2 | CHRNB1 | GRIN3B | | |
| CACNA2D3 | CHRNB2 | HDAC1 | | |
| CACNA2D1 | CHRNA9 | GRIN3A | | |
| CACNA2D2 | CHRNB1 | GRIN3B | | |
| CACNA2D3 | CHRNB2 | HDACC1 | | |

| | | | | |
|---|---|---|---|---|
| MAP15 | AKT1 | MOS3 | HSP90B1 | |
| CASP3 | AKT2 | HSP90AA1 | Hsp84-2 | |
| HSPA8 | AKT3 | HSP90AB1 | Hsp84-3 | |
| | | | BAG3 | |
| CEBPA | MAPK3 | | | |
| MAPK1 | MAPK7 | | | |
| CA9 | | | | |
| CALR | | | | |
| CAMK2A | CAMK4 | ORAI3 | TRPC3 | TRPC7 |
| CAMK2B | NOS2 | STIM1 | TRPC4 | BRAF |
| CAMK2D | ORAI2 | STIM2 | TRPC5 | CA9 |
| CAMK2G | ORAI2 | TRPC1 | TRPC6 | CALR |
| CAMK1 | ORAI2 | BRAF | | |
| CAMK2G | STIM2 | CALR | | |

Or, from genes for each of the pharmacodynamic biomarkers from the list further consisting of:

| | | | |
|---|---|---|---|
| ABCC5 | CYHR1 | HIST3H2A | POU2F3 |
| ATP6V1B1 | DEPTOR | HOXB13 | RAMP1 |
| ATXN3 | DNAL4 | ING4 | SEMA3G |
| BCAS1 | EIF4A2 | OVGP1 | SEPP1 |
| BCL2L11 | EPHX2 | PCMTD1 | SIDT2 |
| CALCOCO1 | ERBB3 | PCMTD2 | AREG |
| CAPN13 | HIST1H2AC | PDIA4 | BTG3 |
| CRBN | HIST1H2BD | PLEKHG4 | CEBPG |
| | CORO1C | IFRD1 | PFKP |
| | DLEU2 | IMPAD1 | PNPT1 |
| | DPH3 | KLK6 | PSMC4 |
| | EIF5 | KPNA4 | RPS6KA3 |
| | ENO2 | LRP8 | S100A2 |
| | HN1 | MALL | SERPINB5 |
| | HSP90AA1 | MTHFD1L | SERPINB8 |
| | HSPA4L | PADI1 | SLC7A1 |
| | | | SRXN1 |
| | | | TIPIN; | and
d) identifying, using the calculated signature scores and quantitated responses, each of the pharmacodynamics biomarkers of each of the signature pathways by at least 3 or more genes listed in 1c).

2. The method of claim 1, wherein the pharmacodynamic biomarkers of each of the signature pathways further include at least 3 or more genes for which pharmacodynamics biomarkers are from the list consisting of:

| | | | |
|---|---|---|---|
| ABCC5 | CYHR1 | HIST3H2A | POU2F3 |
| ATP6V1B1 | DEPTOR | HOXB13 | RAMP1 |
| ATXN3 | DNAL4 | ING4 | SEMA3G |
| BCAS1 | EIF4A2 | OVGP1 | SEPP1 |
| BCL2L11 | EPHX2 | PCMTD1 | SIDT2 |
| CALC0001 | ERBB3 | PCMTD2 | AREG |
| CAPN13 | HIST1H2AC | PDIA4 | BTG3 |
| CRBN | HIST1H2BD | PLEKHG4 | CEBPG |
| | CORO1C | IFRD1 | PFKP |
| | DLEU2 | IMPAD1 | PNPT1 |
| | DPH3 | KLK6 | PSMC4 |
| | EIF5 | KPNA4 | RPS6KA3 |
| | EN02 | LRP8 | S100A2 |
| | HN1 | MALL | SERPINB5 |
| | HSP9OAA1 | MTHFD1L | SERPINB8 |
| | HSPA4L | PADI1 | SLC7A1 |
| | | | SRXN1 |
| | | | TIPIN. |

3. The method of claim 2, wherein at least one of the signature pathways is RAS.

4. The method of claim 3, wherein the signature score of the pharmacodynamic biomarkers of the signature pathways for RAS is inhibited in response to exposure to CTO.

5. The method of claim 2, wherein at least one of the signature pathways is GFS.

6. The method of claim 5, wherein the signature score of the pharmacodynamic biomarkers of the signature pathways for GFS is inhibited in response to exposure to CTO.

7. The method of claim 1, wherein at least one of the signature pathways is MEKi.

8. The method of claim 5, wherein the signature score of the pharmacodynamic biomarkers of the signature pathways for MEKi is inhibited in response to exposure to CTO.

9. The method of claim 1, wherein at least one of the signature pathways is HDAC.

10. The method of claim 9, wherein the signature score of the pharmacodynamic biomarkers of the signature pathways for HDAC is inhibited in response to exposure to CTO.

11. The method of claim 1, wherein at least one of the signature pathways is NOTCH.

12. The method of claim 11, wherein the signature score of the pharmacodynamic biomarkers of the signature pathways for NOTCH is inhibited in response to exposure to CTO.

13. The method of claim 1, wherein at least one of the signature pathways is WNTβ-catenin.

14. The method of claim 13, wherein the signature score of the pharmacodynamic biomarkers of the signature pathways for WNTβ-catenin is inhibited in response to exposure to CTO.

15. The method of claim 1, wherein at least one of the signature pathways is HSP90.

16. The method of claim 15, wherein the signature score of the pharmacodynamic biomarkers of the signature pathways for HSP90 is inhibited in response to exposure to CTO.

17. The method of claim 1, wherein at least one of the signature pathways is EGFR.

18. The method of claim 17, wherein the signature score of the pharmacodynamic biomarkers of the signature pathways for EGFR is inhibited in response to exposure to CTO.

19. The method of claim 1, wherein at least one of the signature pathways is P53.

20. The method of claim 19, wherein the signature score of the pharmacodynamic biomarkers of the signature pathways for P53 is induced in response to exposure to CTO.

21. The method of claim 1, wherein at least one of the signature pathways is EGR1.

22. The method of claim 21, wherein the signature score of the pharmacodynamic biomarkers of the signature pathways for EGR1 is stimulated in response to exposure to CTO.

23. The method of claim 1, wherein at least one of the signature is CEACAMI.

24. The method of claim 23, wherein the signature score of the pharmacodynamic biomarkers of the signature pathways for CEACAMI is stimulated in response to exposure to CTO.

25. The method of claim 1, wherein at least one of the signature pathways is TGFβ.

26. The method of claim 25, wherein the signature score of the pharmacodynamic biomarkers of the signature pathways for TGFβ is stimulated in response to exposure to CTO.

27. The method of claim 1, wherein at least one of the signature pathways is Dystonin.

28. The method of claim 27, wherein the signature score of the pharmacodynamic biomarkers of the signature pathways for Dystonin is stimulated in response to exposure to CTO.

* * * * *